(12) United States Patent
Cooper et al.

(10) Patent No.: US 11,717,803 B2
(45) Date of Patent: Aug. 8, 2023

(54) POROUS MATERIALS

(71) Applicant: THE UNIVERSITY OF LIVERPOOL, Liverpool (GB)

(72) Inventors: Andy Cooper, Liverpool (GB); Ming Liu, Liverpool (GB)

( * ) Notice: Subject to any disclaimer, the term of this patent is extended or adjusted under 35 U.S.C. 154(b) by 147 days.

(21) Appl. No.: 16/891,953

(22) Filed: Jun. 3, 2020

(65) Prior Publication Data

US 2020/0353439 A1 Nov. 12, 2020

Related U.S. Application Data

(63) Continuation of application No. 15/569,589, filed as application No. PCT/GB2016/051245 on Apr. 29, 2016, now Pat. No. 10,710,052.

(60) Provisional application No. 62/154,989, filed on Apr. 30, 2015.

(51) Int. Cl.
*B01J 20/22* (2006.01)
*B01D 53/02* (2006.01)
*B01J 20/28* (2006.01)
*C07D 487/22* (2006.01)
*B01J 20/34* (2006.01)

(52) U.S. Cl.
CPC .............. *B01J 20/22* (2013.01); *B01D 53/02* (2013.01); *B01J 20/28057* (2013.01); *B01J 20/28069* (2013.01); *B01J 20/3425* (2013.01); *C07D 487/22* (2013.01); *B01D 2253/20* (2013.01); *B01D 2253/202* (2013.01); *B01D 2257/11* (2013.01); *B01D 2257/504* (2013.01); *B01D 2257/708* (2013.01); *Y02C 20/40* (2020.08); *Y02P 20/151* (2015.11); *Y02P 20/582* (2015.11)

(58) Field of Classification Search
CPC ....... B01J 20/22; B01J 20/3425; B01D 53/02; C07D 487/22
USPC ..................................................... 423/245.1
See application file for complete search history.

(56) References Cited

U.S. PATENT DOCUMENTS

| 2008/0286472 A1 | 11/2008 | Tutin et al. |
| 2009/0000474 A1 | 1/2009 | Macgillivray |
| 2013/0047846 A1 | 2/2013 | Zhang et al. |

FOREIGN PATENT DOCUMENTS

WO 2016/174468 11/2016

OTHER PUBLICATIONS

Bushell, A.F., et al., "Nanoporous Organic Polymer/Cage Composite Membranes," Angewandte Chemie, 2013, vol. 52, pp. 1253-1256.

(Continued)

*Primary Examiner* — Anita Nassiri-Motlagh

(57) ABSTRACT

Porous materials (such as organic polyamine cage compounds) and methods of stabilising porous materials which are otherwise prone to pore-collapse are described. Such stabilisation is accomplished through the use of molecular ties to create bridges between reactive groups of a (potentially) porous material to thereby strengthen and stabilise the porous structure. The chemistry involved in, and the results of, the stabilisation of porous materials to provide a new sorption composition comprising the very materials which are generally prone to pore-collapse are also described.

16 Claims, 16 Drawing Sheets

(56) References Cited

OTHER PUBLICATIONS

PCT Search Report and Written Opinion for PCT/GB2016/051245, completed Jul. 13, 2016.
Ming Liu et al. Journal of the American Chemical Society, vol. 136, No. 21, May 28, 20114, pp. 7583-7586.
Linjiang Chen et al. Nature Materials, vol. 13, No. 10, Oct. 1, 2014, pp. 954-960.
Gang Zhang and Michael Mastalerz, Chem Soc Rev, Royal Society of Chemistry, vol. 43 (2014), pp. 1934-1937.

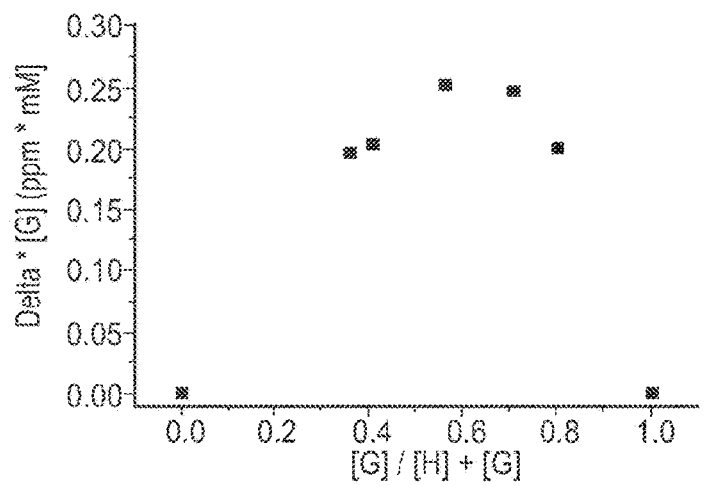
Fig. 10
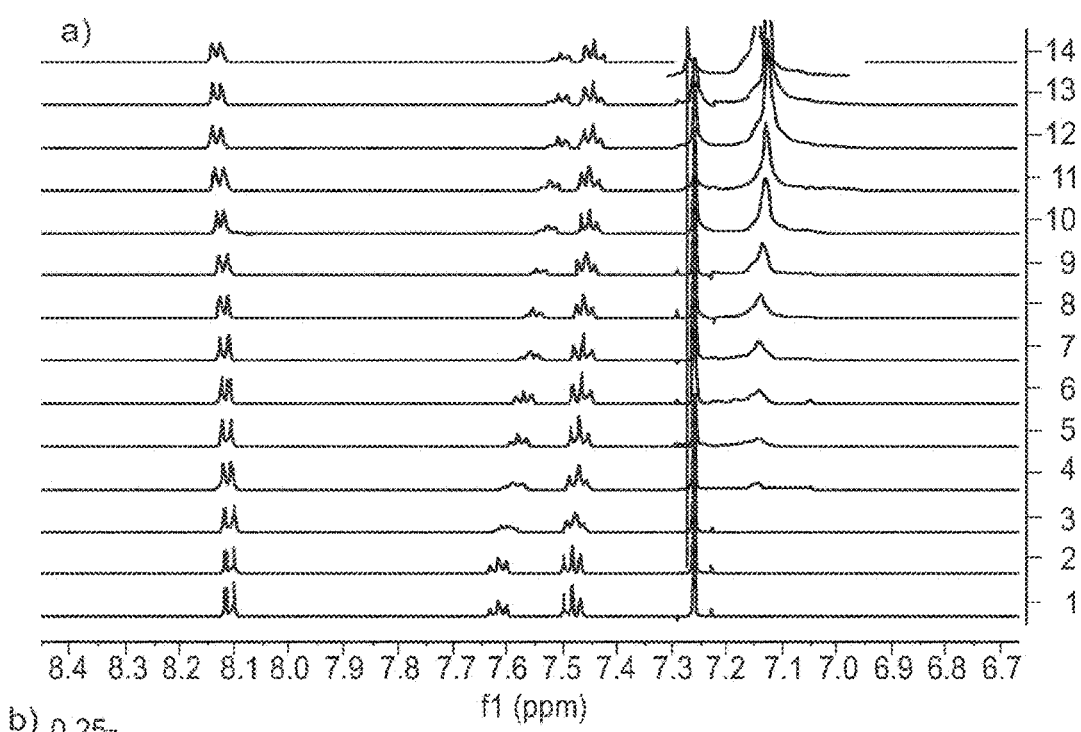
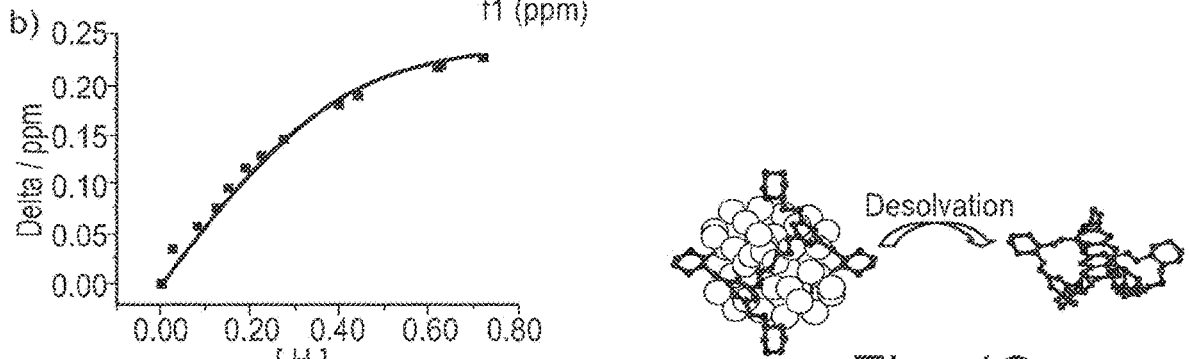
Fig. 11
Fig. 12

POROUS MATERIALS

CROSS-REFERENCE TO RELATED APPLICATIONS

This application is a continuation of U.S. application Ser. No. 15/569,589, filed Oct. 26, 2017, which is a U.S. national application under 35 U.S.C. § 371 of PCT International Application No. PCT/GB2016/051245, filed Apr. 29, 2016, which claims priority to U.S. Provisional Application Ser. No. 62/154,989, filed Apr. 30, 2015, the entire disclosure of each are expressly incorporated by reference herein.

INTRODUCTION

The present invention relates to porous materials (such as organic cage compounds) and methods of stabilising porous materials which are otherwise prone to pore-collapse. The present invention also harnesses the chemistry involved in, and the results of, the stabilisation of porous materials to provide a new sorption composition comprising the very materials which are generally prone to pore-collapse. The present invention also provides various derivative products, methods, and uses related to the aforesaid materials.

BACKGROUND

Porous materials, especially solid porous materials, are widely used in a variety of industrial contexts. For instance, in the field of host-guest chemistry (a particular branch of supramolecular chemistry) many porous materials can serve as "host" components for receiving (sometimes selectively) and reversibly retaining (through non-covalent binding) guest components within the host's pores. Host components may typically comprise compounds such as organic macrocycles, organic cages, covalent organic frameworks (COFs), zeolites and metal organic frameworks (MOFs). Some common host components include inter alia cryptands, crown ethers, cucurbiturils, cyclodextrins, calixarenes, cyclotriveratrylenes, cryptophanes, carcerands, zeolites, porphyrins, pillararenes, metallacrowns, and foldamers.

Of particular interest to the inventors are porous organic solids, such as organic macrocycles and cages, which can be especially useful as adsorbents, for instance for radioisotope pollutants,[7] as molecular additives in organic-organic mixed-matrix membranes,[8] as shape-selective chromatography phases,[9] and as materials for molecular sensing.[10]

Schiff-base chemistry is one of the most versatile methods for the construction of organic macrocycles and cages.[1] The reversibility of the imine bond forming reaction gives a route to thermodynamically equilibrated products. This has been used to produce crystalline porous organic solids, such as covalent organic frameworks (COFs)[2] and porous molecular organic cages.[3] In particular, a series of porous, shape-persistent imine cages has been reported,[4] and surface areas as high as 3758 $m^2$ $g^{-1}$ have been attained,[5] thus rivalling extended frameworks such as MOFs.[6]

However, the reversibility of imine chemistry, which permits equilibrium products to form, can also cause problems of chemical instability, thus limiting its wider application. Imines are prone to hydrolysis and can decompose upon exposure to atmospheric moisture, although there are some exceptions to this.[2,11] Imines are even more prone to hydrolysis in acidic or basic environments. A straightforward way to make an imine more chemically stable is to reduce it to the corresponding amine. In addition to enhancing chemical stability, amine cages are also readily functionalized[12] and can provide binding sites for guests such as $CO_2$.[13] However, while many amine cages and macrocycles have been reported via imine reduction, the resulting porous structures are often inherently unstable owing to the additional flexibility introduced to the cage molecule following imine reduction—i.e. the internal cavities or pores of such cage molecules can be prone to collapse, thereby prematurely nullifying their utility.

By way of example, to illustrate these pore-collapsing problems, the inventors previously reported a [4+6] amine cage formed by reduction of the equivalent imine cage, (designated CC1), but crystallization attempts yielded only amorphous, non-porous solids for the amine derivative. [14]Zhang et al. reported a series of [2+3] amine cages but these, too, collapsed in the absence of solvent, and a very low level of porosity (but a high $CO_2/N_2$ selectivity) was observed.[15] Mastalerz et al reduced their [4+6] salicylbisimine cages to the corresponding amines, but this also resulted in a collapse of the cage, the loss of the intrinsic cage cavity, and a dramatic decrease in porosity.[10,16] These examples all demonstrate that the increased flexibility of saturated amine bonds with respect to unsaturated imine bonds causes loss of shape-persistence in the molecule, even when the parent imine cage is shape-persistent and porous.

It is therefore an object of the present invention to solve at least one problem of the prior art.

Another object of the invention is to provide porous materials which have a relatively high degree of chemical stability across a range of conditions (e.g. stable to hydrolysis at various pHs, stable across a wide temperature range, and/or solvent stable) and a relatively high degree of physical stability (e.g. from a shape-persistence and porosity retention perspective).

SUMMARY OF THE INVENTION

The inventors made the surprising discovery that porous materials vulnerable to pore-collapse (hereinafter "collapsible porous materials") can be stabilised and rendered relatively collapse-resistant through the incorporation of strategic "molecular ties". For instance, chemically-stable yet collapsible amine cages derived (by reduction) from their chemically-unstable parent imine cages can now be physically stabilised (against pore collapse) via the present invention. As such, the present invention can significantly reduce (or even eliminate) the former trade-off between chemical stability and physical stability of porous materials. The present invention therefore not only delivers a robust and broadly-applicable methodology for the stabilisation of porous materials, but also contributes to the art a wide range of previously-unviable host components for use in a variety of industrial contexts (particularly contexts in which the porous nature of the host component is used, typically for receiving and reversibly retaining guest components or otherwise selectively allowing some guests to flow there through whilst excluding others (e.g. filtration).

According to a first aspect of the present invention there is provided a method of stabilising a collapsible substrate, the method comprising reacting the collapsible substrate with a "molecular tie" compound to cause at least one set (or pair) of distinct reactive moieties within the collapsible substrate to become mutually interlinked via a "molecular tie" linker derived from the molecular tie compound (e.g. where on reactive moiety of a pair of reactive moieties becomes interlinked with the other reactive moiety of said pair).

According to a further aspect of the present invention there is provided a method of preparing a stabilised porous material, the method comprising stabilising a collapsible substrate as defined herein.

According to a further aspect of the present invention there is provided a stabilised porous material, obtainable by, obtained by, or directly obtained by the method of preparing a stabilised porous material or the method of stabilising a collapsible substrate as defined herein.

According to a further aspect of the present invention there is provided a stabilised porous material comprising at least one set (or pair) of distinct reactive moieties interlinked via a "molecular tie" linker.

According to a further aspect of the present invention there is provided a method of purifying a collapsible substrate, the method comprising preparing a stabilised porous material or stabilising a collapsible substrate as defined herein to transform the collapsible substrate into a stabilised porous material; purifying the stabilised porous material to provide a purified stabilised porous material; and thereafter regenerating the collapsible substrate from the purified stabilised porous material.

According to a further aspect of the present invention there is provided a method of preparing a sorption composition, the method comprising providing a stabilised porous material as defined herein; and optionally mixing together the stabilised porous material and one or more additional porous materials.

According to a further aspect of the present invention there is provided a sorption composition, obtainable by, obtained by, or directly obtained by the method of preparing a sorption composition as defined herein.

According to a further aspect of the present invention there is provided a sorption composition, comprising a stabilised porous material as defined herein, and optionally one or more additional porous materials.

According to a further aspect of the present invention there is provided a method of sorbing one or more sorbable substrates, the method comprising contacting the one or more sorbable substrates with a sorption composition as defined herein.

According to a further aspect of the present invention there is provided a sorption complex, obtainable by, obtained by, or directly obtained by the method of sorbing as defined herein.

According to a further aspect of the present invention there is provided a sorption complex, the sorption complex comprising one or more sorbable substrates sorbed within and/or upon a stabilised porous material as defined herein.

A method of regenerating a stabilised porous material, or a method of releasing one or more sorbable substrates from within and/or upon a stabilised porous material, the method comprising exposing a sorption complex as defined herein to conditions which release one or more sorbable substrates from within the sorption complex; and optionally thereafter isolating or using the one or more sorbable substrates and/or the stabilised porous material.

According to a further aspect of the present invention there is provided a method of capturing (and/or sorbing) one or more gaseous "molecular tie" compounds, the method comprising contacting the one or more gaseous "molecular tie" compounds with a collapsible substrate as defined herein (i.e. the collapsible substrate which, in the context of the aforementioned aspects, is generally processed and stabilised to produce a stabilised porous material), or composition comprising said collapsible substrate. Suitably at least some of the molecular tie compound reacts with the collapsible substrate to cause at least one set (or pair) of distinct reactive moieties within the collapsible substrate to become mutually interlinked via a "molecular tie" linker derived from the molecular tie compound to thereby produce a stabilised porous material (suitably as defined herein). Suitably at least some of the molecular tie compound is sorbed (without chemically reacting, e.g. physically adsorbed) within pores of the resulting stabilised porous material. Suitably such a method involves "dual sorption" (i.e. involving both chemical capture of the gaseous molecular tie compound, following the aforementioned chemical reaction, and physical capture, following passage of the molecular tie compound into the stabilised pores).

According to a further aspect of the present invention there is provided a sorption complex, obtainable by, obtained by, or directly obtained by the method of capturing as defined herein.

According to a further aspect of the present invention there is provided a sorption complex, the sorption complex comprising one or more gaseous "molecular tie" compounds chemically bound to and physically sorbed within and/or upon a stabilised porous material as defined herein.

According to a further aspect of the present invention there is provided a method of regenerating a stabilised porous material, or a method of releasing one or more gaseous "molecular tie" compounds from a stabilised porous material, the method comprising exposing a sorption complex as defined herein to conditions which release one or more gaseous "molecular tie" compounds from within the sorption complex (optionally releasing substantially only physically sorbed "molecular tie" compounds or releasing both chemically bound and physically sorbed "molecular tie" compounds); and optionally thereafter isolating or using the one or more gaseous "molecular tie" and/or the stabilised porous material.

According to a further aspect of the present invention there is provided a use of a collapsible substrate (i.e. pre-stabilised/unstabilised) as defined herein for sorbing a molecular tie compound.

According to a further aspect of the present invention there is provided a use of a stabilised porous material (i.e. post-stabilised) as defined herein for sorbing a sorbable substrate.

According to a further aspect of the present invention there is provided a use of a stabilised porous material as defined herein or a sorption composition as defined herein for sorbing radon (or indeed other elements and molecules, especially gaseous elements and molecules).

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

FIG. 10 shows graphical Job plots, which suggest the 1:1 stoichiometry of the complex benzoic acid∩FT-RCC3 in $CHCl_3$ by plotting the chemical shift changes of $H_1$ against the mole fraction of the guest. $[H]_0$ and $[G]_0$ are initial concentrations of FT-RCC3 and benzoic acid. $[H]_0$+$[G]_0$=5.00 mM.

FIG. 11 shows (a) Partial $^1$H NMR of benzoic acid (1.00 mM) upon addition of FT-RCC3. (b) The chemical shift changes of $H_1$ on benzoic acid upon addition of FT-RCC3. The red solid line was obtained by non-linear curve-fitting.

FIG. 12 shows (a) Single crystal structure of RCC3 solvate with $H_2O$/methanol guests shown in red; (b) Representative energy-minimized model of a collapsed, desolvated RCC3 amine cage.

DETAILED DESCRIPTION OF THE INVENTION

Definitions

Figure 1:
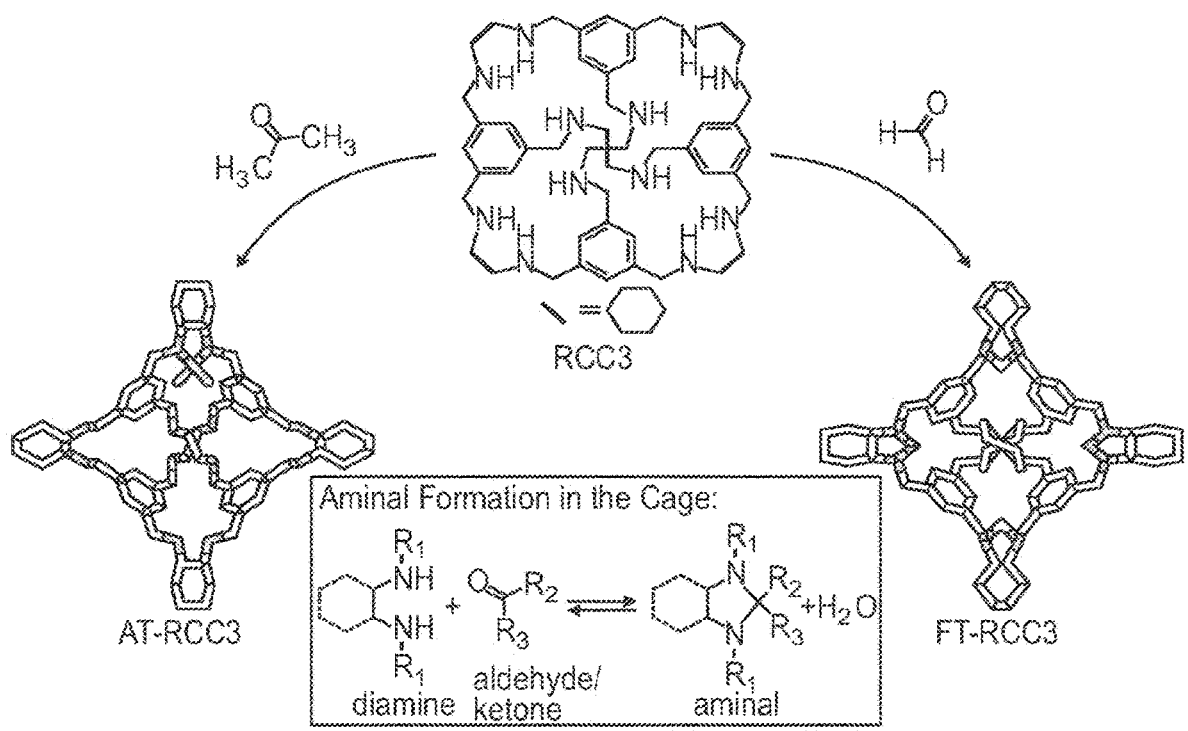
FIG. 1 shows a combination of reaction schemes illustrating how "molecular ties" are incorporated into a collapsible porous organic cage material.

Unless otherwise stated, the following terms used in the specification and claims have the following meanings set out below.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to an "average" value is intended to relate to the mean value.

Herein the terms "sorb", "sorption", "sorbent", "sorbate" refer to the process of sorption of certain compounds (sorbates, sorbable substrates) within/to the pores of a particular solid structure (sorbent material or composition), such as where an "sorbent material" sorbs a desired component from a component mixture. These terms "sorb", "sorption", "sorbent", "sorbate" encompass "absorb", "absorption" "absorbent", and "absorbate", where sorbates are sorbed within the bulk of a sorbent. Moreover, "sorb", "sorption", "sorbent", "sorbate" also encompasses "adsorb", "adsorption", "adsorbent", and "adsorbate" where sorbates are sorbed to the surface of a sorbent. In some embodiments, the term "sorption" means "absorption". In some embodiments, the term "sorption" means "adsorption".

Herein the term "selectively sorb" refers to a process in which a sorbent (i.e. porous solid material) uptakes one sorbate in preference to other components or potential sorbates which are a part of the same original mixture.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1\text{-}x_2:y_1\text{-}y_2:z_1\text{-}z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consist essentially of or consist of the stipulated ingredients and diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free" when used in relation to a given component of a composition (e.g. "a liquid pharmaceutical composition entirely free of compound X"), refers to a composition containing none of said component.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Herein, in the context of the present specification, a "strong acid" is suitably one having a $pK_a$ of −1.0 or less, whereas a "weak acid" is suitably one having a $pK_a$ of 2.0 or more. Herein, in the context of the present specification, a "strong base" is suitably one whose conjugate acid has a $pK_a$ of 12 or higher (suitably 14 or higher), whereas a "weak base" is suitably one whose conjugate acid has a $pK_a$ of 10 or less.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Herein, unless stated otherwise, all chemical nomenclature may be defined in accordance with IUPAC definitions.

Herein, the term "hydrocarbon" is well understood in the art, and refers to compounds containing carbon and hydrogen only. The term "hydrocarbyl" general refers any aliphatic, acyclic, or cyclic (including aryl) hydrocarbon group, suitably with no heteroatoms. Such compounds include, inter alia, alkanes, alkenes, alkynes, arenes, and cyclic versions thereof. The term "hydrocarbon" anthracene, naphthalene, benzene, and/or derivatives thereof (e.g. toluene).

Herein, the term "carbocyclyl", "carbocycle" or "carbocyclic" refers to a radical of a non-aromatic cyclic hydrocarbon group, generally having from 3 to 10 ring carbon atoms (i.e. (3-10C)carbocyclyl) and zero heteroatoms in the non-aromatic ring system. Suitably, carbocyclyl groups include (3-nC)cycloalkyl and (3-nC)cycloalkenyl. Exemplary embodiments include: cyclobutyl, cyclobutenyl, cyclopentyl, cyclopentenyl, cyclohexyl, cyclohexenyl, cyclohexadienyl, cycloheptyl, cycloheptenyl, cycloheptadienyl, cycloheptatrienyl, cyclooctyl, cyclooctenyl, bicyclo[2.2.1]heptanyl, bicyclo[2.2.2]octanyl, and the like.

Herein, the term "macrocyclyl", "macrocycle" or "macrocyclic" refers to macrocyclic rings, which are well known in the art. Such macrocyclic rings are suitably cyclic macromolecules or a macromolecular cyclic portions of a molecule. Suitably a macrocyclic ring has nine or more atoms within the ring. Suitably a macrocyclic ring has three or more internal electron-pair donating atoms. A macrocyclic ring is suitably a cyclic molecule able to co-ordinate to a central metal species (e.g. Mg). Examples include porphyrins.

Herein, the term "carbohydrate" is well understood in the art, and refers to compounds containing carbon, hydrogen, and oxygen only. Such compounds include esters, ketones, aldehydes, sugars, etc.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO2 groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

Wherever groups with large carbon chains are disclosed (e.g. (1-12C)alkyl, (1-8C)alkenyl, etc.), such groups may optionally be shortened, for instance containing a between 1 and 5 carbons (e.g. (1-5C)alkyl or (1-5C)alkenyl), or contain between 1 and 3 carbons (e.g. (1-3C)alkyl or (1-3C)alkenyl instead of (1-12C)alkyl or (1-8C)alkenyl).

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups; a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess telomerase inhibitory activity.

The present invention also encompasses compounds of the invention as defined herein which comprise one or more isotopic substitutions. For example, H may be in any isotopic form, including $^1H$, $^2H(D)$, and $^3H(T)$; C may be in any isotopic form, including $^1C$, $^{13}C$, and $^{14}C$; and O may be in any isotopic form, including $^{16}O$ and $^{18}O$; and the like.

It is also to be understood that certain compounds of the formula I may exhibit polymorphism, and that the invention encompasses all such forms.

Compounds may exist in a number of different tautomeric forms and references to compounds include all such forms. For the avoidance of doubt, where a compound can exist in one of several tautomeric forms, and only one is specifically described or shown, all others are nevertheless embraced by the definition of the compound. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

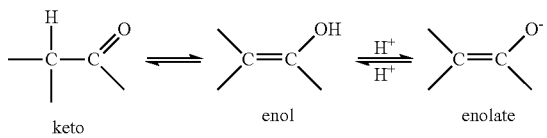

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

Herein, the term "particle size" or "pore size" refers respectively to the length of the longest dimension of a given particle or pore. Particle and pore sizes may be measured using methods well known in the art, including a laser particle size analyser and/or electron microscopes (e.g. transmission electron microscope, TEM, or scanning electron microscope, SEM).

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be understood by the skilled person that the compounds of the invention can be isolated and purified using techniques well known in the art. This may include an appropriate work-up procedure (optionally including quenching, pH adjustment, washes, drying, etc.). This may include concentration (e.g. in vacuo), recrystallisation, chromatography (whether standard or reverse-phase). Purity may be verified by techniques well known in the art.

It will be understood that any of the aforementioned general points regarding the synthesis of a compound may suitably also apply mutatis mutandis to other compounds and/or methods of the invention.

In the context of the invention, a "synthetic equivalent" is well understood by those skilled in the art, especially in the art of retrosynthesis, as a reference to a compound (or compounds) corresponding with a given "synthon" (E. J. Corey, *Pure App. Chem.*, 1967, 14: 30-37). Any given synthon may have a plurality of synthetic equivalents and, as such, a given first synthetic equivalent may be considered a synthetic equivalent of a second synthetic equivalent, though each of the two synthetic equivalents naturally correspond to a common synthon. As will be appreciated by those skilled in the art, a synthon is (typically) a hypothetical structural unit, fragment, or synthetic building block relating to a potential synthetic operation (E. J. Corey, "Robert Robinson Lecture. Retrosynthetic thinking-essentials and examples", *Chem. Soc. Rev.*, 1988, 17: 111-133). In the context of the present invention, alternative synthetic equivalents of any given compound or synthon are suitably independently transformable into an identical compound, be it into the given compound itself or most suitably a derivative (or post-reacted form) thereof. However, the skilled person will readily appreciate that transforming alternative synthetic equivalents into an identical compound may require a different process, and potentially a different number of synthetic steps. In the context of the invention, both starting materials and products may be designated by reference to a corresponding synthetic equivalent thereof, since it will be understood that any two synthetically equivalent starting materials may be ultimately transformed into an identical product or into a product which may thereafter be transformed into an identical product. Synthetic equivalents may be particularly relevant in the context of protecting groups, which may be transiently incorporated into part of the molecular structure of a compound (especially a part of said molecule which may be vulnerable or sensitive during processing) in order that they can be removed once having served their protective function.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The method(s) of the invention may therefore comprise, at any stage (including intermediates) though most suitably after a final synthetic step, optionally, and if necessary:
 (a) removing any protecting groups present;
 (b) converting the compound into another compound; and/or
 (c) forming an acceptable salt thereof.

General Methodology and Advantages of the Invention

The present invention contributes to the art a new class of stabilised porous materials (collapsible substrates whose porous structure and/or molecular cavities are stabilised through the judicious introduction of "molecular ties" which serve to inhibit or prevent pore-collapse which may otherwise occur) which, once formed, may be used as sorbents, for instance, for sorbing pollutants or for selectively sorbing a desired substance (e.g. $CO_2$ from a mixture of exhaust gases, to facilitate "carbon capture").

Furthermore, in a somewhat surprising development, the inventors serendipitously discovered that their pore-stabilisation technology (i.e. using molecular ties to stabilise previously unstable collapsible substrates) could be further exploited via a "dual sorption" process in which collapsible substrates (i.e. as yet unstabilised) capture gaseous molecular tie compounds both chemically (i.e. through chemisorptions involving molecular tie formations which produce stabilised porous materials from their corresponding unstabilised collapsible substrate) and physically (i.e. through physisorption involving the diffusion and ultimate adsorption/capture of molecular tie compounds within the pores).

For instance, collapsible substrates of the invention can be used to sorb gaseous formaldehyde (which serves as a tie molecule), even at relatively low partial pressures of formaldehyde—having previously used relatively concentrated solution-phase conditions to generate formaldehyde-derived molecular ties, such a finding was counterintuitive. Such collapsible substrates can, in some cases, absorb significantly more (e.g. ×20) formaldehyde than the best-performing existing technologies, such as polyacrylonitrile-based carbon fibre. Furthermore, the retention of formaldehyde by such porous materials is typically far superior to widely-used activated carbon-based materials, especially under humid conditions and/or elevated temperatures where activated carbon materials will liberate its adsorbed substrates in accordance with standard physisorption behaviour. The strong retention of sorbable substrates within the porous materials of the invention is thought not merely to be a function of the chemisorption but also enhanced physisorption brought about by the chemisorption. As such, synergistic effects appear to be at play given the high decomposition temperatures observed with respect to these sorption complexes. Finally, the inventors have noted that many of the sorbent materials of the invention exhibit much higher selectivity compared to their activated carbon counterparts.

Prior to the advent of the present invention, a wide range of transiently-porous materials were largely unviable as sorbent materials owing to their propensity to collapse upon pore vacation (e.g. following desolvation). As such, recent progress in the provision of chemically-stabilised porous materials (e.g. through the reduction of organic imine cages to address the inherent hydrolytic and acid/base instability of the imine moieties) was somewhat offset by the disappointing discovery that such chemical stabilisation often results in physical destabilisation (typically due to the inevitable conformation flexibility and freedom introduced upon converting a number sp2 carbon centres to sp3 centres when imines are reduced to their corresponding amines).

The present invention now allows these previously-unviable sorbent materials to be transformed into extremely viable and useful sorbent materials which are both physically and chemically stable. In particular, a number of the porous sorbent materials provided by the present invention are able to withstand both high and low pHs, which extends their utility markedly. The porous sorbent materials of the invention also typically withstand a range of temperatures (from low to high) without risk of damage or collapse. Moreover, the porous sorbent materials of the invention exhibit better solvent stability than many porous materials of the prior art. Furthermore, using the principles of the present invention and the guidance set forth herein, the skilled person can judicious apply the present invention to modify pore size, modify pore hydrophilicity/hydrophobicity, and/or pore-selectivity for particular sorbable substrates.

The benefits of the invention may be combined with those of existing technologies, for instance, by forming mixtures comprising the materials of the invention and one or more existing materials (e.g. zeolites, other sorbent materials).

The present invention has a wide range of applications, as discussed elsewhere herein, and can be utilised in environments which would have been previously too hostile for the kind of porous materials concerned.

Stabilizing a Collapsible Substrate

The present invention provides a method of stabilising a collapsible substrate, suitably as defined herein. The collapsible substrate (i.e. unstabilised precursor) suitably comprises at least one set (or pair) of distinct reactive moieties. The method suitably comprises reacting the collapsible substrate with a "molecular tie" compound, suitably reacting the at least one set (or pair) of distinct reactive moieties with said molecular tie compound. Such a reaction suitably causes the at least one set (or pair) of distinct reactive moieties within the collapsible substrate to become mutually interlinked via a "molecular tie" linker derived from the molecular tie compound.

The present invention also provides a method of preparing a stabilised porous material by the aforementioned method of stabilising a collapsible substrate. As such, the present invention also provides a stabilised porous material obtainable by said method. A stabilised porous material suitably comprises at least one set (or pair) of distinct reactive moieties interlinked via a "molecular tie" linker.

The method of preparing a stabilised porous material may additionally comprise a step of forming the collapsible substrate, as illustrated by way of example in Scheme 1.

Scheme 1 - Physical stabilisation and (optional) chemical stabilisation scheme

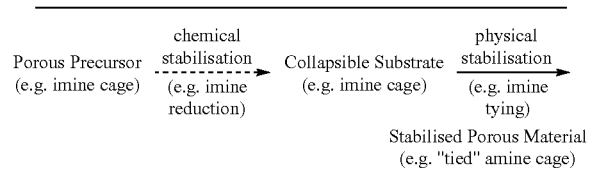

Chemically Stabilizing

The collapsible substrate (to be stabilised) is, in some cases, a chemically-stabilised collapsible substrate derived from a relatively-chemically-unstable porous precursor. In fact, the physical stability problems associated with the collapsible substrate may well be the by-product of a previous chemical stabilisation treatment of its porous precursor. For example, imine cage molecules (an example of a porous precursor) typically comprise a physically-stable but chemically-unstable porous structure (and/or molecular cavities). The relatively high physical stability of such imine cages is due to the imine cage molecules being rich in relatively conformationally-restricted sp2 carbon centres. The relatively low chemical stability (in particular hydrolytic instability, especially under acid and/or basic conditions) of such imine cages is a consequence of the reversibility of imine bond formation—i.e. imine bonds may undergo hydrolysis and thereby revert to their parent carbonyl (or carbonyl-derived) compounds.

As such, the methods of the invention (especially the methods of preparing a stabilised porous substrate) may include a step of forming the (relatively physically-unstable chemically-stable) collapsible substrate from a (relatively physically-stable but relatively chemically-unstable) porous precursor. For example, the method may comprise forming the collapsible substrate by transforming a relatively-chemically-unstable porous precursor into the (relatively-chemically-stable) collapsible substrate. This transformation suitably involves subjecting the porous precursor to a chemical reaction which yields are product which is more hydrolytically stable than the porous precursor. In a particular embodiment, where the porous precursor comprises imine moieties, the chemical reaction involves reducing at least some (preferably substantially all) of the imine moieties of the porous precursor to their corresponding amine moieties. Since the resulting amine bonds are hydrolytically more stable than the precursor imine bonds, the collapsible substrate product is considered to be more chemically stable than the precursor.

Such chemical stability (in particular hydrolytic stability) be may suitably sustained over a wide range of pHs, suitably from pH 1 to pH 13, suitably from pH1.5 to pH 12.5, suitably from pH 2 to 12, suitably from pH 4 to 10, suitably from pH 6 to 8. Such a high degree of chemical stabilisation allows the collapsible substrate to be theoretically used in a variety of contexts under a wide variety of conditions which might otherwise have proven hostile to the porous precursor. Therefore, such chemical stabilisation represents a promising step forward.

However, the physical stability problems arising from this chemical stabilisation process are readily addressed by the invention to furnish porous materials (e.g. amine cages) which are both physically and chemically stabilised and therefore usable in a variety of previously unviable contexts.

By way of example, Proton NMR may be used to determine chemical stability (—eg. less than 5% decomposition, as determined by proton NMR, when subjected to acidic environment at pH 1.7 for 12 days).

Physically Stabilizing

As explained in the Background Section of this specification, certain porous structures are prone to pore-collapse, especially when the pores themselves are vacated (e.g. during or after desolvation). Such pore-collapse is typically visible to an observer (either with the naked eye, a microscope, or appropriate microscope techniques such as SEM), who will usually note a change in shape and/or appearance of the relevant collapsible substrate.

Pore-collapse is often an inevitable result of a relatively high degree of conformational freedom within the molecules that make up the collapsible substrate. For instance, a porous substrate rich in sp2 carbon centres but relatively deficient in sp3 carbon centres is likely to be more rigid (owing to fewer degrees of conformational freedom) than a corresponding collapsible substrate that is deficient in sp2 carbons but rich in sp3 carbons. By way of Example, organic imine cages are physically more stable than their reduced amine counterparts. A conformational change lowering the energy of the overall system (be it with respect to the overall lattice/crystallisation energy of a bulk material, or with respect to conformational energies of individual molecules) is thermodynamically favoured and is likely to occur spontaneously where the conformational change is kinetically viable (e.g. when a pore has been vacated and/or when the porous structure has been subjected to certain conditions for a sufficient period of time). The methods of the present invention suitably transform collapsible substrates, which are prone (at least to an extent) to the aforementioned pore-collapse, into (relatively) stabilised porous materials. Such transformation generally increases either or both the kinetic and/or thermodynamic stability of the relevant collapsible substrate, suitably by restricting the conformation freedom of the molecules which make up the collapsible substrate (and ultimate stabilised porous material).

Stabilisation of the collapsible substrate suitably involves physical stabilisation thereof, and suitably at least involves physical stabilisation of the (potential) porous structure of the collapsible substrate (i.e. so that the porous structure, pore sizes, and pore shapes remain substantially unchanged over time, especially under certain conditions). Suitably physical stabilisation involves enhanced shape-persistence (i.e. where the physical shape and structure of the porous material persists for a longer period under a given set of common conditions). Most suitably, such physical stabilisation inhibits, prevents, or otherwise renders the stabilised porous material more resistant to pore collapse than its pre-stabilised collapsible substrate counterpart.

Such stabilisation of either or both of the porous structure and/or physical shape of a collapsible substrate is readily discernible by techniques well known in the art. For instance, a variety of comparative measurements (i.e. physical stability measurements—gas sorption experiments, single crystal and/or powder X-ray diffraction) between a stabilised porous material and its pre-stabilised collapsible substrate counterpart would deliver the necessary evidence of stabilisation.

However, it will be readily apparent to the skilled reader that in the context of the invention a collapsible substrate may be either collapsible (i.e. may collapse over time and/or under exposure to collapsing conditions) or already collapsed. As such, verifying a collapsible substrate as compared to a stabilised porous material may involve multiple tests, for instance:

i) A test upon a first sample of collapsible substrate and first sample of stabilised porous material to verify the relative pore size/volume per gram of both the collapsible substrate and corresponding stabilised porous material, for instance, through:
   a. Under identical conditions (e.g. 77K or 298K temperature, 1 Bar pressure), performing gas sorption analysis (e.g. using $N_2$, $H_2$, and/or $CO_2$ gas) for each sample and measuring the molar quantity of sorbed gas per gram of each substrate/material (e.g. mmol of gas per gram of tested substrate)—after pore-collapse, a collapsible substrate suitably exhibits lower gas sorption than the corresponding stabilised porous material;
   b. Calculating BET surface area (e.g. absolute or molar) from gas sorption isotherms (e.g. using $N_2$, $H_2$, and/or $CO_2$ gas)—after pore-collapse, a collapsible substrate suitably exhibits a lower BET surface area (absolute or molar) than the corresponding stabilised porous material;

ii) A test upon a second sample of collapsible substrate and second sample of stabilised porous material to verify initial collapsed state of the collapsible substrate and the relative physical stability of the two samples, for instance, through:
   a. Exposing each sample to stressing conditions (e.g. high temperature—e.g. 100° C. or higher, suitably 200° C. or higher) for a period of time (e.g. 12 hours, suitably 24 hours, suitably 48 hours) and examining any physical changes (e.g. naked-eye visible changes, microscopically visible changes, changes to XRPD measurements, changes in porosity as per tests of (i))—if the collapsible substrate does not change, it may be deemed already collapsed; if the collapsible substrate changes, it is pre-collapsed or partially-collapsed; a pre-collapsed collapsible substrate suitably changes more than the stabilised porous material.

Comparative collapsibility between a collapsible compound may be determined

Stability of Stabilised Porous Material

The stabilised porous material formed from the methods of the invention is suitably relatively physically stable (in terms of shape-persistence, pore-collapsibility) compared to the corresponding pre-tied collapsible substrate and, where applicable, is suitably relatively chemically stable (in terms of hydrolytic stability, especially under acidic or basic conditions) compared to any corresponding porous precursor from which the collapsible substrate may be formed.

Suitably the physical form/shape of the crystals, particles (e.g. especially where amorphous), and/or bulk of the stabilised porous material remains substantially unchanged or relatively less changed for longer than the corresponding collapsible substrate when stored under the same conditions (e.g. under a 1 bar atmosphere of air, at a relative humidity of at least 20%, suitably at least 50%) at temperature of at least 20° C., more suitably at least 50° C., more suitably at least 100° C. Suitably the physical form/shape of the crystals, particles (e.g. especially where amorphous), and/or bulk of the stabilised porous material remains (substantially unchanged or relatively less changed) for longer than the corresponding collapsible substrate either during or after drying under the same conditions (e.g. under vacuum at elevated temperature).

Suitably the stabilised porous material has greater chemical stability (e.g. hydrolytic stability) than any corresponding porous precursor when subject to the same stressing conditions (e.g. stirred in aqueous acid at pH3 or stirred in aqueous base at pH 11 at SATP).

Suitably the stabilised porous material is substantially hydrolytically stable (e.g. exhibiting less than 5 wt % decomposition, suitably less than 2 wt %, as adjudged by standard methods known in the art, such as HPLC, GC, etc.) after stirring in aqueous acid (at a pH between pH 1.5 and pH 4, suitably at pH1.7) for 1 day, suitably after 2 days, suitably after 5 days, suitably after 12 days. Suitably the stabilised porous material is substantially hydrolytically stable (e.g. exhibiting less than 5 wt % decomposition, suitably less than 2 wt %) after stirring in aqueous base (at a pH between pH 10 and pH 12.5, suitably at pH 12.3) for 1 day, suitably after 2 days, suitably after 5 days, suitably after 12 days. Suitably the stabilised porous material is substantially physically stable (in terms of shape/form, and or pore shape/form) when subjected to the same conditions. By contrast, suitably the collapsible substrate is less hydrolytically stable and/or physically stable under the same conditions. Likewise, suitably any porous precursor is less hydrolytically stable and/or physically stable under the same conditions.

Reacting

Reacting the collapsible substrate with a "molecular tie" compound suitably involves contacting the collapsible substrate with an appropriate molecular tie compound (see below), suitably in a solvent system, most suitably in a solvent system in which the molecular tie compound is dissolved, suitably in a solvent system in which both the molecular tie compound and the collapsible substrate are dissolved (or at least soluble).

In a particular embodiment, the solvent system is or comprises the molecular tie compound itself (i.e. where said compound is in a liquid state at the relevant temperature and pressure). In other embodiments, the solvent system does not in itself comprise the molecular tie compound, though the molecular tie compound may be dissolved within said solvent system.

Suitably the reaction takes place under anhydrous conditions or conditions under which water is only present within the reaction mixture at a concentration of less than or equal to 2 wt %, suitably less than or equal to 1 wt %, suitably less than or equal to 0.5 wt %, suitably less than or equal to 0.1 wt %. The reaction may proceed under acidic conditions, suitably mildly-acidic conditions or at a pH between 4.5 and 6.9. However, the reaction may proceed under (substantially) neutral conditions, for instance at a pH between 6.5 and 7.5.

However, the reaction may occur under moist, humid, or even aqueous conditions, especially where the molecular tie compound is formaldehyde. The reaction may be conducted within an aqueous solvent system, or alternatively within a solvent system comprising greater than 0.5 wt % water, suitably greater than 1 wt %, suitably greater than 2 wt % water.

In a particular embodiment, the reaction involves agitating a solution, emulsion, dispersion, or suspension (most preferably a solution) of the collapsible substrate and molecular tie compound optionally at an elevated temperature (i.e. a temperature higher than 30° C., suitably higher than 40° C., suitably higher than 60° C., though suitably less than 90° C., suitably less than 80° C.). In a particular embodiment, the product (stabilised porous material) precipitates or crystallises from the reaction mixture, from which it may be subsequently filtered.

Suitably, after isolating the stabilised porous material from the reaction mixture, the stabilised porous material is dried and/or fully or partially desolvated. Suitably the stabilised porous material is dried under vacuum and/or at a temperature of at least 50° C., suitably at least 70° C., suitably at about 80° C., though suitably less than 150° C., suitably less than 100° C.

Suitably the reaction causes at least one set (or pair) of distinct reactive moieties within the collapsible substrate to become mutually interlinked, suitably at least two sets (or pairs), more suitably at least three sets (or pairs), most suitably six sets (or pairs). Most suitably, distinct reactive moieties within the same molecule of the collapsible substrate react with a molecular tie compound to become mutually interlinked (i.e. via intramolecular links).

Suitably the reaction causes at least 10% of the sets (or pairs) of distinct reactive moieties to become mutually interlinked, suitably at least 20%, suitably at least 50%, more suitably at least 80%, more suitably at least 95%, and most suitably substantially all set (or pairs).

Suitably the reaction causes sufficient interlinking (tying) between distinct reactive moieties to furnish a physically and chemically stable material (suitably as defined herein) which remains suitably porous for the application in question. For instance, suitably the stabilised porous material is porous to hydrogen gas, is suitably porous to nitrogen gas, and/or is suitably porous to carbon dioxide. For example, the stabilise porous material may be suitably sorbent with respect to hydrogen gas, nitrogen gas, and/or carbon dioxide, or may be selectively sorbent of a particular gas, for instance, carbon dioxide.

Suitably, the molecular tying reaction comprises reacting a polyamine compound with a molecular tie compound under conditions which cause at least two reactive amine moieties within the polyamine compound to become interlinked via a molecular tie linker. Suitably the polyamine compound is a polyamine cage (suitably an organic polyamine cage), a polyamine macrocycle (suitably an organic polyamine macrocycle), and/or a polyamine framework (suitably an organic framework, e.g. covalent organic framework). In a particular embodiment, the polyamine compound is an organic polyamine cage.

Suitably at least one set (or pair) of distinct reactive moieties within the collapsible substrate are themselves interlinked, suitably interlinked by between 1 and 6 atoms (suitably carbon atoms), suitably between 1 and 4 atoms, more suitably between 2 and 3 atoms, most suitably between 2 and 3 (optionally substituted or branched) carbon atoms. Suitably the at least two reactive amine moieties are themselves interlinked within the "collapsible" polyamine compound, suitably interlinked by between 1 and 6 atoms (suitably carbon atoms), suitably between 1 and 4 atoms, more suitably between 2 and 3 atoms, most suitably between 2 and 3 (optionally substituted or branched) carbon atoms. As such, the molecule ties linkers suitably for a bridge between these (sets of) reactive moieties.

Suitably the molecular structures of both the collapsible substrate and molecular tie compound are selected to be mutually complementary for achieving the aforementioned structures described in respect of the resulting stabilised porous materials. For instance, the reactants may be selected to enable formation of one or more 5-8 membered (heterocyclic) rings each comprising a respective set of distinct reactive moieties (e.g. pair of proximal amine moieties) and corresponding molecular tie linker. In a particular embodiment, the reactants are selected to enable formation of one or more 5-8 membered (heterocyclic) rings.

Chemical Structure of Moieties and Compounds

The collapsible substrate suitably is or comprises a collapsible compound, and the stabilised porous material suitably is or comprises a stabilised compound.

The collapsible compound suitably comprises one or more reactive units, each of which units may comprise one or more (preferably two or more, most preferably two) distinct reactive moieties (e.g. amine moieties). The collapsible compound suitably comprises a plurality of the reactive units, suitably such that the collapsible compound comprises at least six reactive moieties (e.g. amine groups), suitably at least ten, suitably at most forty, suitably at most twenty, most suitably twelve reactive moieties. The reactive units themselves are suitably covalently linked, suitably via an interlinking linker unit.

The reactive units may be linked together so as to form:
an open chain, albeit optionally a chain containing one or more ring systems (e.g. carbocyclic, aryl, heterocyclic, heteroaryl) optionally as member(s) of the reactive units, the linker(s), or as optional substituents thereof;
a macrocycle, again optionally containing one or more ring systems as per above; and/or
a cage, again optionally containing one or more ring systems as per above.

The molecular tie compound suitably comprises one or more moieties (e.g. carbonyl moieties). The molecular tie compound suitably comprises a single reactable moiety (e.g. carbonyl), though the single reactable moiety may suitably be capable of reacting with two reactive moieties of the collapsible compound to produce a molecular tie (or bridge) between said two reactive moieties.

Suitably, the reaction between the collapsible compound and molecular tie compound comprises:
reacting the collapsible compound (or a synthetic equivalent thereof) comprising one or more reactive units, with a molecular tie compound (or a synthetic equivalent thereof) comprising one or more reactable units, to form a stabilised compound (or precursor thereto—e.g. if subsequent deprotection or other transformation steps are required to furnish a final product) comprising one or more tied units;
wherein:
the one or more reactive units of the collapsible compound comprise one or more (preferably two or more, most preferably two) distinct reactive moieties (e.g. amine);
the one or more reactable units of the molecular tie compound comprise one or more reactable moieties (e.g. carbonyl, protected carbonyl, dihalo); and
the one or more tied units of the stabilised compound comprise one or more moieties characterised by the product of a reaction between the reactive unit(s) of the collapsible substrate and the molecular tie compound.

Suitably the corresponding reactive and reactable moieties are predisposed to react together (to form a covalent linkage there between) under appropriate conditions. Suitably one of either the reactive or reactable moieties is electrophilic whilst the other of either the reactive or reactable moieties is nucleophilic. Suitably a single reactable moiety reacts with at least two (preferably two) reactive moieties. A single tied unit is suitably formed by a single molecular tie molecule (or a single reactable moiety of a single molecular tie molecule) reacting with at least two (preferably only two) reactive moieties of a collapsible substrate.

The stabilised porous material therefore suitably comprises a compound ("stabilised compound") including one or more tied units, where each tied unit suitably corresponds directly with a post-reacted form of a given reactive unit of the collapsible compound. As such, the tied units are suitably covalentiy linked (as per the corresponding collapsible compound), suitably via an interlinking linker unit (suitably the same linker as defined in relation to the collapsible compound). The stabilised compound suitably comprises a plurality of the tied units, suitably such that the stabilised compound comprises at least three tied units, suitably at least five, suitably at most twenty, suitably at most ten, most suitably six tied units. Moreover, the tied units are suitably linked together in the same manner as the reactive units of the original collapsible compound, i.e. to form:
an open chain, albeit optionally a chain containing one or more ring systems (e.g. carbocyclic, aryl, heterocyclic, heteroaryl) optionally as member(s) of the tied units, the linker(s), or as optional substituents thereof;
a macrocycle, again optionally containing one or more ring systems as per above; and/or
a cage, again optionally containing one or more ring systems as per above.

The number and chemical structure of the reactive units of the collapsible compound and/or the tied units of the stabilised compound may be readily varied by those skilled in the art by making appropriate synthetic modifications. Such parameters may be desirably varied in order to change pore size, pore selectivity (in terms of selectivity for particular guest compounds), and/or other properties. Likewise, the chemical structure (especially the size or molecular weight) of the molecular tie compound may also be readily varied, again to affect the pore size, pore selectivity, and/or other properties of the ultimate stabilised compound. Thus the collapsible compound (and where relevant its porous precursor) and molecular tie compound are suitably judiciously chosen to provide, after the aforementioned reaction, a stabilised compound (and corresponding stabilised porous material) that is more stable than the collapsible compound and which has at least a sufficient degree of porosity for the desired application (e.g. pores of a sufficient shape and size so that the stabilised compound may serve as a host for a selected guest compound).

Suitably the moieties of the collapsible compound other than the "reactive moieties" are (substantially) inert, suitably inert towards any reactable moieties of the molecular tie compound, suitably inert to both electrophiles and nucleophiles, especially under the prevailing reaction conditions.

Suitably the moieties of the molecular tie compound other than the "reactable moieties" are (substantially) inert, suitably inert towards any reactive moieties of the collapsible compound, suitably inert to both electrophiles and nucleophiles, especially under the prevailing reaction conditions.

Suitably any linker(s), or substituents thereof, of the collapsible compound are (substantially) inert, suitably inert towards any reactive moieties of the collapsible compound or any reactable moieties of the molecular tie compound, suitably inert to both electrophiles and nucleophiles, especially under the prevailing reaction conditions.

In a particular embodiment, the reaction comprises: reacting a collapsible compound (or a synthetic equivalent thereof) comprising one or more reactive units defined by Formula A:

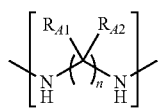

Formula A with a molecular tie compound (or a synthetic equivalent thereof) defined by Formula B:

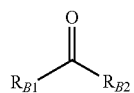

Formula B wherein:

n is an integer between 1 and 4;

each $R_{A1}$ and $R_{A2}$ group is independently hydrogen or an optionally substituted substituent group, wherein any pair of $R_{A1}$ and $R_{A2}$ groups are optionally joined together to form a carbocyclic, heterocyclic, aryl, or heteroaryl ring;

each $R_{B1}$ and $R_{B2}$ group is independently hydrogen or an optionally substituted substituent group, wherein any pair of $R_{B1}$ and $R_{B2}$ groups are optionally joined together to form a carbocyclic, heterocyclic, aryl, or heteroaryl ring;

to produce a stabilised porous material comprising one or more tied units defined by Formula C:

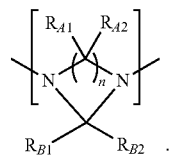

Formula C

The units of Formula's A and C are represented in divalent form, as donated by the bonds intersected by square brackets (these bonds may be considered as radicals, or "connectable bonds"). These units may be considered repeat units where the relevant compounds comprise two or more of said units (which is generally the case). As explain in detail below, a collapsible substrate and its corresponding stabilised porous material may suitably respectively comprise a plurality of units of Formula A and Formula C linked together (suitably to form an open chain, macrocyclic, or caged compound/molecule) via their "connectable bonds", suitably via an intervening linker. Such a linker may link together two or more units of Formula A and/or C, and in some embodiments links three such units. As such, said linker is suitably polyvalent (e.g. divalent, trivalent).

In accordance with the invention, the aforementioned units of Formula A, B, and C, and by extension their corresponding compounds (or synthetic equivalents thereof) and also any linkers therebetween, may, unless otherwise stated, have any structure defined herein wherein each of n, $R_{A1}$, $R_{A2}$, $R_{B1}$, $R_{B2}$ has any of the meanings defined hereinbefore or in the paragraphs that follow:

(1) n is an integer between 2 and 3;
(2) n is 2;
(3) each $R_{A1}$ and $R_{A2}$ is independently selected from hydrogen or any inert group (e.g. inert towards electrophiles, suitably towards carbonyls, suitably inert in relation to the molecular tie compound), including inert groups wherein an $R_{A1}$ and an $R_{A2}$ are linked so that together they form a carbocyclic, aryl, heterocyclic, or heteroaryl ring, suitably wherein each $R_{A1}/R_{A2}$ pair (i.e. attached to the same carbon atom) has a collective molecular weight less than 200, suitably less than 100, suitably less than 70;
(4) $R_{A1}$ and $R_{A2}$ are independently selected from the group consisting of hydrogen, (1-2C)alkyl, or $R_{A1}$ and $R_{A2}$ are linked such that together they form a carbocyclic ring;
(5) $R_{A1}$ and $R_{A2}$ are linked such that together they form a (3-8C)cycloalkyl ring;
(6) $R_{A1}$ and $R_{A2}$ are linked such that together they form a cyclohexane ring;
(7) each $R_{B1}$ and $R_{B2}$ is independently selected from hydrogen or any inert group (e.g. insert towards nucleophiles, suitably towards amines, suitably inert in relation to the collapsible compound), including inert groups wherein an $R_{B1}$ and an $R_{B2}$ are linked so that together they form a carbocyclic, aryl, heterocyclic, or heteroaryl ring, suitably wherein each $R_{B1}/R_{B2}$ pair (i.e. attached to the same carbon atom) has a collective molecular weight less than 100, suitably less than 50, suitably less than 31, suitably less than 5;
(8) $R_{B1}$ and $R_{B2}$ are independently selected from the group consisting of hydrogen, (1-3C)alkyl, or $R_{B1}$ and $R_{B2}$ are optionally linked such that together they form a carbocyclic, heterocyclic, aryl, or heteroaryl ring;
(9) $R_{B1}$ and $R_{B2}$ are independently selected from the group consisting of hydrogen and methyl;
(10) $R_{B1}$ and $R_{B2}$ are both methyl;
(11) $R_{B1}$ and $R_{B2}$ are both hydrogen;
(12) the collapsible compound and/or the stabilised compound comprise at least three units of Formula A and/or Formula C respectively;
(13) the collapsible compound and/or the stabilised compound comprise at least five units of Formula A and/or Formula C respectively;
(14) the collapsible compound and/or the stabilised compound comprise at most twenty units of Formula A and/or Formula C respectively, more suitably at most ten units of Formula A and/or Formula C respectively;
(15) the collapsible compound and/or the stabilised compound comprise six units of Formula A and/or Formula C respectively;
(16) the units of Formula A and/or Formula C are covalently linked, directly or indirectly, together (suitably in series and/or parallel, i.e. straight chain or branched) to form an open chain, a macrocycle, and/or a cage structure;

(17) the units of Formula A and/or Formula C are covalently linked together, directly or indirectly, to form a macrocycle and/or a cage structure;
(18) the units of Formula A and/or Formula C are covalently linked together, directly or indirectly, to form a cage structure (e.g. an organic cage molecule);
(19) the units of Formula A and/or Formula C are covalently linked together via between 1 and 8 intervening atoms (suitably carbon atoms), suitably between 4 and 6 intervening atoms (suitably carbons), most suitably 5 intervening carbon atoms;
(20) the units of Formula A and/or Formula C are covalently linked together via an intervening linker of Formula -$L_1$-;
(21) -$L_1$- is a polyvalent group providing the aforementioned number of intervening atoms between neighbouring units of Formula A and/or Formula C;
(22) -$L_1$- is selected from the group consisting of a polyvalent hydrocarbon (straight chain or branched), a polyvalent carbocycle, a polyvalent heterocycle, a polyvalent arene, a polyvalent heteroarene, a polyvalent mono-/poly-hydrocarbyl-carbocycle, a polyvalent mono-/poly-hydrocarbyl-heterocycle, a polyvalent mono-/poly-hydrocarbyl-arene, and a polyvalent mono-/poly-hydrocarbyl-heteroarene (where mono-/poly-indicates that the relevant ring system respectively comprises one or a plurality of hydrocarbyl substituents);
(23) -$L_1$- is selected from the group consisting of a polyvalent (1-8C)alkane, a polyvalent (2-8C)alkene, a polyvalent (3-8C)cycloalkane, a polyvalent mono-/poly-[(1-8C)alkyl]-(3-8C)cycloalkane, a polyvalent (3-8C)cycloalkene, a polyvalent mono-/poly-[(1-8C)alkyl]-(3-8C)cycloalkene, a polyvalent heterocycle, a polyvalent mono-/poly-[(1-8C)alkyl]-heterocycle, a polyvalent arene, a polyvalent mono-/poly-[(1-8C)alkyl]-arene, a polyvalent heteroarene, and a polyvalent-mono-/poly-[(1-8C)alkyl]-heteroarene;
(24) -$L_1$- is selected from the group consisting of a polyvalent (4-6C)alkane, a polyvalent (4-6C)alkene, a polyvalent (5-6C)cycloalkane, a polyvalent mono-/poly-[(1-2C)alkyl]-(5-6C)cycloalkane, a polyvalent (5-6C)cycloalkene, a polyvalent mono-/poly-[(1-2C)alkyl]-(5-6C)cydoalkene, a polyvalent heterocycle, a polyvalent mono-/poly-[(1-2C)alkyl]-heterocycle, a polyvalent arene, a polyvalent mono-/poly-[(1-2C)alkyl]-arene, a polyvalent heteroarene, and a polyvalent mono-/poly-[(1-2C)alkyl]-heteroarene;
(25) -$L_1$- is selected from the group consisting of a polyvalent poly-[(1-2C)alkyl]-(5-6C)cycloalkane, a polyvalent poly-[(1-2C)alkyl]-(5-6C)cycloalkene, a polyvalent poly-[(1-2C)alkyl]-heterocyclyl, a polyvalent poly-[(1-2C)alkyl]-arene, and a polyvalent poly-[(1-2C)alkyl]-heteroarene;
(26) -$L_1$- is a polyvalent poly-[(1-2C)alkyl]-arene;
(27) -$L_1$- is a trivalent tri-[(1-2C)alkyl]-arene
(28) -$L_1$- is selected from the group consisting of benzene-trimethylene;
(29) -$L_1$- is selected from the group consisting of benzene-1,3,5-trimethylene;
(30) the molecular tie compound is selected from formaldehyde and/or acetone;
(31) the molecular tie compound is formaldehyde;
(32) Any one or more of the $R_{A1}$, $R_{A2}$, $R_{B1}$, $R_{B2}$, and -$L_1$- groups may be optionally substituted (suitably so long as the relevant collapsible and molecular tie molecules react together to produce a porous material whose physical structure is more stable than that of the collapsible substrate, and whose pores are sufficient usable to accommodate one or more guest compounds);
(33) any CH, $CH_2$ or $CH_3$ group within any of the aforementioned $R_{A1}$, $R_{A2}$, $R_{B1}$, $R_{B2}$ and -$L_1$- groups optionally bears on each said CH, $CH_2$ or $CH_3$ group one or more substituent groups selected from halogeno, hydroxy, mercapto, amino, cyano, carboxy, carbamoyl, ureido, (1-3C)alkyl, hydroxy(1-3C)alkyl, (1-3C)alkoxy, halo(1-3C)alkoxy, (1-3C)alkylthio, (1-3C)alkylamino, and di-[(1-3C)alkyl]amino;
(34) any CH, $CH_2$ or $CH_3$ group within any of the aforementioned $R_{A1}$, $R_{A2}$, $R_1$, $R_{B2}$ and -$L_1$- groups optionally bears on each said CH, $CH_2$ or $CH_3$ group one or more substituent groups selected from halogeno, hydroxy, mercapto, amino, methyl, hydroxymethyl, methoxy, trifluoromethoxy, trichloromethoxy, methylthio, methylamino, and dimethylamino;
(35) all CH, $CH_2$ or $CH_3$ group within any of the aforementioned $R_{A1}$, $R_{A2}$, $R_{B1}$, $R_{B2}$ and -$L_1$- are unsubstituted;

In a particular embodiment $R_{A1}$, $R_{A2}$ and -$L_1$- are selected such that the collapsible compound comprises a plurality of reactive units of Formula $A_1$, each reactive unit being indirectly linked (through their connectable bonds denoted by square brackets) to a neighbouring distinct reactive unit via an intervening linker unit of Formula $A_{1L}$ (through connectable bonds thereof denoted again by square brackets):

$$\text{Formula } A_1$$

wherein Ring A is a carbocyclic, aryl, heterocyclic, or heteroaryl ring;

$$\text{Formula } A_{1L}$$

wherein Ring L is a polyvalent hydrocarbon (straight chain or branched), a polyvalent carbocycle, a polyvalent heterocycle, a polyvalent arene, a polyvalent heteroarene, a polyvalent mono-/poly-hydrocarbyl-carbocycle, a polyvalent mono-/poly-hydrocarbyl-heterocycle, a polyvalent mono-/poly-hydrocarbyl-arene, or a polyvalent mono-/poly-hydrocarbyl-heteroarene (it should be implicit from this specification that the linker of Formula $A_{1L}$ bonds to a reactive unit of Formula A, at the indicated square brackets for both species, though it should also be implicit that in respect of the linker the relevant connectable bond or radical may stem from the core ring structure or, where applicable, from one of the hydrocarbyl substituents of the core ring);

wherein any of the groups of Formula $A_1$ or $A_{1L}$ are optionally substituted as defined herein. In this embodiment, the collapsible compound suitably comprises units of Formula $A_1$ and $A_{1L}$ respectively in a molar ratio of 3:2 (e.g. 6 units of $A_1$ and 4 pf $A_{1L}$). In adaptations of this embodiment, Ring A may be replaced with a (2-3C)alkylene group between the relevant amine moieties to produce an alkylenediamine. A corresponding stabilised compound suitably has the same structure as the collapsible compound except that at least one (suitably at least two, suitably six, suitably all) reactive unit(s) of Formula $A_1$ becomes a tied unit of Formula $C_1$:

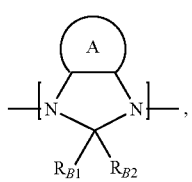

Formula $C_1$ wherein $R_{B1}$ and $R_{B2}$ have any definition given herein, though most suitably both are hydrogen or both are methyl. Suitably, where both $R_{B1}$ and $R_{B2}$ are hydrogen (i.e. derived from a formaldehyde molecular tie compound) two or more, preferably all reactive units of the collapsible compound become tied units. Suitably, where both $R_1$ and $R_{B2}$ are methyl (i.e. derived from an acetone molecular tie compound) only one reactive unit of the collapsible compound becomes a tied unit.

In a particular embodiment $R_{A1}$, $R_{A2}$ and -$L_1$- are selected such that the collapsible compound comprises at least three reactive units of Formula $A_1$, each reactive unit being indirectly linked to a neighbouring distinct reactive unit via an intervening linker unit of Formula $A_{1L}$:
wherein:
  Ring A is a (5-6C)cycloalkane; and
  Ring L is a polyvalent poly-[(1-2C)alkyl]-(5-6C)cycloalkane, a polyvalent poly-[(1-2C)alkyl]-(5-6C)cycloalkene, a polyvalent poly-[(1-2C)alkyl]-heterocyclyl, a polyvalent poly-[(1-2C)alkyl]-arene, or a polyvalent poly-[(1-2C)alkyl]-heteroarene;
wherein any of the groups of Formula $A_1$ or $A_{1L}$ are optionally substituted as defined herein.

In a particular embodiment $R_{A1}$, $R_{A2}$-$L_1$-, Ring A, and Ring L are selected such that the collapsible compound comprises a plurality of reactive units of Formula $A_2$, each reactive unit being indirectly linked to a neighbouring distinct reactive unit via an intervening linker unit of Formula $A_{2L}$:

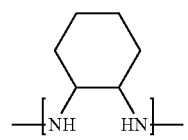

Formula $A_2$

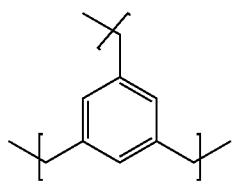

Formula $A_{2L}$ wherein any of the groups of Formula $A_2$ or $A_{2L}$ are optionally substituted as defined herein, though most suitably they are unsubstituted. In this embodiment, the collapsible compound suitably comprises units of Formula $A_2$ and $A_{2L}$ respectively in a molar ratio of 3:2 (e.g. 6 units of $A_2$ and 4 pf $A_{2L}$). In adaptations of this embodiment, the cyclohexane ring may be replaced with a (2-3C)alkylene group between the relevant amine moieties to produce an alkylenediamine and optionally the benzene ring of the linker may be replaced with a heteroarene ring. A corresponding stabilised compound suitably has the same structure as the aforementioned collapsible compound except that at least one (suitably at least two, suitably six, suitably all) reactive unit(s) of Formula $A_2$ becomes a tied unit of Formula $C_2$:

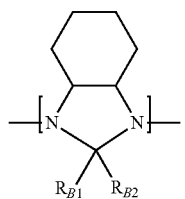

Formula $C_2$ wherein RB, and $R_{B2}$ have any definition given herein, though most suitably both are hydrogen or both are methyl. Suitably, where both $R_{B1}$ and $R_{B2}$ are hydrogen (i.e. derived from a formaldehyde molecular tie compound) two or more, preferably all reactive units of the collapsible compound become tied units. Suitably, where both $R_1$ and $R_{B2}$ are methyl (i.e. derived from an acetone molecular tie compound) only one reactive unit of the collapsible compound becomes a tied unit.

In a particular embodiment, the collapsible compound is defined by Formula A3:

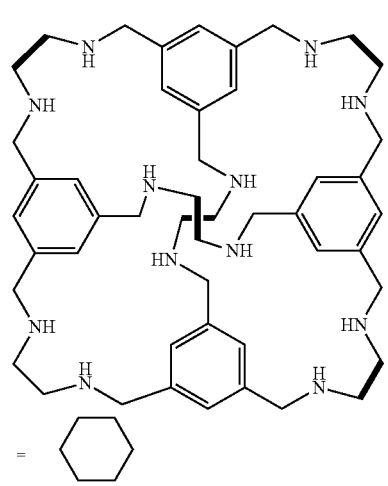

Formula A3

Suitably, a stabilised compound of the invention has a structure corresponding directly with (or based directly upon) any of the embodiments and/or definitions given herein in relation to the collapsible compound, with two or more of the reactive moieties of the collapsible compound having reacted with a molecular tie compound to form a corresponding molecular tie between said reactive moieties. This is self-evident from above where the reactive units of Formula A correspond directly with the tied units of Formula C. Stabilised compounds suitably also comprise the same linkers, which are suitably joined to reactive/tied units in the same manner, as per their corresponding collapsible compounds. Suitably each reactive unit of the collapsible compound comprises two reactive moieties. Suitably any, some, or all molecular ties between reactive moieties are between two reactive moieties within the same reactive unit. As such, suitably the stabilised compound is its corresponding collapsible compound with one or more reactive units having been transformed into tied units. The stabilised compound may comprise both reactive units and tied units, so long as at least one tied unit exists. In preferred embodiments, the stabilised compound comprises two or more tied units. In a particular embodiment, the stabilised compound comprises two or more, suitably three or more, suitably five or more, suitably six tied units and is suitably (substantially) free of reactive units (i.e. all the reactive units are reacted to produce tied units).

In an embodiment, a stabilised compound corresponding with (formed from) the collapsible compound of Formula A3 (which has six reactive units, each with two reactive amine moieties) has one tied moiety and five reactive moieties where $R_{B1}$ and $R_{B2}$ are both methyl (i.e. using an acetone molecular tie compound). In an alternative embodiment, a stabilised compound corresponding with (formed from) the same collapsible compound of Formula A3 has six tied moiety and zero reactive moieties where $R_{B1}$ and $R_{B2}$ are both hydrogen (i.e. using a formaldehyde molecular tie compound)—as such all six ethylenediamine units become tied units. In a particular embodiment, the stabilised compound is defined by Formula C3:

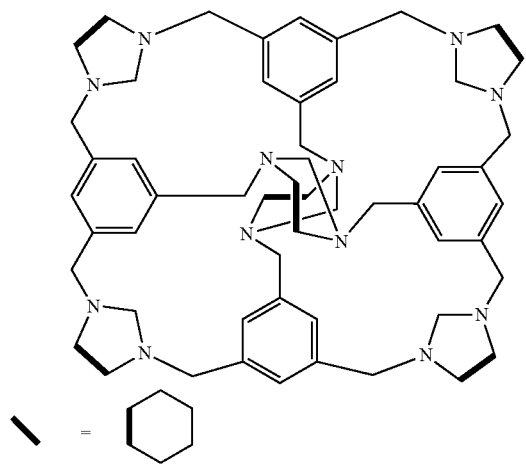

Formula C3

In respect of all the aforementioned embodiments, the relevant collapsible compound(s) is optionally formed by reduction of a corresponding porous precursor compound (i.e. imine compound), for instance, where each amine moiety of a reactive unit translate to a nitrogen which forms a direct imine bond with the ajoining carbon atom of the linker to which it is attached. By way of example, the collapsible compound of Formula A3 may be formed from the corresponding porous imine compound of Formula D3:

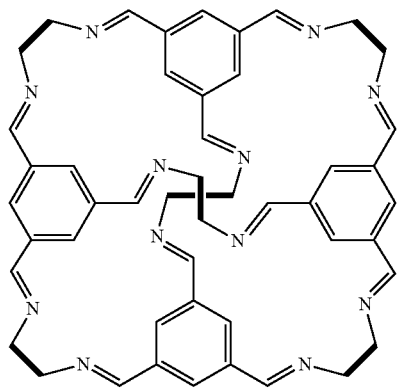

wherein the bold lines match those of the Formula A3.

Collapsible Substrate (i.e. Pre-Stabilised Precursor)

The present invention provides a collapsible substrate as defined herein. For instance, the collapsible substrate may comprise or correspond to a collapsible substrate/compound as described in relation to the method of stabilising a collapsible substrate, and may comprise reactive units of Formula A (or relevant sub-definitions thereof) and optionally linkers, for instance, of Formula $L_1$ (or sub-definitions thereof). Suitably the collapsible substrate comprises a collapsible compound as defined herein, which suitably comprises one or more reactive units covalently linked via an interlinking linker unit, wherein each reactive unit may comprise one or more distinct reactive moieties (e.g. amine moieties).

The collapsible substrate may be in a non-collapsed state, a partially-collapsed state, or a (substantially) collapsed state. The collapsible substrate may exhibit a non-collapsed state where the pores thereof are host to a sufficient quantity of guests—e.g. where the collapsible substrate is solvated (e.g. with methanol or water). Likewise, a partially-collapsed state may be exhibited under the same circumstances but where a lower quantity of guests are present. A collapsed state is generally exhibited where the collapsible substrate is (substantially) free of guests or has insufficient to sustain a non-collapsed structure.

A collapsible substrate may be transformed into a collapsed state from a partially-collapsed state or non-collapsed state under appropriate conditions which the skilled person may readily deduce in view of this disclosure. Suitably the collapsible substrate is transformed from a partially-collapsed state or non-collapsed state into a collapsed state under stressing conditions, for instance, when exposed to elevated temperatures (e.g. 100° C. or higher, 200° C. or higher) for a sufficient period of time (e.g. 12 hours, 24 hours, 48 hours). Such conditions will generally desolvate any solvate pores and allow the pore structure to collapse.

In its collapsed state, the collapsible substrate suitably does not undergo any further physical changes (e.g. in terms of its appearance, porous structure, XRPD, gas adsorption) under relevant stressing conditions (e.g. at 100° C. temperature at 1 Bar).

In its collapsed state, the collapsible substrate suitably has a pore volume (and/or BET surface area) per gram (and/or per mole) that is lower than that of the corresponding stabilised porous material (e.g. with molecular ties). As such, a collapsible substrate may be "collapsed" (e.g. by heat, or another suitable method, e.g. dissolution/precipitation) to formally determine its role as the collapsible substrate.

The collapsible compounds of the invention may be porous and even crystalline when in solvated form, but is suitably non-porous or less porous and suitably non-crystalline (or amorphous) when desolvated. The present invention therefore seeks to instil long-term porosity where the pores are vacant (and therefore ready to partake in host-guest chemistry).

The physical instability issues associated with such collapsible compounds are documented elsewhere herein, and an aim of the invention is certainly the stabilisation of such compounds to allow them to be used in host-guest chemistry (for instance, as sorbates).

However, the reversibility of certain molecular tying reactions (e.g. where acetone is used as the molecular tie compound) provides a new means of purifying such collapsible compounds. For instance, a collapsible compound may be initially stabilised as defined herein (e.g. through molecular tying) to produce a corresponding crystalline stabilised compound which is highly pure due to its inherent crystallinity (in contrast to the collapsible compounds which tend to be amorphous, at least when desolvated, and thus more difficult to purify via crystallisation), and thereafter converted back into a purified form of the collapsible compound (e.g. by hydrolytic cleavage of molecular ties). Such purifications are particular successful where acetone (or other molecular tie compounds which bind more reversibly than formaldehyde) is used as the molecular tie compound.

As such, the present invention also provides a method of purifying a collapsible substrate, the method comprising preparing a stabilised porous material or stabilising a collapsible substrate as defined herein to transform the collapsible substrate into a stabilised porous material; purifying the stabilised porous material to provide a purified stabilised porous material; and thereafter regenerating the collapsible substrate from the purified stabilised porous material.

Purification suitably involves crystallisation of the stabilised porous material from solution, followed by a subsequent filtration and optional solvent washing(s). Crystallisation is suitably performed in an appropriate solvent system (e.g. acetone) which may suitably be the reaction solvent in which the stabilised porous material is formed. Suitably the crystallisation solvent system is substantially anhydrous (see above definitions for water quantities).

Regeneration of the collapsible substrate may be suitably performed in a solvent system (optionally a different solvent system to the initial crystallisation, and suitably a different solvent system to that used during the formation of the stabilised porous material) which is "wet" or contains at least one mole equivalent of water for every mole equivalent of molecular tie. Suitably regeneration involves hydrolysis of the molecular tie to regenerate the collapsible compound and molecular tie compound.

Molecular Tie Compound

The molecular tie compound may be or correspond to a molecular tie compound as described in relation to the method of stabilising a collapsible substrate, and may be a compound of Formula B (or relevant sub-definitions thereof).

The molecular tie compound is as defined herein and suitably creates a bridge between two or more reactive moieties of the collapsible compound in order to stabilise the (potentially) porous structure of the collapsible compound.

The size of the molecular tie compound is preferably selected to complement the collapsible compound in question. For instance, the combination of molecular tie compound and collapsible compound are suitably selected to allow sufficient molecular tying to occur (to provide the required physical stabilisation) without compromising pore size—the resulting stabilised compound suitably has enough pore space to accommodate the required "guests".

The molecular tie compound is suitably a relatively small molecule, especially where the cavity(s) in a corresponding collapsible compound are themselves relatively small.

Suitably the molecular tie compound is an aldehyde, a ketone, or a synthetic equivalent thereof (e.g. a protected aldehyde/ketone, an acetal, a hemiacetal, etc.). Suitably each molecular tie compound molecule reacts with two distinct reactive moieties of the collapsible compound to form a molecular tie (i.e. a bridge) between the two distinct reactive moieties, where the molecular tie retains the molecular structure of the molecular tie compound save that the reactable carbonyl oxygen (which reacts with the two distinct reactive moieties) is replaced by two single bonds, one to each of the two distinct reactive moieties. Suitably the molecular tie compound reacts with the two distinct reactive moieties to form a 5- or 6-membered heterocyclic ring. Suitably one molecular tie compound reacts with one reactive unit of the collapsible compound, where each reactive unit comprises two distinct reactive moieties.

Preferred molecular tie compounds include formaldehyde (or paraformaldehyde) or acetone, most suitably formaldehyde.

Stabilized Porous Material

The present invention provides a stabilised porous material comprising (or comprising a compound comprising) at least one set (or pair) of distinct reactive moieties interlinked via a "molecular tie" linker.

For instance, the stabilised porous material (or stabilised compound) may comprise or correspond to a stabilised porous material (or stabilised compound) as described in relation to the method of stabilising a collapsible substrate, and may comprise tied units of Formula C (or relevant sub-definitions thereof) and optionally linkers, for instance, of Formula $L_1$ (or sub-definitions thereof).

As explained elsewhere herein, the stabilised porous material is suitably a direct derivative of a corresponding collapsible compound and therefore inherits substantially the same structure save for the molecular ties. As such, as for the collapsible compound, the stabilised compound may suitably comprise one or more reactive units (e.g. containing one or more, preferably two or more reactive moieties such as amines), at least one of which has been transformed into a tied unit (e.g. an aminal), wherein said reactive unit(s) and/or tied unit(s) are covalent linked via an interlinking linker unit as defined herein.

In the most preferred embodiments, a stabilised compound comprises a plurality of tied units (preferably at least three, suitably six) and is substantially free of any reactive units (i.e. all reactive units have reacted to produce tied units).

The stabilised porous materials of the invention are suitably crystalline, suitably even where the material is desolvated (e.g. for at least 12 h at 80° C.) and/or where at least 50% of the pores (suitably at least 90%) are vacant.

The stabilised porous materials of the invention are suitably characterised by a Brunauer-Emmett-Teller (BET) surface area of at least 50 $m^2/g$, suitably at least 100 $m^2/g$, suitably at least 200 $m^2/g$, suitably at least 300 $m^2/g$, suitably at least 350 $m^2/g$.

The stabilised porous materials of the invention are suitably characterised by a molar Brunauer-Emmett-Teller (BET) surface area of at least 50 $m^2/mmol$, suitably at least 100 m²//mmol, suitably at least 200 m²//mmol, suitably at least 300 m²//mmol, suitably at least 400 m²//mmol.

The stabilised porous materials of the invention suitably have a BET surface area that is within +/−30% of the BET surface area of the corresponding imine from which the corresponding collapsible substrate/compound was formed, suitably within +/−20%, suitably +/−10%. The stabilised porous materials of the invention suitably have a molar BET surface area that is within +/−10% of the BET surface area of the corresponding imine from which the corresponding collapsible substrate/compound was formed, suitably within +/−5%, suitably +/−2%. As such, in the stabilised porous material porosity is substantially restored where it was previously lost as a result of chemically stabilising the original parent imine structure. As a result the stabilised porous material is suitably both physical stable and chemically stable.

The stabilised porous material of the invention may serve as host, in a host-guest complex, to a variety of guest compounds and is suitably selective for certain guest compounds over other compounds. Suitably guest compound(s) (e.g. which may be sorbed by the stabilised porous material) may include carbon dioxide, and even non-gaseous compounds such a benzoic acid. The guest compound(s) may be hydrophobic or hydrophilic, depending on the prevailing environment within the pores of the stabilised porous material (which may be judiciously adjusted, for instance by tailoring either the collapsible compound or molecular tie compound accordingly to afford hydrophobic, hydrophilic, or substantially neutral pore environments). The guest compound(s) may be acidic compounds or basic compounds, since the stabilised porous materials of the invention suitably tolerate both acid and basic conditions, suitably as a result of appropriate pre-treatment steps to improve chemical stability (e.g. reducing a polyimine to a corresponding polyamine cage).

In a particular embodiment (e.g. especially where the molecular tie is derived from acetone, suitably with a collapsible compound of Formula A3), the stabilised porous material is suitable for "carbon capture" in that it is able to host/sorb and retain carbon dioxide, suitably selectively over nitrogen and/or oxygen. Suitably such carbon dioxide sorption (selectively or otherwise) properties are prevalent at SATP. Where the stabilised porous material is derived from an polyamine cage which was itself derived from a polyimine cage, suitably said stabilised porous material has a higher selectivity for $CO_2$ than the parent polyimine cage.

Sorption Composition

The present invention provides a method of preparing a sorption composition, suitably as defined herein. The sorption composition is suitably a solid composition, suitably a microporous solid composition. Likewise the stabilised porous material is suitably a solid material, suitably a microporous solid material.

The method suitably comprises mixing a stabilised porous material, as defined herein, with one or more additional porous or non-porous materials, to thereby produce a mixture. Such mixing may comprise solid blending, and optionally may involve a granulating and/or compressing the mixture (depending on the ultimate application).

As such, the present invention also provides a sorption composition, obtainable by, obtained by, or directly obtained by the method of preparing a sorption composition as defined herein.

Furthermore, the present invention provides a sorption composition, comprising a stabilised porous material as defined herein, and optionally one or more additional porous materials.

Though the sorption composition need only comprise the stabilised porous material, in some embodiments the composition comprises additional materials, suitably additional solid materials, depending on the intended application of the sorption composition. As such, the stabilised porous materials may be an additive in an existing sorption composition or may form the basis of a new sorption composition with which other additive(s) may be mixed. For instance, one or more additional materials may be used in combination with the stabilised porous material of the invention to augment the effectiveness of the stabilised porous material and/or to supplement the functionality of the composition. For instance, existing compositions which may already serve a desired function (e.g. carbon capture, pollutant capture, ion exchange, etc.) may be mixed with a stabilised porous material of the invention to provide a sorption composition.

Additional porous materials may include any porous materials known in the art, such as zeolites, porous clays, and/or porous forms of activated carbon.

Additional non-porous materials may include any suitable non-porous materials known in the art (suitably those which act in tandem with a stabilised porous material of the invention, be it synergistically or otherwise). Such non-porous materials may include compounds which transiently capture carbon dioxide or which capture other (e.g. harmful) substances.

The sorption compositions and materials of the invention (including the stabilised porous material or even pre-stabilised forms thereof) may suitably selectively sorb. For instance, either or both the stabilised porous material and/or pre-stabilised (i.e. pre-tied) form thereof may selectively sorb formaldehyde over water. Moreover, the stabilised porous material may selectively sorb radon over over helium.

Uses of Stabilised Porous Materials and Compositions thereof

The stabilised porous materials and sorption compositions of the invention may be used in a variety of contexts. By way of example, a stabilised porous material and/or sorption composition of the invention may be used:

In the filtration, scrubbing, or separation of one or more sorbable substrates (e.g. pollutants), suitably from a mixture comprising the one or more sorbable substrates;

Recycling of certain sorbable substrates;

Catalysis;

In analytical chemistry, e.g. to facilitate analysis of certain compounds which may be more difficult to analyse outside a porous medium;

In molecular sensing (e.g. for sensing when certain compounds are present or present above a certain concentrations);

In selective chromatography (e.g. shape-selective chromatography or chiral chromatography);

As molecular additives in organic-organic mixed-matrix membranes;

In petroleum engineering and treatments;

In materials science.

As such, the present invention provides a use of a stabilised porous material as defined herein for any of the aforementioned applications.

Sorbing Sorbable Substrates

The present invention provides a method of sorbing one or more sorbable substrates, as defined herein. The method suitably involves contacting the one or more sorbable substrates with a sorption composition as defined herein.

The sorbable substrate may be any suitable guest element or guest molecule to which a sorption composition of the invention may play host. The sorbable substrate is suitably fluidic (i.e. non-solid) or provided in a fluidic form, optionally in a mixture with other non-sorbable or less-sorbably substrates (in this manner the sorption composition may serve to separate some or all of a relatively sorbable substrate from a relatively non-sorbable substrate). Alternatively, if the sorbable substrate is a solid in a its pure form at SATP, prior to contacting with the sorprtion composition the sorbable substrate is suitably transformed into aerosols, or is otherwise mobiles in a fluid medium, most preferably dissolved in a fluid medium prior to contact with the sorption composition.

The sorbable substrate may be gaseous at SATP—such as carbon dioxide. The sorbable substrate may be a liquid or solution at SATP—such as a benzoic acid solution, where benzoic acid is the sorbable substrate.

Suitably, the sorbable substrate may be an element, especially a gaseous element such as a nobel gas (e.g. He, Ne, Ar, Kr, Xe, Rn), or a gaseous molecule such as $H_2$, $N_2$, $CO_2$, CO, HCN. In a particular embodiment, the sorbable substrate may be Kr, Xe, or Rn.

In a particular embodiment, the sorbable substrate is radon, most suitably gaseous radon. Such gaseous radon may be synthetic or naturally-occurring radon, most suitably naturally-occuring. In particular, the inventors noted that FT-RCC3 (of the appended examples) exhibited a surprisingly high capacity and affinity for radon, and formed extremely stable sorption complexes thereof. FT-RCC3 also selectively sorbed gaseous radon from an atmosphere comprising a low concentration of radon. As such, a stabilised porous material comprising a polyamine cage, suitably a polyamine cage comprising formaldehyde-derived molecular ties, is particularly well suited for radon capture.

The step of contacting with the sorption composition suitably involves directly contacting the sorption composition with the sorbable substrate (or fluidised form thereof).

Suitably the contacting involves eluting the sorption composition with the sorbable substrate (or fluidised form thereof). Suitably such elution involves deliberately channelling the sorbable substrate into contact with the sorption composition. Suitably the elution involves passing the sorbable substrate (or a flux thereof) through, across or over a localised bulk of sorption composition, and suitably at least some of the sorbably substrate is sorbed within the soption composition. In a particular embodiment, the sorption composition may be located within a channel, conduit, or pipeline through which a sorbable substrate is passed. Such a channel, conduit, or pipeline may comprise a plug or packed column of sorption composition through which a sorbable substrate (or a mixture comprising the sorbable substrate) may pass. As such, the invention suitably provides a sorption device (e.g. scrubbing or filtration device) comprising a stationary phase (e.g. a plug, packed column, moving bed, etc.) comprising a sorption composition as defined herein. For example, exhaust pipework from a carbon-dioxide generating industrial process may be furnished with such a sorption device or scrubber to selectively remove carbon dioxide from an exhaust stream.

Sorption Complexes

The result of contacting a sorption composition with a sorbable substrate (or mixture comprising a sorbable substrate) is a sorption complex. As such, the present invention provides a sorption complex comprising one or more sorbable substrates sorbed within and/or upon a stabilised porous material.

Regenerating Stabilised Porous Materials/Releasing Sorbed Substrates

Sorption complexes, once formed, may be used in a variety of ways. For instance, where a sorption complex serves as a medium for storing and/or transporting a sorbable substrate which may be otherwise difficult to store and/or transport, then this sorption complex may be used to liberate (or regenerate) the sorbable substrate for subsequent use. Such liberation of sorbable substrate may be performed in situ (e.g. in a reaction mixture which utilises the sorbable substrate as a reagent) or prior to being used (e.g. to fill a gas cylinder etc.). Removing the sorbable substrate from sorption complex may be achieved by a variety of means, depending on the nature of the sorbable substrate and the nature of the sorption composition. In an embodiment, this may involve eluting the sorption complex with a release substance which either preferentially replaces/displaces the sorbable substrate within the pores of the sorption composition or otherwise washes out the sorbable substrate (e.g. into an appropriate solvent system). The sorbable substrate may then be recovered by standard techniques known in the art (e.g. concentration in vacuo to remove the release substrate/solvent). Alternatively, the application of pressure or heat may be sufficient to release the sorbably substrate.

In some embodiments, the sorbable substrate may be an undesirable compound or pollutant in need of safe disposal. For instance, where the sorbable substrate is carbon dioxide, it may be desirable to dispose of either the sorption complex itself, or alternatively transfer the carbon dioxide held therein to a more suitable long-term storage/capture solution. Where the sorbable substrate is a pollutant, it may be desirable to simply dispose of the sorption complex containing said pollutant, or alternatively treat the sorption complex to neutralise the pollutant or otherwise transform the pollutant into something less harmful. This may involve first releasing the pollutant prior to treating the pollutant directly.

Capturing/Sorbing Molecular Tie Compounds with Collapsible Substrate (Pre-Stabilised)

In a surprising development, the inventors discovered that effective sorption of sorbable substrates is not the sole preserve of the stabilised porous materials (whose porous structure has been stabilised) produced by the invention. Where the sorbable substrate is itself a molecular tie compound (suitable as defined herein), a collapsible substrate may itself serve as an effective sorption agent.

As such, the present invention provides an alternative or additional sorption composition comprising a collapsible substrate as defined herein. Such a sorption composition may be a sorption composition as defined elsewhere herein in relation to a stabilised porous material, with all references to the "stabilised porous material" being replaced by a reference to a "collapsible substrate". As such, the sorption composition may comprise a collapsible substrate, and optionally one or more additional non-porous and/or porous materials. Suitably such a composition is for use in sorbing a sorbable substrate which can itself serve as a molecular tie compound.

The present invention therefore further provides a method of capturing (and/or sorbing) one or more (preferably gaseous) "molecular tie" compounds, the method comprising contacting the one or more "molecular tie" compounds with a collapsible substrate as defined herein, or composition (e.g. sorption composition) comprising said collapsible substrate.

Where the sorbable substrate is a molecular tie compound, the collapsible substrate or corresponding sorption composition suitably sorbs the sorbable substrate via both chemisorption and physisorption. As such, suitably the product of this dual-sorption process is a sorption complex as defined elsewhere herin, wherein the molecular tie compound is both a molecular tie compound (involved in chemisorptions) and a sorbable substrate (involved in subsequent physisorption).

The chemisorption is suitably a consequence of the molecular tie compound reacting with the collapsible substrate to produce a stabilised porous material as defined elsewhere herein. As such the chemistry to produce the stabilised porous materials defined herein is being utilised in the sorption process itself.

The physisorption suitably involves adsorption within the pores of the stabilised porous material produced by the initial chemisorption.

Therefore, rather than the "single-sorption" process by which stabilised porous materials (and other existing porous materials) sorb sorbable substrates, the collapsible substrates of the invention may serve in "dual-sorption" processes which, as noted by the inventors, sorb significantly more sorbable substrate (per gram of collapsible material/sorption composition). Furthermore, such collapsible substrates can often be surprisingly selective, and sometimes more selective than their corresponding stabilised porous material counterparts. Moreover, the resulting sorption complexes typically exhibit greater stability than single-sorption compositions such as activated carbon.

A sorption composition comprising a stabilised porous material may thus be considered a single-sorption composition, whereas a sorption composition comprising a collapsible substrate may be considered a dual-sorption composition (at least with respect to molecular tie compounds).

Suitably at least some of the molecular tie compound reacts with the collapsible substrate to cause at least one set (or pair) of distinct reactive moieties within the collapsible substrate to become mutually interlinked via a "molecular tie" linker derived from the molecular tie compound to thereby produce a stabilised porous material (suitably as defined herein). Suitably at least some of the molecular tie compound is sorbed (without chemically reacting, e.g. physically adsorbed) within pores of the resulting stabilised porous material (i.e. not just at the surface). Suitably, given a sufficient supply of the molecular tie compound, the collapsible substrate is able to utilise at least 20%, suitably at least 50%, suitably at least 80% of its pores (or pore volume) in sorbing the molecular tie compound. Suitably such a method involves "dual sorption" (i.e. involving both chemical capture of the gaseous molecular tie compound, following the aforementioned chemical reaction, and physical capture, following passage of the molecular tie compound into the stabilised pores).

The chemisorption of a molecular tie compound, especially formaldehyde, within a collapsible substrate of the invention suitably enhances the physisorption capacity (and/or the physisorption affinity) of the collapsible substrate with respect to the molecular tie compound. In this manner, the collapsible substrate exhibits a form of co-operative binding of the molecular tie compound whereby each successive chemisorption of the molecular tie compound successively increases the collapsible substrate's (or increasingly stabilised porous material's) affinity and/or capacity for the molecular tie compound.

Unless stated otherwise, or unless clearly incompatible therewith, any features defined herein in relation to a single-sorption compositions, derivatives thereof (e.g. sorption complexes), and relevant uses and methods (sorbing sorbable substrates), may also be features of the dual-sorption compositions of the invention, derivatives thereof, and relevant uses and methods relating thereto.

Collapsible Substrate

The collapsible substrate in dual-sorption compositions may be any collapsible substrate (or collapsible compound) as defined herein. Suitably the collapsible substrate in this context is chosen to suit the sorbable substrate/molecular tie compound intended for sorption. As such, suitably the collapsible substrate is able to react with the sorbable substrate to produce a stabilised porous material or stabilised compound as defined herein.

In a preferred embodiment, however, the collapsible substrate is the compound of Formula A3.

Sorbable Substrate/Molecular Tie Compound

The sorbable substrate used in methods of sorption which involve one of the dual-sorption compositions of the invention may be any suitable molecular tie compound, suitable a molecular tie compound as defined herein.

Suitably the sorbable substrate in this context is chosen to suit the collapsible substrate used in the sorption process. As such, suitably the sorbable substrate is able to react with the collapsible substrate to produce a stabilised porous material or stabilised compound as defined herein.

Suitably, the sorbable substrate is a gaseous molecular tie compound—suitably the sorbable substrate is gaseous at SATP. Dual-sorption compositions of the invention are particularly effective (despite their inherent pore-structure/physical instability) for sorbing gaseous molecular tie compounds.

In a preferred embodiment, however, the sorbable substrate a compound of Formula B, most suitably formaldehyde. In a preferred embodiment, the sorbable substrate is gaseous formaldehyde.

In a particular embodiment, the dual-sorption composition comprising a collapsible substrate of Formula A3 is especially suitable where gaseous formaldehyde is the sorbable substrate.

Suitably, the dual-sorption composition is able to sorb at least 50 cm$^3$ gaseous sorbable substrate (preferably formaldehyde) per gram of collapsible substrate, suitably at least 100 cm$^3$/g, suitably at least 150 cm$^3$/g, suitably about 200 cm$^3$/g, which represents a significant improvement in uptake compared to polyacrylonitrile-based carbon fibre, which is currently the best-performing absorbent material for formaldehyde.

In sorption methods, the sorbable substrate may be suitably contacted with the sorption composition as defined elsewhere herein, optionally where the sorption composition is a part of a sorption device or scrubber.

Resulting sorption complex may likewise be used and/or treated in the manner aforedescribed, including in sorbable substrate release, sorption composition regeneration, etc. As such, the present invention provides an effective means of scrubbing gaseous formaldehyde from either the atmosphere or a waste/exhaust stream, before later releasing formaldehyde in a safe environment. The released formaldehyde may then be used or otherwise transformed into a safer form of formaldehyde (e.g. a solution of paraformaldehyde). In this manner, the relevant sorption composition may be recycled and reused.

Suitably a sorption complex formed by the sorption of formaldehyde within a dual-sorption composition will retain substantially all (preferably at least 80 wt %, suitably at least 90 wt %, suitably at least 95 wt %, suitably at least 99 wt % of the total amount of sorbed formaldehyde) formaldehyde after 15 minutes (preferably after 30 minutes) exposure to a temperature of 100° C., suitably 200° C., suitably 290° C. (preferably at 1 Bar pressure). Likewise, a sorption complex formed by the sorption of formaldehyde within a dual-sorption composition will suitably retain substantially all (preferably at least 80 wt %, suitably at least 90 wt %, suitably at least 95 wt %, suitably at least 99 wt % of the total amount of sorbed formaldehyde) formaldehyde after 24 hours exposure, at SATP, to a relative humidity of 50%, suitably 70%, suitably 90%. This is in stark contrast to the performance of existing sorption matrices, such as activated carbon, which release formaldehyde a high temperature and/or high humidity, as per standard physisorption behaviour.

Finally, the dual-sorption compositions of the invention show remarkable selectivity towards sorbable substrates as compared to existing sorption matrices, such as activated carbon, especially under humid conditions. This is thought to be a consequence of the relatively high affinity of dual-sorption compositions for corresponding sorbable substrates (e.g. formaldehyde) compared to water. In fact, the presence of water can facilitate, rather than inhibit (as per the case for activated carbon) selective formaldehyde uptake. This effect is particular pronounced when utilising polyamine cages, especially those containing pre-organised reactive diamine units.

Uses of Dual-Sorption Compositions

Dual-sorption compositions may be used in exactly the same way as their single-sorption composition counterparts.

In a particular embodiment, the dual-sorption compositions of the invention are used to selectively sorb gaseous formaldehyde, which is a highly toxic compound which is notoriously difficult to remove from the atmosphere or from exhaust mixtures. As formaldehyde is released from a range of industrial processes and products, the dual-sorption compositions of the invention are particularly useful in methods of sorbing formaldehyde generated from:

1. The combustion of biofuel, natural gas, kerosene, tobacco smoke
2. Hydraulic fracturing
3. Paper products, e.g. paper towels, sanitary products and tissues
4. Wood products such as plywood, particle board and decorative panelling
5. Insulation products like urea formaldehyde foam insulation (UFFI)
6. Consumer products e.g. cosmetics, deodorants, shampoo and disinfectants
7. Resins and adhesives
8. Plant fertiliser
9. Fabric dyes
10. In healthcare as a sterilant and disinfectant The dual-sorption compositions of the invention can even selectively sorb formaldehyde at low concentrations/partial pressures thereof, even at the lower detectable limit for formaldehyde. For instance, the dual-sorption compositions of the invention may suitably sorb formaldehyde at a concentration of 100 ppm or higher, suitably at a concentration of 50 ppm or higher, suitably at a concentration of 10 ppm or higher. As such, the compositions of the invention not only contribute to the art by way of new viable methods of formaldehyde capture/scrubbing, but also by way of facilitating the use of industrial processes that may previously have been deemed unviable or unsafe owing to the level of formaldehyde output.

EXAMPLES

Many of the synthetic methods, analytical methods, and results pertaining to the formation of shape-persistent porous organic cages are described in Cooper et al, *J. Am. Chem. Soc.* 2014, 136, 7583-7586 and its accompanying Supporting Information, both of which are hereby incorporated by reference.

Materials and Equipment 1,3,5-Triformylbenzene was purchased from Manchester Organics, UK. All other chemicals were purchased from Sigma-Aldrich and used as received. CC3 (Cage 3) was prepared as previously reported in its homochiral form, CC3-R.[41]

Note on Nomenclature: Helicity, or axial chirality, is an intrinsic property of these molecular cages. All six bisimino vertices must be of the same enantiomer, and the vertex substituents must occupy exo-positions, in order to obtain a tetrahedral molecular structure. In this study, CC3 was prepared using the homochiral (1R,2R)-cyclohexanediamine to give the homochiral cage, CC3-R. All reactions reported proceed identically with the opposite enantiomer, CC3-S. Where the cage is referred to as CC3, for brevity, this refers to the homochiral cage, CC3-R, rather than the racemate (CC3-R,S). Reducing CC3 to RCC3 and the further modification to AT-RCC3 and FT-RCC3 does not change the chirality of the cage.

Solution NMR. Solution $^1$H NMR spectra were recorded at 400.13 MHz using a Bruker Avance 400 NMR spectrometer. $^{13}$C NMR spectra were recorded at 100.6 MHz.

Fourier Transform Infrared Spectroscopy (FTIR). IR spectra were collected on a Bruker Tensor 27 spectrometer. Samples were analysed as KBr disks for 16 scans with a resolution of 4 cm$^1$. Spectra were recorded in transmission mode.

Thermogravimetric Analysis. TGA analysis was carried out using a Q5000IR analyser (TA instruments) with an automated vertical overhead thermobalance. The samples were heated at the rate of 5° C./min.

Powder X-ray Diffraction. Laboratory powder X-ray diffraction (PXRD) data were collected in transmission mode on samples held on thin Mylar film in aluminum well plates on a Panalytical X'Pert PRO MPD equipped with a high throughput screening (HTS) XYZ stage, X-ray focusing mirror, and PIXcel detector, using Ni-filtered Cu Kα radiation. Data were measured over the range 5-50° in ~0.013° steps over 60 min.

Electron Microscopy. Imaging of the crystal morphology was achieved using a Hitachi S-4800 cold field emission scanning electron microscope (FE-SEM) operating in both scanning and transmission modes. Scanning-mode samples were prepared by depositing dry crystals on 15 mm Hitachi M4 aluminium stubs using an adhesive high-purity carbon tab before coating with a 2 nm layer of gold using an Emitech K550X automated sputter coater. Imaging was conducted at a working distance of 8 mm and a working voltage of 3 kV using a mix of upper and lower secondary electron detectors. Transmission-mode samples were prepared by dispersing the cage particles in a methanol suspension and depositing onto carbon-coated copper grids (300 mesh), imaging at 30 kV working voltage and 7 mm distance.

Gas Sorption Analysis. Gases of the following purities were used: hydrogen (99.9995%-BOC gases) and carbon dioxide (SCF grade-BOC gases). Surface areas and pore size distributions were measured by nitrogen adsorption and desorption at 77.3 K using a Micromeritics ASAP 2020 volumetric adsorption analyser. Samples were degassed at offline at 80° C. for 15 h under vacuum (10-5 bar) before analysis, followed by degassing on the analysis port under vacuum, also at 80° C. Carbon dioxide isotherms were measured at 289K using a Micromeritics 2420 volumetric adsorption analyser using the same degassing procedure.

Single Crystal X-ray Diffraction. Single crystal X-ray data were measured on a Rigaku MicroMax-007 HF rotating anode diffractometer (Mo-Kα radiation, λ=0.71073 Å, Kappa 4-circle goniometer, Rigaku Satum724+ detector). Or for formaldehyde tied reduced CC3 (FT-RCC3) at beamline 119, Diamond Light Source, Didcot, UK using silicon double crystal monochromated radiation (λ=0.6889 Å).[42] Empirical absorption corrections using equivalent reflections were performed with the program SADABS.[43] Structure were solved with SHELXD,[44] or by direct methods using SHELXS,[44] and reined by full-matrix least squares on $F^2$ by SHELXL-97,[44] interfaced through the programme OLEX2.[45] Unless stated all non-H atoms were refined anisotropically and H atoms were fixed in geometrically estimated positions using the riding model. In the absence of heavy scatters Friedel pairs were merged.

Example 1—Synthesis of RCC3

The imine cage CC3-R (926 mg, 0.83 mmol) was dissolved in a $CHCl_3$/methanol mixture (1:1 v/v, 50 mL) by stirring. When this solution became clear, sodium borohydride (1.00 g, 26.5 mol) was added and the reaction was stirred for a further 12 hours at room temperature. Water (2 mL) was then added, and the reaction stirred for a further 12 hours. The solvent was then removed under vacuum. The resulting white solid was extracted with chloroform (2×50 mL) and then the combined organic phase was washed by water (2×100 mL). The $CHCl_3$ phase was dried using anhydrous $MgSO_4$ before being removed under vacuum. Amine cage 1 (crude yield=900 mg, 95.1%) was obtained as a white solid. $^1H$ NMR ($CDCl_3$, 400 MHz) δ 7.12 (s, 12H, —ArH), 3.81 (d, 12H, —$ArCH_2$), 3.59 (d, 12H, —$ArCH_2$), 2.18 (m, 12H, CH on cyclohexane), 0.95-1.98 (m, 48H, $CH_2$ on cyclohexane) ppm; $^{13}C$ NMR ($CDCl_3$, 100 MHz): δ 141.2, 124.9, 61.2, 50.7, 32.0, 25.0 ppm. IR (KBr pellet, v) 2922 (s), 2850 (s), 1603 (w), 1446 (s), 1354 (w), 1338 (w), 1153 (m), 1113 (s), 856 (s), 789 (m), 750 (m), 714 (m), 525 (w) $cm^{-1}$. MS (ES+) 1141.9 ([M+H]$^+$).

Single Crystal Data for RCC3

Crystal data for RCC3-14.68($H_2O$). Formula $C_{72}H_{137.36}N_{12}O_{14.68}$; M=1406.21 g·mol$^{-1}$; cubic space group F4$_1$32, colourless crystal; a=25.71(1) Å; V=16999 (13) Å$^3$; ρ=1.092 g·cm$^{-3}$; μ=0.077 mm$^{-3}$; F (000)=6034; crystal size=0.25×0.20×0.15 mm$^3$; T=100(2) K; 33 042 reflections measured (2.63<Θ<25.01°), 1274 unique ($R_{int}$=0.0466), 1070 (I>2σ(I); $R_1$=0.0759 for observed and $R_1$=0.0863 for all reflections; $wR_2$=0.2324 for all reflections; max/min residual electron density=0.493 and −0.275 e·Å$^{-3}$; data/restraints/parameters=1274/01100; GOF=1.054.

RCC3-14.68($H_2O$) crystallised from a MeOH/$H_2O$ solution. The structure was solved and refined in the chiral cubic space groups F4$_1$32 with the asymmetric unit comprised of $^1/_{12}$ of a RCC3 fragment. Residual electron density was extremely diffuse and tentatively assigned as $H_2O$ solvent, the occupancies for which were determined using $F_{VAR}$ during refinement. The $H_2O$ solvent molecules were refined without riding proton atoms however these were included in the refined formula unit.

Desolvation of RCC3

To obtain a large quantity of crystalline RCC3 for subsequent analysis, a solution of RCC3 dissolved in $CHCl_3$ was allowed to slowly evaporate over two days. Powder X-ray diffraction (PXRD) confirmed that this solvate material was the same phase as the single-crystal structure. Different desolvation methods for activation of the RCC3 solvate were investigated, including high/low temperature vacuum, $N_2$ flow, solvent exchange, and supercritical $CO_2$ drying. However, none of these activation conditions maintained the crystallinity of RCC3 upon desolvation, and we instead isolated an amorphous solid in all cases that showed no Bragg reflections in the PXRD pattern.

Example 2—Synthesis of AT-RCC3

The reduced amine cage RCC3 (50 mg, 0.044 mmol) was dissolved in 3 mL acetone in a 10 mL vial. The vial was sealed and left to stand. Single crystals of AT-RCC3 gradually appeared on the walls and the bottom of the vial after about 30 min. The crystals were collected after 12 h by filtration and washed by acetone (2×100 mL). Yield: 39 mg, 75.4%. (Note: The filtrate can be left to stand for >12 h to collect a further crop of crystals, thus improving this 75% yield.) $^1H$ NMR ($CDCl_3$, 400 MHz) δ 7.35-6.83 (m, 12H, —ArH), 4.00-3.04 (m, 12H, —$ArCH_2$), 2.49-0.7 (m, 12H, —$ArCH_2$), 2.18 (m, 60H, CH & $CH_2$ on cyclohexane), 0.95-1.98 (m, 48H, $CH_2$ on cyclohexane) ppm; $^{13}C$ NMR ($CDCl_3$, 100 MHz): δ 141.2, 127.7, 125.0, 61.4, 51.8, 50.8, 50.0, 31.8, 30.9, 25.0, 23.9 ppm. IR (KBr pellet, v) 2927 (s), 2855 (m), 1605 (w), 1449 (m), 1374 (w), 1355 (w), 1337 (w), 1293 (w), 1206 (w), 1158 (w), 1110 (w), 1074 (w), 1001 (w), 862 (w), 789 (w), 736 (w) $cm^{-1}$. MS (ES+) 1181.9 ([M+H]$^+$).

Single Crystal Data for AT-RCC3

Crystal data for AT-RCC3-7.5($H_2O$). Formula $C_{75}H_{127}N_{12}O_{7.5}$; M=1301.77 g·mol$^{-1}$; cubic space group F4$_1$32, colourless crystal; a=25.469(1) Å; V=16520(2) Å$^3$; ρ=1.047 g·cm$^{-3}$; μ=0.068 mm$^{-3}$; F (000)=5648; crystal size=0.18×0.18×0.12 mm$^3$; T=100(2) K; 29 022 reflections measured (1.38<Θ<23.24°), 993 unique ($R_{int}$=0.0508), 955 (I>2σ(I); $R_1$=0.0848 for observed and $R_1$=0.0868 for all reflections; $wR_2$=0.2534 for all reflections; max/min residual electron density=0.485 and −0.250 e·Å$^{-3}$; data/restraints/parameters=993/17/92; GOF=1.166.

Crystal data for AT-RCC3-4.5($H_2O$). Formula $C_{75}H_{121}N_{12}O_{4.5}$; M=1262.84 g·mol$^{-1}$; cubic space group F4$_1$32, colourless crystal; a=25.612(5) Å; V=16801(6) Å$^3$; ρ=0.998 g·cm$^{-3}$; μ=0.063 mm$^{-3}$; F (000)=5528; crystal size=0.18×0.18×0.12 mm$^3$; T=300(2) K; 26 066 reflections measured (1.38<Θ<20.88°), 759 unique ($R_{int}$=0.0767), 708 (I>2σ(I); $R_1$=0.0828 for observed and $R_1$=0.0928 for all reflections; $wR_2$=0.2501 for all reflections; max/min residual electron density=0.346 and −0.377 e·Å$^{-3}$; data/restraints/parameters=759/14/95; GOF=1.125.

Crystal data for AT-RCC3. Formula $C_{72}H_{112}N_{12}$; M=1181.76 g·mol$^{-1}$; cubic space group F4$_1$32, colourless crystal; a=25.456(6) Å; V=16495(7) Å$^3$; ρ=0.952 g·cm$^{-3}$; μ=0.057 mm$^{-3}$; F (000)=5168; crystal size=0.18×0.18×0.12 mm$^3$; T=350(2) K; 25 340 reflections measured (2.26<e<20.82°), 730 unique ($R_{int}$=0.0940), 570 (I>2σ(I);

$R_1=0.1097$ for observed and $R_1=0.1260$ for all reflections; $wR_2=0.3059$ for all reflections; max/min residual electron density=0.412 and −0.171 e·$Å^{-3}$; data/restraints/parameters=730/14/81; GOF=1.287.

AT-RCC3 crystallized from an acetone solution in the chiral cubic space group $F4_132$. The asymmetric unit for AT-RCC3 is comprised of $^1/_{12}$ of a cage molecule. Residual electron density was tentatively assigned as $H_2O$, the protons atoms were not found in the difference map but were included in the refined formula unit. The imidazolidine ring was disordered over the six diamine sites and was refined with a combined chemical occupancy of 100% in accordance with additional experimental evidence. The single crystal which was initially selected from an acetone solution and mounted at 100 K was then gradually heated to 300 K under a dry nitrogen gas flow. At 300 K a second data set was recorded. Upon completing the sample was heated to 350 K before a third and final data set was recorded. In general, to accommodate for the disordered positioning of the imidazolidine ring, the nitrogen atom was split and refined as $R_2NH$ (83% occupancy) in the absence of the imidazolidine ring or $R_2NC$ (17% occupancy) as part of the imidazolidine ring. The N atoms were refined with the constraints EADP and EXYX. Atomic displacement parameters for the disordered part were refined with ISOR and/or rigid bond restraints (DELU) during refinement, in addition the 1,3 $CH_3$—C—$CH_3$ distance was refined with a DANG restraint. The single crystal was weakly diffracting and a resolution limit of 0.90 Å was applied during refinement for the 100 K data collection. In the 300 K and 350 K data collections a 1.00 Å resolution limit was applied.

Crystal data for collapsed AT-RCC3. Formula $C72H_{112}N_{12}$; M=1181.77 g·$mol^{-1}$; orthorhombic space group $P2_12_12_1$, colourless crystal; a=14.763(5), b=17.458 (6), c=27.45(1) Å; V=7075(4) $Å^3$; ρ=1.109 g·$cm^{-3}$; μ=0.066 $mm^{-3}$; F (000)=2584; crystal size=0.28×0.09×0.05 $mm^3$; T=100(2) K; 31 603 reflections measured (1.38<Θ<24.71°), 11 774 unique ($R_{int}$=0.1219), 4629 (I>2σ(I); $R_1$=0.0829 for observed and $R_1$=0.2238 for all reflections; $wR_2$=0.2522 for all reflections; max/min residual electron density=0.548 and −0.224 e·$Å^{-3}$; data/restraints/parameters=11774/27/795: GOF=0.967.

Dynamic Properties of AT-RCC3 in Solution

Because of the reversibility of the aminal-forming reaction in solution, it was expected that the aminal product might decompose with the presence of water. Indeed, it was observed that AT-RCC3 gradually converts back to RCC3 after being stored in the NMR solvents ($CDCl_3$ or $CD_3OD$; Figure S2 and Figure S3) with the help of the trace amount of water contained in these solvents, and perhaps also the weak acidic properties of $CDCl_3$. When anhydrous, base-neutralized $CDCl_3$ was used, the decomposition process for AT-RCC3 was greatly slowed down.

Further Purification of RCC3, Taking Advantage of Aminal Reversibility of AT-RCC3 in Solution A method was developed to purify RCC3, taking advantage of the reversibility of the aminal formation. In imine reduction of CC3, it is troublesome to purify the corresponding amine product, RCC3, because of its high polarity. We therefore developed a workflow for purification of RCC3 using the reversible reaction with acetone described above. In a 25 mL flask, 100 mg crude RCC3 was dissolved in acetone (10 mL). The solution was covered and left to stand. Crystals started appearing on the wall of the flask after 30 mins. The crystals (AT-RCC3) were collected after one day by filtration and were then dissolved in a $CHCl_3/CH_3OH$ mixture (1:1 v/v) by stirring. Several drops of distilled water were added to the solution and the mixture was stirred for another 12 h. After removal of the solvents, pure RCC3 (68 mg, 70.4%) was recovered. It was observed from the corresponding $^1H$ NMR spectrum that only signals corresponding to impurities were found in the filtrate, whereas the recovered RCC3 was found to be highly pure.

Can Additional Acetones React in the Cavity of RCC3?

Only one acetone reacts with RCC3, even though there are six diamine groups in the cage. In theory, there is enough space in the RCC3 to cavity to accommodate additional dimethylimidazolidine groups. To investigate whether this is possible, further recrystallization-like reactions were repeated at higher temperatures (up to 50° C.), and mixed solvent systems were also investigated ($CHCl_3$/acetone, 1:1 v/v). In both, cases only one acetone is incorporated in the AT-RCC3 product, as confirmed by mass spectroscopy, $^1H$ NMR, and single crystal X-ray crystallography. We also refluxed RCC3 in acetone with stirring for 12 h: again, only one acetone is incorporated in the AT-RCC3 product, which was isolated and characterized by NMR, even though a trace amount of a two-acetone-reacted-product is suggested by mass spectrometry. It is believed that there are two explanations for this selectivity. First, steric hindrance effect plays a key role, this disfavours formation of a second dimethylimdazolidine ring, probably by preventing the formation of key intermediates. Second, the solubility of AT-RCC3 in acetone is significant lower than RCC3; this results in the product crystallising from solution as it is formed. This also explains the almost total conversion of RCC3 to AT-RCC3.

Collapsed AT-RCC3

Powder XRD data recorded on a sample of AT-RCC3 post gas adsorption indicated that there was an additional crystalline phase present. In addition, a contribution from amorphous material was apparent in the diffraction pattern. When this sample was illuminated with polarized light, a non-cubic single crystal phase was evident. A crystal of this phase was selected and a SC-XRD data set was recorded. Structure determination revealed this to be a collapsed conformation of AT-RCC3, which has crystallized in the orthorhombic space group $P2_12_12_1$. For this phase, the asymmetric unit was comprised of one crystallographically distinct collapsed AT-RCC3 molecule. Only one conformer of collapsed AT-RCC3 was found in the crystal lattice: that is, unlike the cubic AT-RCC3 structure, the imidazolidine ring was not found to be disordered over the six possible vertex sites.

The reason for this is apparent from the single crystal structure: in the collapsed conformation of AT-RCC3, the dimethyl groups of the imidazolidine ring are directed inwards towards the centre of the cage cavity, resulting in a loss of the tetrahedral symmetry and the intrinsic cage void. For this conformation, there is only enough void space for a single vertex to collapse inwards—in this case, the reacted imidazolidine ring. During collapse, the molecules reorient such that this collapsed vertex is not disordered in the structure.

Single crystals of collapsed AT-RCC3 were weakly diffracting. A resolution limit of 0.85 Å was applied during refinement. One cyclohexane vertex (N11-C67>C72-N12) showed signs of positional disorder, for this group one of the nitrogen atoms (N11) was split and refined over two positions. This cyclohexane vertex was refined with a rigid bond restraint (DELU) during refinement. The highest q-peak (0.55) was found is close proximity to N11.

It should be noted that upon examining single crystals of AT-RCC3, as prepared from an acetone solution, that no non-cubic single crystal phases were evident the crystals were illuminated with polarized light. The exact nature of the transformation of the open, as-synthesized conformation of AT-RCC3 to the collapsed conformation will be subject to a future study.

The collapsed structure has no solvent-accessible surface area, even for a $H_2$ probe. It is possible that the collapsed crystals were deformed by the pressure of the gas (5 bar) from the sorption experiment. Conformational searches found that only collapsed conformations of AT-RCC3 were lower in energy than 'open', porous conformations, suggesting that collapse of the void was energetically favoured. These calculated collapsed conformations exhibited the same structural motifs as the asymmetric unit from the single crystal structure.

Example 3—Synthesis of FT-RCC3

Paraformaldehyde (52 mg, 20 eq.) dissolved in $CH_3OH$ (10 mL) was stirred at 70° C. To this clear solution was added RCC3 (100 mg) dissolved in $CH_3OH$ (10 mL). A white precipitate appeared upon addition of RCC3. The reaction was stirred for a further 2 h at 70° C. The reaction was cooled to room temperature and the precipitate was collected by filtration. FT-RCC3 (52 mg, 70%) was obtained after being washed with $CH_3OH$ (3×10 mL) and dried under vacuum. $^1$H NMR (CDCl$_3$, 400 MHz) δ 7.11 (s, 12H, —ArH), 3.99 (d, 12H, —ArCH$_2$), 3.23 (s, 12H, —NCH$_2$N—), 3.19 (d, 12H, —ArCH$_2$), 2.27 (d, 12H, CH on cyclohexane), 1.96 (d, 12H, CH$_2$ on cyclohexane), 1.80 (d, 12H, CH$_2$ on cyclohexane), 1.28 (m, 24H, CH$_2$ on cyclohexane) ppm; $^{13}$C NMR (CDCl$_3$, 100 MHz): δ 140.1, 123.6, 77.2, 68.8, 57.3, 29.4, 24.4 ppm. IR (KBr pellet, v) 2925 (s), 2858 (m), 2803 (w), 1605 (m), 1436 (s), 1348 (w), 1336 (s), 1313 (w), 1292 (m), 1215 (m), 1187 (s), 1122 (m), 1094 (w), 1066 (w), 1039 (w), 1006 (m), 952 (m), 908 (m), 858 (m), 835 (s), 751 (s), 684 (m), 666(w), 584 (m), 541 (w), 453 (m) cm$^{-1}$. MS (ES+) 1213.9 ([M+H]$^+$). Accurate mass calculated for $C_{78}H_{109}N_{12}$: 1213.8898. Found: 1213.8894.

Single Crystal Data for FT-RCC3

Crystal data for FT-RCC3.4(MeOH).2(CHCl$_3$). Formula $C_{84}H_{126}Cl_6N_{12}O_4$; M=1580.67 g·mol$^{-1}$; cubic space group F4$_1$32, colourless crystal; a=25.370(3) Å; V=16329(3) Å$^3$; ρ=1.286 g·cm$^{-3}$; μ=0.268 mm$^{-3}$; F (000)=6784; crystal size=0.06×0.06×0.05 mm$^3$; T=30(2) K; 11 627 reflections measured (2.66<Θ<26.35°), 1382 unique (R$_{int}$=0.0740), 1040 (I>2σ(I); R=0.1455 for observed and R$_1$=0.1720 for all reflections; wR$_2$=0.4196 for all reflections; max/min residual electron density=0.819 and −0.465 e·Å$^{-3}$; data/restraints/parameters=1382/0/85; GOF=1.769.

Single crystals of FT-RCC3 crystallized from a CHCl$_3$/MecOH solution in the chiral cubic space group F4$_1$32. The crystals were small and weakly diffracting. Suitable quality X-ray diffraction data was obtained using a synchrotron radiation source at beamline I19, Diamond Light Source, UK. A collection temperature of 30 K was used to greatly improve data quality. One CHCl$_3$ molecule, disordered over two positions was found in the interstitial cavity between two cage windows. Additional electron density was modelled as MeOH solvent. No restraints were used during refinement. The exact occupancy of the CHCl$_3$ and MeOH solvent should be regarded as tentatively assigned due to close contacts. For a displacement ellipsoid plot of FT-RCC3.4(MeOH).2(CHCl$_3$) see Figure S25. At higher collection temperature (>275 K) single crystals of FT-RCC3 were weakly diffracting.

Morphology of as-Synthesized FT-RCC3

Figure 2:
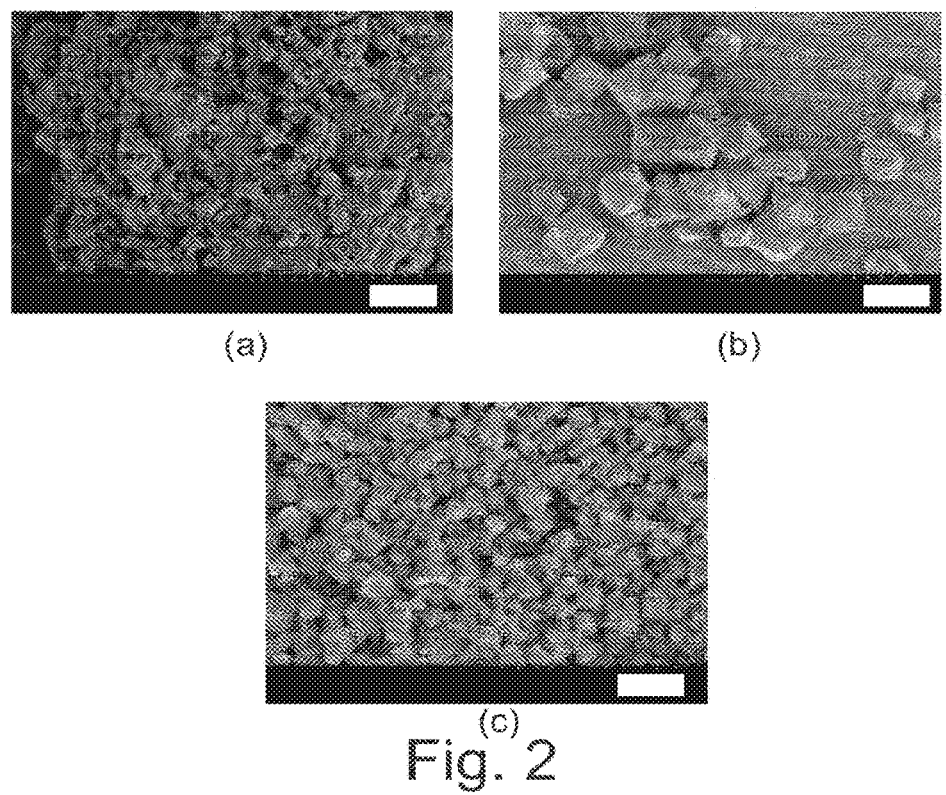
FIG. 2 shows SEM images for FT-RCC3 synthesised in (a) MeOH, (b) a mixture of MecOH/$H_2O$ (10:1 v/v) and (c) MeOH/$H_2O$ (1:1 v/v). When MeOH alone was used as reaction solvent, the as-synthesized FT-RCC3 crystals tend to aggregate into clusters with diameter around 100 μm. When water mixed with MeOH was used as the solvent, FT-RCC3 crystals were formed as discrete, uniform octahedra. The MeOH to $H_2O$ ratio affects the crystallite size (c.f., b and c).

FIG. 2 shows SEM images for FT-RCC3 synthesised in (a) MecOH, (b) a mixture of MecOH/H$_2$O (10:1 v/v) and (c) MeOH/H$_2$O (1:1 v/v). When MeOH alone was used as reaction solvent, the as-synthesized FT-RCC3 crystals tend to aggregate into clusters with diameter around 100 μm. When water mixed with MeOH was used as the solvent, FT-RCC3 crystals were formed as discrete, uniform octahedra. The MeOH to H$_2$O ratio affects the crystallite size (c.f., b and c).

Figure 3:
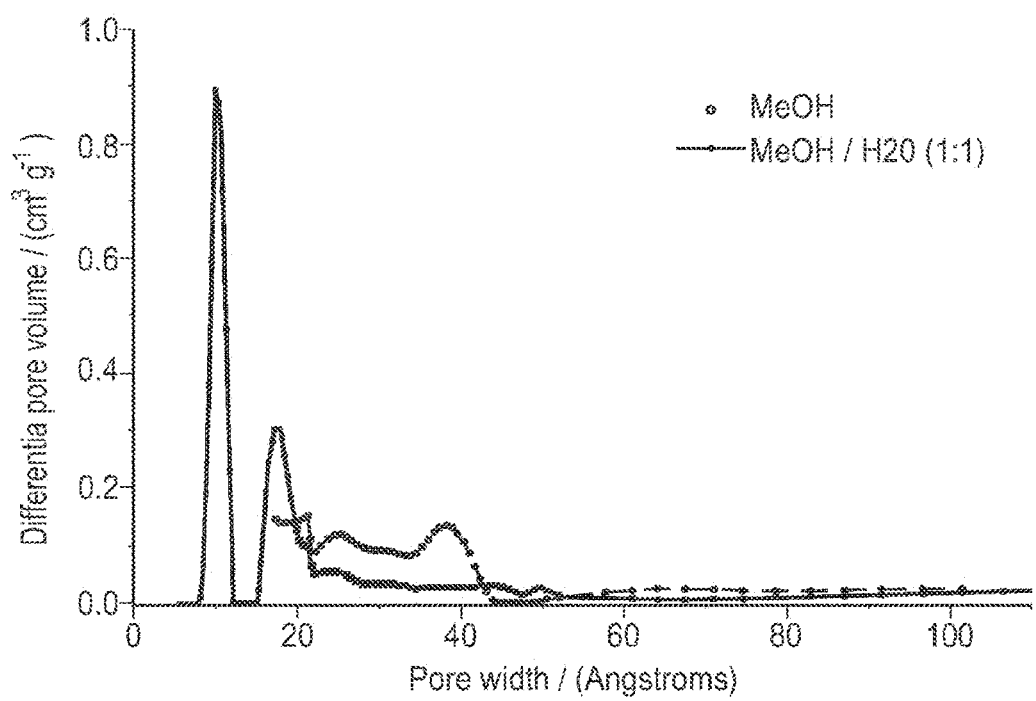
FIG. 3 shows a graphical comparison of micropore size distribution for FT-RCC3 synthesised by using MeOH or MeOH/$H_2O$ (1:1 v/v) mixture as solvents.

FIG. 3 shows a graphical comparison of micropore size distribution for FT-RCC3 synthesised by using MeOH or MeOH/H$_2$O (1:1 v/v) mixture as solvents.

Desolvation of FT-RCC3

Figure 4:
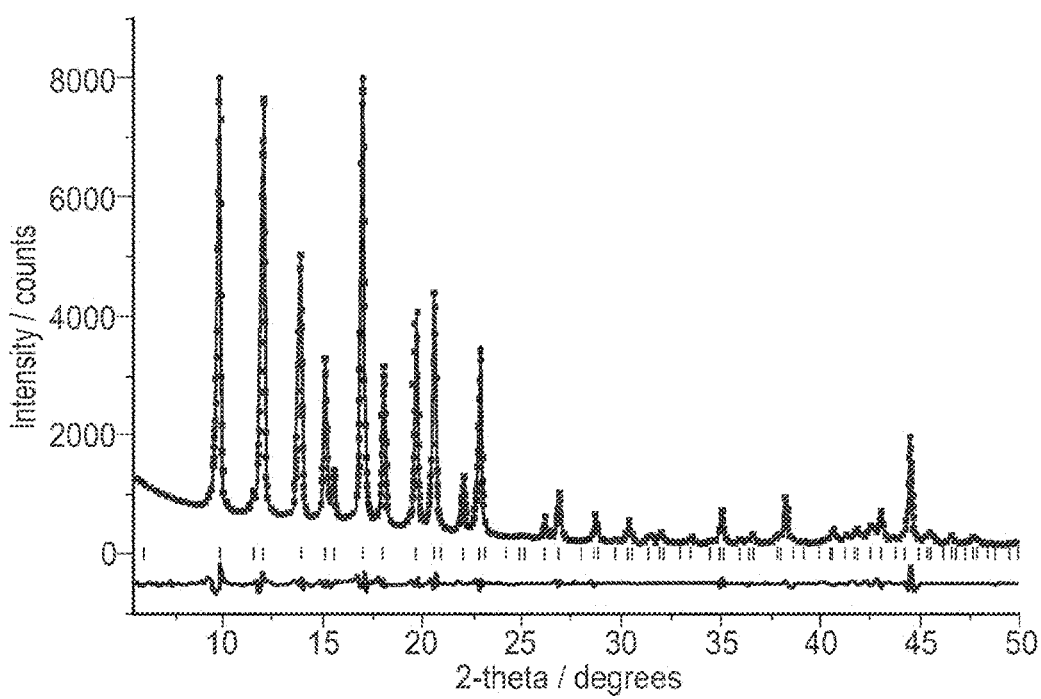
FIG. 4 shows the final observed (red circles), calculated (black line) and difference PXRD profiles for Le Bail refinement ($R_{wp}$=4.81%, $R_p$=3.39%, $\chi2$=1.22) of desolvated FT-RCC3 (a=25.4857(6) Å, V=16554(1) Å$^3$, $F4_132$). Reflection positions are also marked. Peaks due to aluminium sample holder at $2\theta$=38.2 and 44.5° are indicated by green tick marks.

FIG. 4 shows the final observed (red circles), calculated (black line) and difference PXRD profiles for Le Bail refinement (R$_{wp}$=4.81%, R$_p$=3.39%, $\chi^2$=1.22) of desolvated FT-RCC3 (a=25.4857(6) Å, V=16554(1) Å$^3$, F4$_1$32). Reflection positions are also marked. Peaks due to aluminium sample holder at 2θ=38.2 and 44.5° are indicated by green tick marks.

Figure 5:
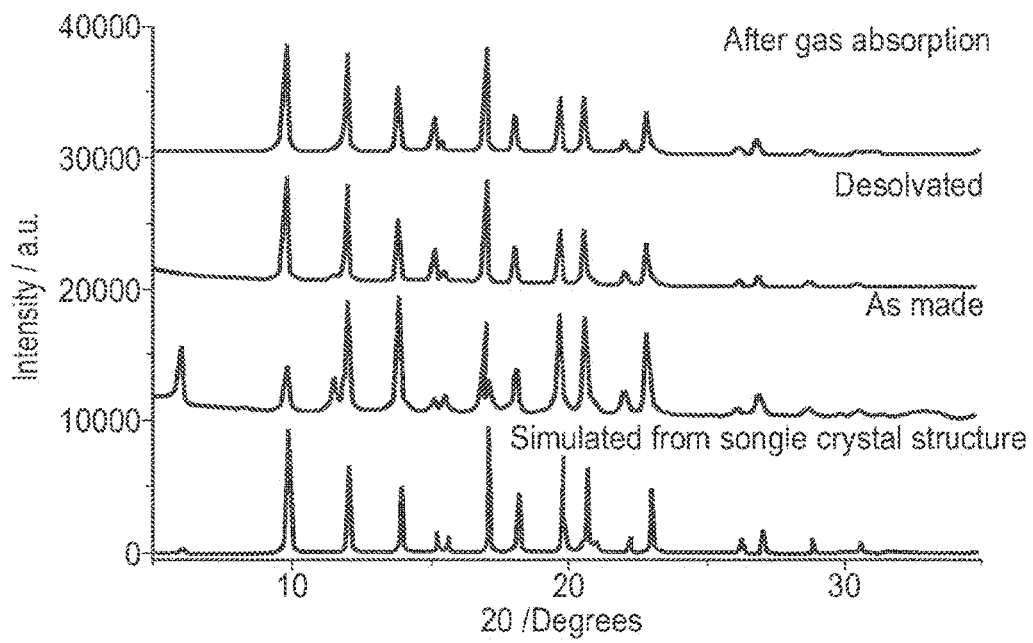
FIG. 5 shows powder X-ray diffraction patterns recorded on samples of FT-RCC3. There is no sign of FT-RCC3 losing crystallinity after being desolvated at 80 degrees under dynamic vacuum or after gas absorption analysis. Simulated pattern from solvated single crystal structure of FT-RCC3 after in silico removal of solvent shown for comparison.

FIG. 5 shows powder X-ray diffraction patterns recorded on samples of FT-RCC3. There is no sign of FT-RCC3 losing crystallinity after being desolvated at 80 degrees under dynamic vacuum or after gas absorption analysis. Simulated pattern from solvated single crystal structure of FT-RCC3 after in silico removal of solvent shown for comparison.

Conformer Searching for the Lowest Energy Conformations of FT-RCC3

Figure 6:
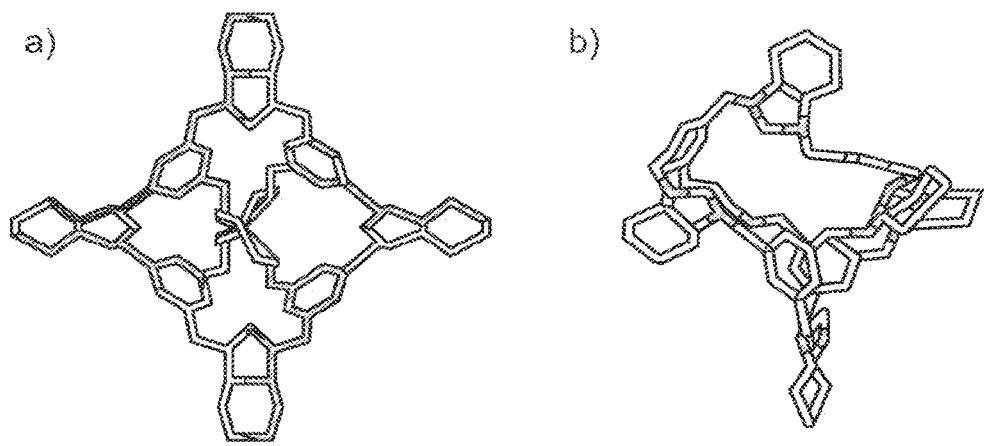
FIG. 6 shows (a) an overlay of the calculated lowest energy structure (red) and the single crystal X-ray diffraction structure of a FT-RCC3 molecule (blue); and (b) The partially collapsed, next lowest energy conformation, is sufficiently higher in energy to be confident that the open structure would form, at least in the absence of any compensatory interaction, such as with a solvent in a solvate.

FIG. 6 shows (a) an overlay of the calculated lowest energy structure (red) and the single crystal X-ray diffraction structure of a FT-RCC3 molecule (blue); and (b) The partially collapsed, next lowest energy conformation, is sufficiently higher in energy to be confident that the open structure would form, at least in the absence of any compensatory interaction, such as with a solvent in a solvate.

PXRD of FT-RCC3 after being Treated with Basic Solution

Figure 7:
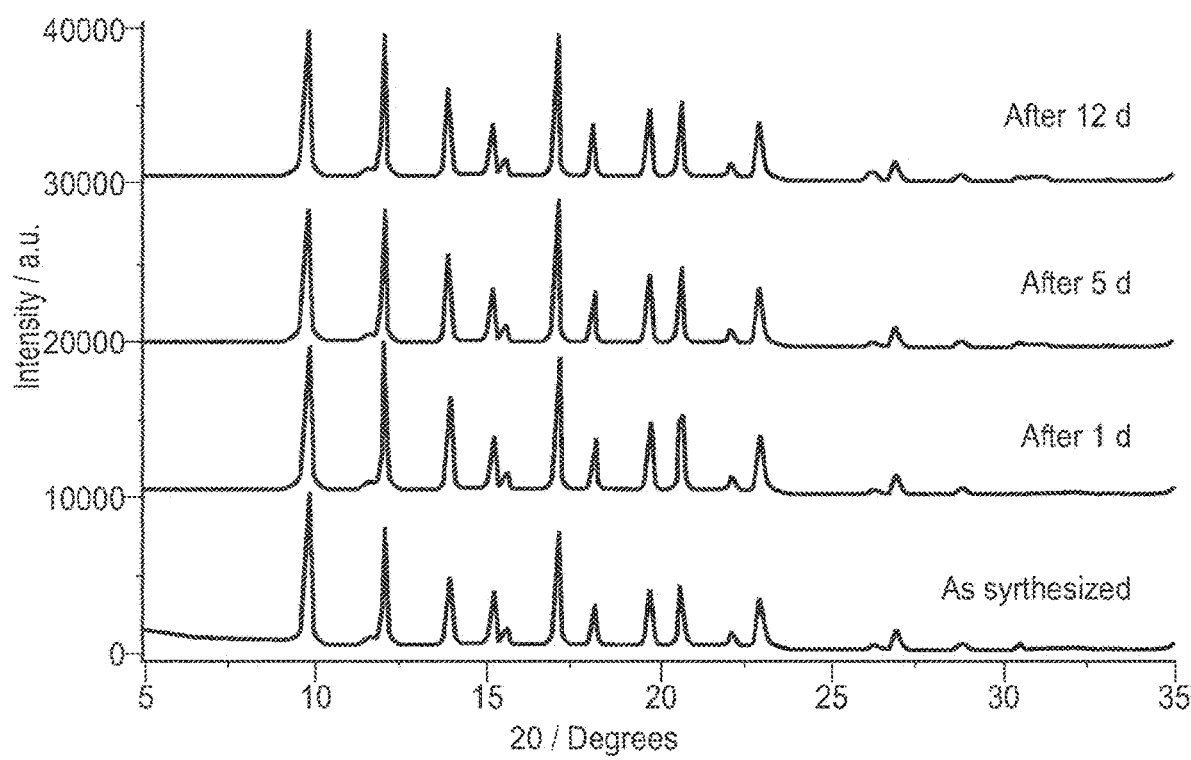
FIG. 7 shows a PXRD of FT-RCC3 after immersion in 0.02 M NaOH (pH=12.3) at room temperature. There is no apparent loss of crystallinity after 12 days.

FIG. 7 shows a PXRD of FT-RCC3 after immersion in 0.02 M NaOH (pH=12.3) at room temperature. There is no apparent loss of crystallinity after 12 days.

FT-RCC3 Binding Benzoic Acid in CHCl$_3$

Figure 8:
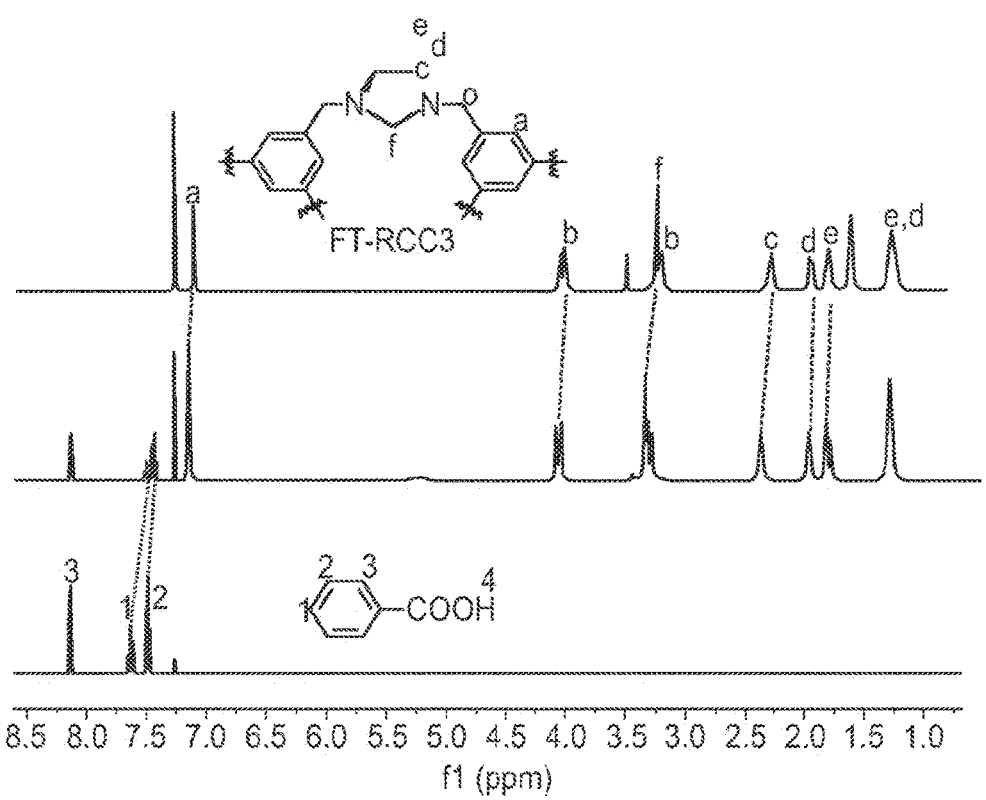
FIG. 8 shows an $^1$H NMR of FT-RCC3 (top), benzoic acid (bottom) and their mixture (middle).

FIG. 8 shows an $^1$H NMR of FT-RCC3 (top), benzoic acid (bottom) and their mixture (middle).

Figure 9:
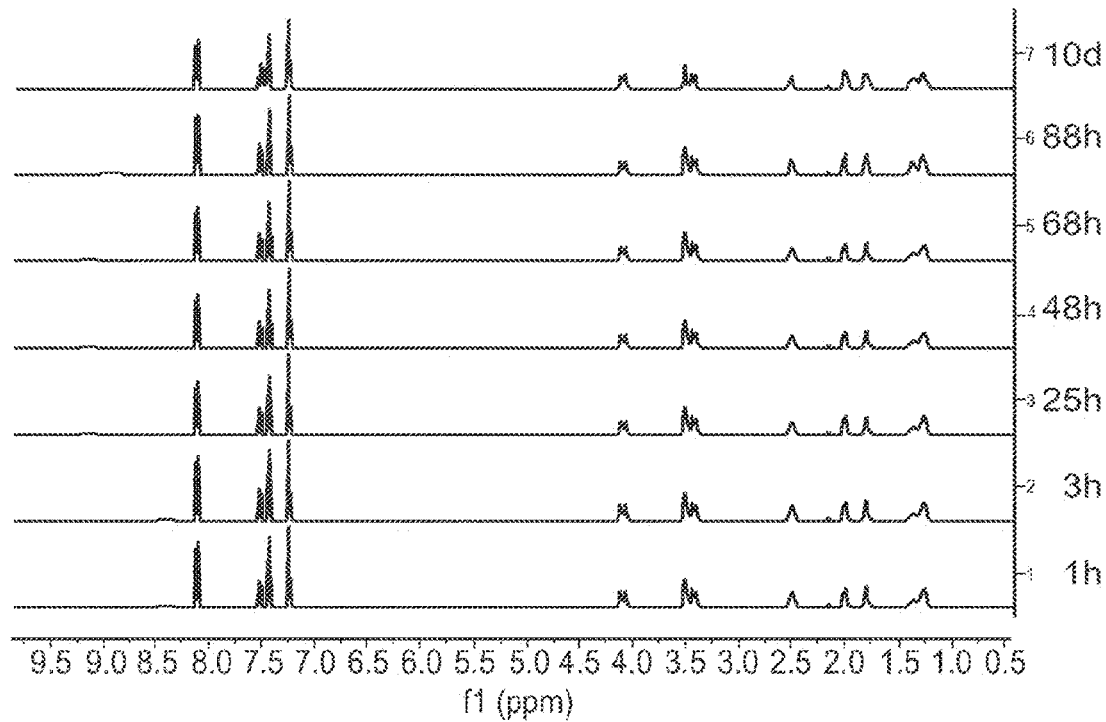
FIG. 9 shows an $^1$H NMR of FT-RCC3 with benzoic acid (20 mM·$L^{-1}$) in $CDCl_3$ at 25° C.

FIG. 9 shows an $^1$H NMR of FT-RCC3 with benzoic acid (20 mM·L$^{-1}$) in CDCl$_3$ at 25° C.

FIG. 10 shows graphical Job plots, which suggest the 1:1 stoichiometry of the complex benzoic acid∩FT-RCC3 in CHCl$_3$ by plotting the chemical shift changes of H$_1$ against the mole fraction of the guest. [H]$_0$ and [G]$_0$ are initial concentrations of FT-RCC3 and benzoic acid. [H]$_0$+[G]$_0$=5.00 mM.

FIG. 11 shows (a) Partial $^1$H NMR of benzoic acid (1.00 mM) upon addition of FT-RCC3. (b) The chemical shift changes of H$_1$ on benzoic acid upon addition of FT-RCC3. The red solid line was obtained by non-linear curve-fitting.

FT-RCC3 was found to bind benzoic acid (pK$_a$=4.2) as a guest in CHCl$_3$. It was found that proton signals of the host, FT-RCC3, and the guest molecule, benzoic acid, were shifted when they were mixed in a CDCl$_3$ solution (FIG. 8). A relative m/z peak of 1352.8 was found in the electrospray ionization mass spectra of the complex, which corresponds the calculated m/z for the ternary complex [FT-RCC3+benzoic acid+H$_3$O]$^+$. Under these conditions, there was no evidence of FT-RCC3 decomposition, even in the presence of 20 M benzoic acid for a period of 10 days, as judged from the integration of the $^1$H NMR signals (FIG. 9). Job plots confirm a 1:1 host guest stoichiometry between FT-RCC3 and benzoic acid in $CHCl_3$ by plotting the chemical shift changes of $H_1$ against the mole fraction of the guest (FIG. 10). The association constant (Ka) of benzoic acid ⊃ DFT-RCC3 was determined to be $9.1 \times 10^3$ $M^{-1}$ in $CDCl_3$ (FIG. 11).

Results and Discussion for Examples 1 to 3

Here we report a protocol to stabilize flexible amine cages and to produce shape-persistent, chemically stable amines that are porous in the solid state. The shape persistence of the parent imine cage is regained by reaction with a suitable 'tie' molecule on the cage vertices. Remarkably, the tied porous crystal is highly stable, even to prolonged treatment in acid or base.

The amine cage that we investigated was RCC3 (FIG. 1), a reduced derivative of the parent, chiral imine cage, CC3, which has tetrahedral symmetry (point group 7) and which is formed by the cycloimination of 1,3,5-triformylbenzene and (1R, 2R)-1,2-diaminocyclohexane.[3a] CC3 is readily prepared on a large scale (>100 g) in a one-pot condensation reaction, and it has an apparent Brunauer-Emmett-Teller (BET) surface area of ~400 $m^2$ $g^{-1}$ in highly crystalline form.[17] CC3 was reduced to the corresponding dodecaamine cage, RCC3, by treatment with $NaBH_4$ in close to 100% yield. Single crystal X-ray diffraction (SC-XRD) for a solvated crystal of RCC3 revealed that the molecule retains the tetrahedral shape of the parent imine cage, CC3, providing that methanol and $H_2O$ guests fill the pores in the structure.

FIG. 12 shows (a) Single crystal structure of RCC3 solvate with $H_2O$/methanol guests shown in red; (b) Representative energy-minimized model of a collapsed, desolvated RCC3 amine cage.

The more flexible amine bonds in RCC3 are no longer planar with the adjacent benzene ring, as for CC3, but point away from the cage cavity at an angle of 10° from the benzene plane. RCC3 packs in a window-to-window fashion, like the imine cage CC3. This could, in theory, produce an isostructural interconnected diamondoid pore network with the cage molecules acting as tetrahedral nodes. However, multiple attempts to desolvate RCC3, either by slow drying, solvent exchange, or supercritical fluid drying, all resulted in amorphous solids (FIG. 13).

Figure 13:
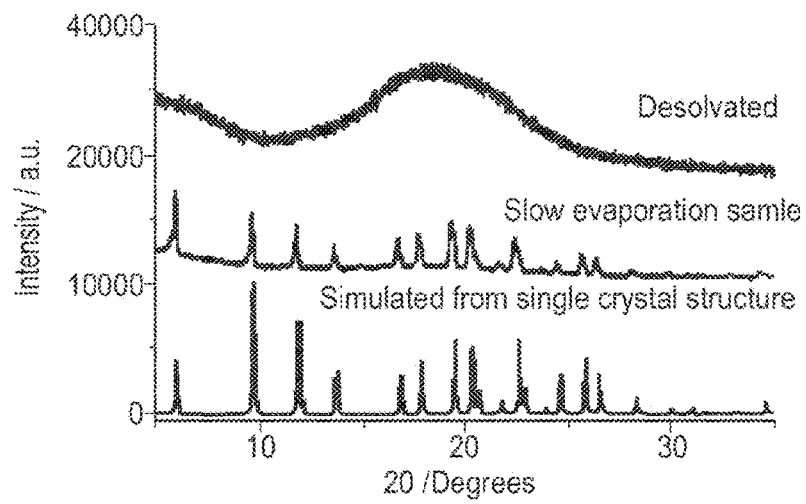
FIG. 13 shows Powder X-ray diffraction patterns for samples of RCC3: (lower) simulated from single crystal structure; (middle) RCC3 solvate, as crystallised from $CHCl_3$ solution; (top) desolvated RCC3 solid after activation (above).

FIG. 13 shows Powder X-ray diffraction patterns for samples of RCC3: (lower) simulated from single crystal structure; (middle) RCC3 solvate, as crystallised from $CHCl_3$ solution; (top) desolvated RCC3 solid after activation (above).

Unlike CC3, desolvated RCC3 did not exhibit any porosity to either $N_2$ or $H_2$ at 77 K, or to $CO_2$ at 298 K. By contrast, CC3 is also porous in the amorphous state: more porous, in fact, than in its crystalline form.[17] We therefore ascribe the loss of porosity in RCC3 to collapse of its flexible cage cavity upon desolvation, rather than to it being amorphous.

We have used computational conformer searching previously to predict the size and conformation of molecular imine cages.[18] Here, we use this approach to investigate the shape persistence of various amine cages. For RCC3, conformer searches confirmed the collapse of the molecular structure, with multiple possible collapsed conformations within a few kJ $mol^{-1}$ of each other, all lying significantly lower (>100 kJ $mol^{-1}$) in energy than the open void conformation that is stabilized by solvent in the RCC3 solvate (FIG. 12a). A representative example of a collapsed RCC3 conformation is shown in FIG. 12b, where the flexibility of the amine cage allows one arene face to 'fold' into the cage cavity, and therefore to occupy the original void space.

RCC3 is readily soluble in acetone. Surprisingly, we observed the spontaneous formation of prism-shaped single crystals from acetone solutions of RCC3 after about 30 minutes. These crystals were collected and characterized by NMR spectroscopy, mass spectrometry, elemental analysis, and SC-XRD. All characterization data suggested that just one of the six diamine vertices on each RCC3 cage had reacted with acetone to afford a new molecule, AT-RCC3 (where AT='acetone tied'), by formation of a 5-member imidazolidine (aminal) ring (FIG. 1). The geometry of the chiral (1R, 2R)-1,2-diaminocyclohexanediamine in RCC3 promotes formation of a 5-member imidazolidine ring. This is consistent with previous reports of aminal formation from secondary diamines and carbonyls.[19] AT-RCC3 crystallizes in the chiral cubic space group $F4_132$, like CC3,[3a] with comparable cell parameters. SC-XRD reveals that AT-RCC3 has tetrahedral symmetry and that the single imidazolidine ring is disordered over the six diamine vertices. To confirm that no further diamine vertices could be functionalized, this 'reactive recrystallization' was repeated at higher temperature (50° C.) using a cosolvent ($CHCl_3$/acetone, 1:1 v/v) for 24 h: again, reaction occurred at just one diamine vertex. We believe that the first acetone 'tie' prevents a second acetone molecule from reacting in the cage, probably by steric inhibition of intermediates. The solubility of AT-RCC3 in acetone was also significantly decreased compared with RCC3, and AT-RCC3 precipitated from solution upon formation. This drives the reversible aminal formation reaction by removing the aminal product from equilibrium, explaining the almost 100% conversion of RCC3 to AT-RCC3. As a side benefit, this reversible acetone/RCC3 reaction constitutes a simple and effective method to purify RCC3 by (i) forming the aminal; (ii) filtering; (iii) redissolving, and; (iv) reversing the aminal reaction to regenerate the amine cage.

While AT-RCC3 is unstable in solution, allowing the purification process described above, the solvate of AT-RCC3 is stable as a crystalline solid up to around 300° C. The chemical composition and crystallinity of the AT-RCC3 solvate was also retained after water immersion for 48 h. Unlike RCC3 which becomes amorphous, AT-RCC3 retained most of its crystallinity when desolvated, as shown by PXRD (Figure Se). A single crystal was also desolvated in situ by gradually increasing the sample temperature. The structure at 350 K shows a shape-persistent, solvent-free cage where the single acetone 'tie' in each cage prevents collapse.

Figure 14:
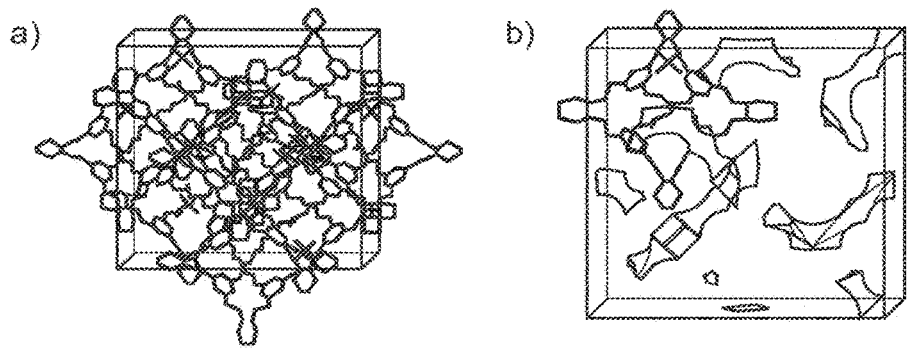
FIG. 14 shows (a) Crystal packing for shape-persistent AT-RCC3; the ties are shown in red, otherwise C (gray), N (blue) and H (omitted). The ties were positionally disordered (randomized) in this structural model; (b) The solvent accessible surface for AT-RCC3 generated using a probe radius of 1.82 Å for $N_2$ using Zeo++.[20] A single AT-RCC3 molecule is shown. The formally disconnected voids are shown in orange. The acetone tie blocks its two neighbouring windows for the $N_2$ probe in each cage.

FIG. 14 shows (a) Crystal packing for shape-persistent AT-RCC3; the ties are shown in red, otherwise C (gray), N (blue) and H (omitted). The ties were positionally disordered (randomized) in this structural model; (b) The solvent accessible surface for AT-RCC3 generated using a probe radius of 1.82 Å for $N_2$ using Zeo++.[20] A single AT-RCC3 molecule is shown. The formally disconnected voids are shown in orange. The acetone tie blocks its two neighbouring windows for the $N_2$ probe in each cage.

Figure 15:
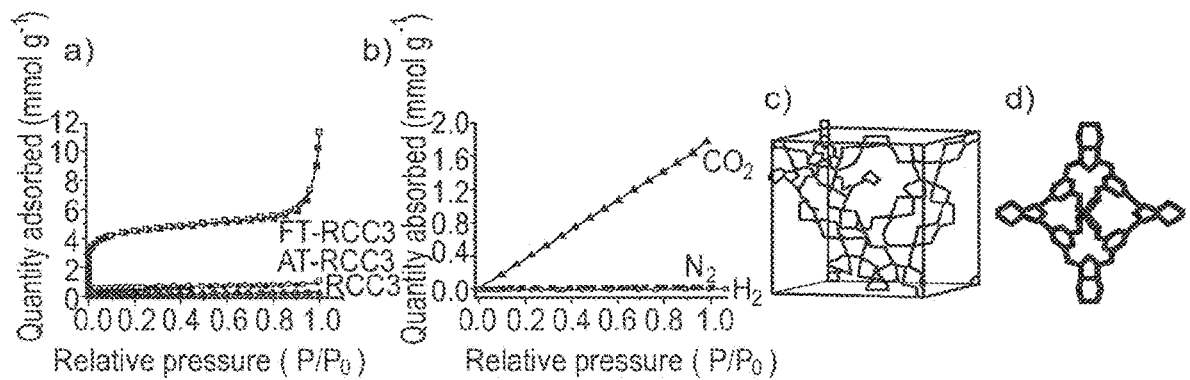
FIG. 15 shows (a) $N_2$ adsorption/desorption isotherms at 77 K showing a substantial increase in porosity for FT-RCC3 vs AT-RCC3 and RCC3. Solid symbols=adsorption; open symbols=desorption; (b) Carbon dioxide (navy triangles), nitrogen (black squares) and hydrogen (blue circles) adsorption isotherms for AT-RCC3 at 298 K; (c) The solvent accessible surface for FT-RCC3 using a probe radii of 1.42 Å for $H_2$, showing an interconnected 3D diamondoid pore network; (d) Overlay of the calculated lowest energy structure (red) and single crystal X-ray diffraction structure for a solvate of FT-RCC3 (blue; solvent molecules omitted for clarity).

FIG. 15 shows (a) $N_2$ adsorption/desorption isotherms at 77 K showing a substantial increase in porosity for FT-RCC3 vs AT-RCC3 and RCC3. Solid symbols=adsorption; open symbols=desorption; (b) Carbon dioxide (navy triangles), nitrogen (black squares) and hydrogen (blue circles) adsorption isotherms for AT-RCC3 at 298 K; (c) The solvent accessible surface for FT-RCC3 using a probe radii of 1.42 Å for $H_2$, showing an interconnected 3D diamondoid pore network; (d) Overlay of the calculated lowest energy structure (red) and single crystal X-ray diffraction structure for a solvate of FT-RCC3 (blue; solvent molecules omitted for clarity).

Like CC3, desolvated AT-RCC3 packs in a window-to-window fashion (FIG. 14). Gas adsorption analysis for desolvated AT-RCC3 (FIG. 15a) showed that the material adsorbs a very modest amount of $N_2$ (1.11 mmol $g^1$) and $H_2$ (1.29 mmol $g^{-1}$) at 77 K and 1 bar. The apparent BET surface area was just 67 $m^2 g^{-1}$, as calculated from the $N_2$ isotherm. This surface area and gas uptake is substantially lower than for isostructural CC3.[3a] However, close to ambient temperature, a $CO_2$ uptake of 1.77 mmol $g^{-1}$ was observed for AT-RCC3: that is, eight times higher than for RCC3 (FIG. 15b). The ideal gas selectivity for $CO_2$/N2 was calculated as 57 at 298 K and 1 bar. This is close to the $CO_2/N_2$ selectivity of the [2+3] imine cages reported by Zhang et al.,[15] but with a much higher absolute $CO_2$ uptake (1.77 mmol $g^{-1}$ for AT-RCC3 vs 0.1-0.25 mmol $g^1$ for the Zhang cages). The lack of $N_2$ and $H_2$ adsorption at low temperature in AT-RCC3 is explained by its crystal structure. The solvent accessible surface with a $N_2$ probe radius of 1.82 Å[21] shows formally disconnected voids (FIG. 14b). This is because the dimethyl groups block two of the four windows on each AT-RCC3 cage. The interconnectivity of the pore structure for $N_2$ thus depends upon the spatial arrangement of these dimethyl-blocked windows with respect to one another.

This disconnects the pore volume (FIG. 14b), particularly at low temperatures where molecular motion and dynamic cooperative diffusion are less prevalent. At higher temperatures, it is possible that thermal motion allows gases to negotiate these blocked pathways. The five remaining unreacted diamine groups per cage molecule may promote $CO_2$ adsorption,[13,22] and this could account, in part, for the high $CO_2/N_2$ selectivity in AT-RCC3.

Reaction with a single acetone rigidifies the amine cage relative to RCC3, but AT-RCC3 is still too flexible to retain permanent porosity over a timescale of days. A slight loss in crystalline order was observed after desolvation, and a further loss of crystallinity was apparent after gas sorption analysis. In addition, after exposing AT-RCC3 to $CO_2$ (5 bar), we found evidence for a second single crystal phase, not evident in the as-synthesized material. This phase comprised a collapsed conformation of AT-RCC3 where the imidazolidine ring preferentially collapses into the cage cavity. It is clear, therefore, that tying just one diamine vertex in the RCC3 molecule does not give sufficient rigidity to enable applications such as gas separation, which involve repeated adsorption/desorption steps. Improved shape persistence might be expected if we tied all six diamine vertices, rather than just one, but this rules out bulky tie-molecules because (i) they cannot react at all six diamine sites due to space constraints, and (ii) bulky ties will occupy too much of the void space, and hence eliminate porosity.

The candidate 'tie' selected was formaldehyde. A white precipitate formed immediately when RCC3 and paraformaldehyde were mixed together at 70° C. in methanol. FT-RCC3 (where FT=formaldehyde tied) was recovered in 70% yield after washing with methanol and drying. NMR spectroscopy of the product suggested that all six diamine groups in RCC3 had reacted with formaldehyde, as also proven by SC-XRD (FIG. 15c,d).

FT-RCC3 retains the tetrahedral symmetry of the imine, CC3, and crystallizes in F4₁32 with similar cell parameters (Table 1). SEM imaging of the as-synthesized material showed homogeneous crystals with an average size of 10 μm (FIGS. 2 and 3). The FT-RCC3 material can be fully desolvated under dynamic vacuum for 12 h at 80° C. Unlike AT-RCC3, there was no indication of any loss of crystallinity for FT-RCC3 after either desolvation or after gas adsorption, a promising indicator of increased shape persistence (FIGS. 4 and 5). The porous nature of FT-RCC3 was next probed by $N_2$, $H_2$ and $CO_2$ adsorption. Nitrogen adsorption measurements at 77 K showed a Type I isotherm (FIG. 15a) with a total gas uptake of 11.2 mmol $g^{-1}$ at 1.0 bar and an apparent BET surface area of 377 $m^2 g^{-1}$. This is only slightly lower than the 409 $m^2 g^{-1}$ measured for the parent imine cage, CC3.[17] However; both materials have precisely the same 'molar' BET surface area of 457 $m^2$ $mmol^{-1}$ when their molecular weights are considered. FT-RCC3 adsorbs 4.3 mmol $g^{-1}$ of $H_2$ at 77 K and 1.0 bar, and 1.42 mmol $g^{-1}$ of $CO_2$ at 298 K and 1 bar. As can be seen from the calculated solvent accessible surface (FIG. 15c), the pores in FT-RCC3 are interconnected for a 1.42 Å $H_2$ probe. This interconnectivity persists for a smaller 1.55 Å probe (equivalent to a $N_2$ molecule oriented end-on), but becomes formally disconnected for a $N_2$ van der Waals radius probe of 1.82 Å. We assume that breathing motions of the molecule allow for diffusion of $N_2$ through the pore structure, as observed for CC3.[23]

A conformational search for FT-RCC3 found that the lowest energy conformer was the observed shape-persistent structure, comprising a permanent void (FIG. 15d). A partially folded conformation (FIG. 6) was also found to lie 22 kJ $mol^{-1}$ higher in energy, as calculated with the OPLS-AA forcefleld.[24] DFT calculations confirmed that the open structure was indeed the lowest energy molecular structure, with an energy gap of 14 kJ $mol^{-1}$. An overlay of the calculated molecular structure with the experimental structure (FIG. 15d) shows excellent agreement, with a RMSD of 0.079 Å (excluding hydrogens).

Most imine-based molecules are unstable in acidic or basic environments, or even in the presence of neutral water. The crystalline parent imine cage, CC3, is surprisingly robust to neutral water,[11] but it decomposes rapidly when immersed in mildly acidic solutions.

Figure 16:
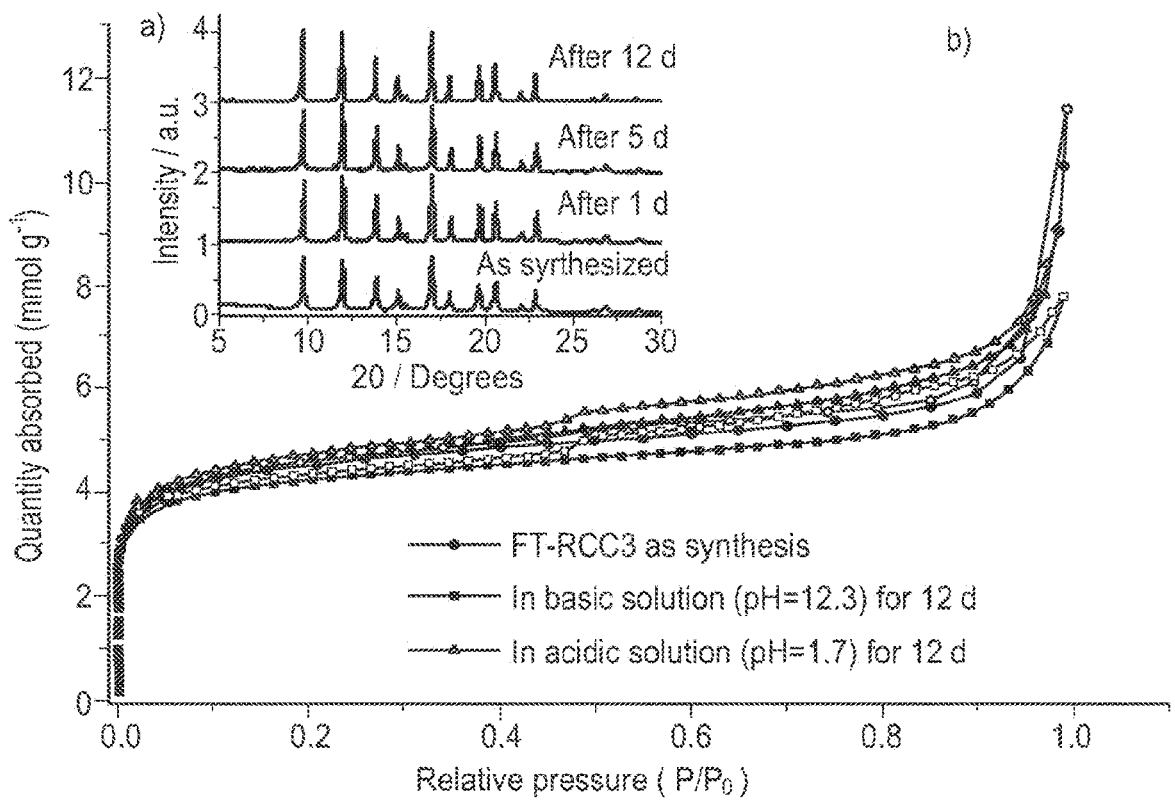
FIG. 16 shows (a) PXRD patterns for FT-RCC3 after immersion in 0.02 M HCl (pH=1.7) for 12 days. (b) $N_2$ isotherms at 77 K as synthesized (black circles), and after treatment with basic (blue squares) or with acidic solution for 12 days (red triangles). Solid symbols show adsorption and open symbols desorption.

FIG. 16 shows (a) PXRD patterns for FT-RCC3 after immersion in 0.02 M HCl (pH=1.7) for 12 days. (b) $N_2$ isotherms at 77 K as synthesized (black circles), and after treatment with basic (blue squares) or with acidic solution for 12 days (red triangles). Solid symbols show adsorption and open symbols desorption.

FT-RCC3 showed excellent stability toward water and also to both acids and bases. There was no loss of crystallinity, nor any chemical decomposition, when solid FT-RCC3 was soaked in either acidic (pH=1.7; FIG. 16a) or

TABLE 1

| Unit cell parameters for cages (T = 100 K). | | | | |
|---|---|---|---|---|
| | CC3 | RCC3 | AT-RCC3 | FT-RCC3 |
| a (Å) | 25.016(2) | 25.71(1) | 25.469(1) | 25.316(2) |
| V (Å³) | 15090(12) | 16999(13) | 16520(2) | 16225(2) | basic (pH=12.3; FIG. 7) solutions for 12 days. Likewise, these acid/base treatments did not affect the porosity in the material, as shown by the $N_2$ isotherms after treatment (FIG. 16b). This stability also translates to FT-RCC3 in solution. For example, we found that FT-RCC3 can bind benzoic acid in $CHCl_3$ solution with an association constant of $9.1 \times 10^3$ $M^{-1}$. No sign of decomposition in the tied cage was observed after 10 days in this acidic solution (FIGS. 8-11). Such host-guest binding in acidic media would be impossible for the imine cage, CC3. The inner cavity of FT-RCC3 becomes more hydrophobic compared with RCC3 after decoration with 6 methylene groups, but FT-RCC3 can still bind or adsorb polar guests such as water or benzoic acid. We therefore ascribe the enhanced stability of FT-RCC3 to its more robust chemical bonding, rather than to simple exclusion of the acid or base species from the molecular pores.

In summary, we have demonstrated a new protocol for stabilizing flexible amine cages. By tying the cage vertices with small carbonyl molecules, the shape-persistence of the cage can be greatly improved. We illustrate this here using reactions between diamines and ketones or aldehydes, and the reaction is potentially transferable to other cages prepared from vicinal diamine building blocks.[7] By choosing suitable ties, molecular collapse can be prevented and permanent, solid-state porosity can be retained. Moreover, when formaldehyde is used as the tie, the resulting molecule has far better physicochemical stability than the parent imine cage. This strategy could have important practical applications. Some amorphous porous materials, such as activated carbon and porous organic polymers,[25] are stable to both acids and to bases. By contrast, crystalline porous solids are rarely stable over such a broad pH range: most zeolites, MOFs, and COFs, are attacked by either acids or bases, or both. As such, FT-RCC3 exhibits a level of chemical and crystal stability that is so far unmatched by other crystalline molecular 'organic zeolites'.

Example 4—Dual Sorption of Formaldehyde with RCC3 of Example 1

RCC3 was prepared as described in Example 1, followed by desolvation under vacuum for 24 h, 80° C.

Once prepared, a sample of the collapsible substrate, RCC3, was hermetically sealed in an atmosphere (at 1 Bar) of air containing (100 ppm) of gaseous formaldehyde at a temperature of 25° C., a humidity of 30% for a period of 24 h. After this time, the composition of the atmosphere was examined using GCMS headspace experiment. It was noted that substantially all of the formaldehyde within the atmosphere had been removed.

Upon subsequent examination of the formaldehyde-contacted collapsible substrate (by solution NMR) it was noted that the collapsible substrate had become a sorption complex with formaldehyde both chemisorbed and physisorbed therein. The inventor's have calculated that the overall uptake of formaldehyde was 200 $cm^3/g$ of collapsible substrate.

The sorption complex was then subjected to thermogravimetric analysis to determine the temperature at which formaldehyde was ultimately liberated from the sorption complex. It was noted that substantially no formaldehyde was liberated until 300° C. After prolonged heating at 300° C., subsequent analysis (thermogravimetric analysis and solution NMR) of the post-heated sorption complex revealed that chemisorbed formaldehyde was retained whilst physisorbed formaldehyde was removed. As such, the inventors concluded that the chemisorption of formaldehyde effectively increased the porous material's affinity for formaldehyde over and above what was expected.

Example 5—Sorption of Radon with FT-RCC3 of Example 3

FT-RCC3 was prepared as described in Example 3, followed by desolvation under vacuum for 24 h, 80° C.

Once prepared, a sample of the stabilized porous material, FT-RCC3, was used to evaluate the radon-adsorption capabilities thereof.

Figure 17:
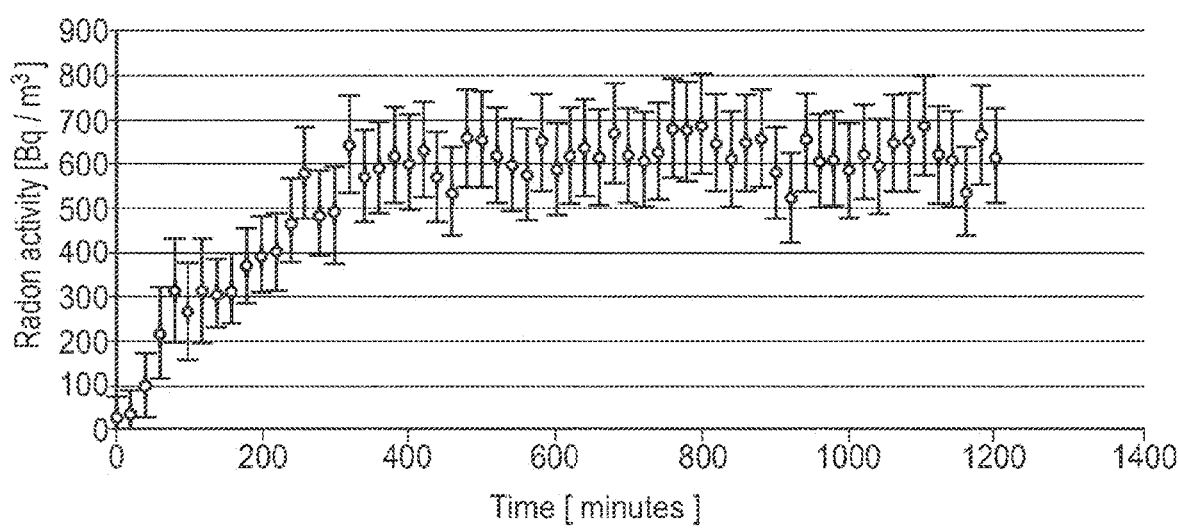
FIG. 17 shows a saturation curve for Rn (at high dilution in $N_2$) adsorbed on FT-RCC3.

FIG. 17 shows a saturation curve for Rn (at high dilution in $N_2$) adsorbed on FT-RCC3.

Figure 18:
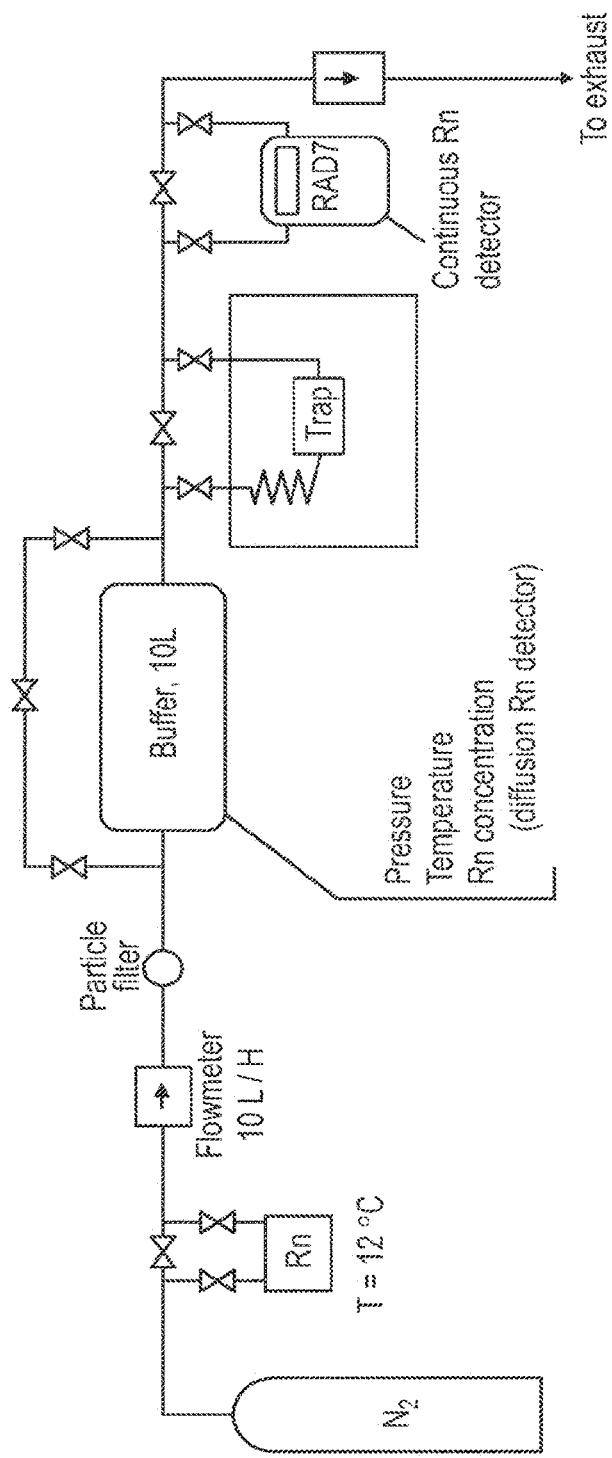
FIG. 18 is a scheme showing apparatus used for Rn adsorption measurements.

FIG. 18 is a scheme showing apparatus used for Rn adsorption measurements.

The radon adsorption ability of FT-RCC3 was evaluated using a dynamic adsorption technique as now described. The most stable naturally-occurring isotope of radon, $^{222}Rn$, still has a relatively short half-life (~3.82 days) and thus, for the purposes of these experiments (and to best simulated atmospheric radon), must be diluted with a carrier gas to a very low concentration. The carrier gas, with a fixed concentration of radon, is then injected into an adsorbent trap. Adsorption equilibrium is achieved when the breakthrough curve (see FIG. 17) reaches a constant value or asymptote. Under such conditions, the ratio between the number of atoms of radon trapped and the radon concentration in the gas, both assumed to be proportional to their respective activity (becquerel per meter cube, $Bq\ m^{-3}$), is given by the equilibrium constant, K:

$$K = \frac{\{A\}}{\{C\}}$$

where {A} is the radon activity in FT-RCC3 and {C} is the radon activity in the gas.

The complete experimental setup is illustrated in FIG. 18. The nitrogen carrier gas is radonised in the radon source by emanation from a metal plate coated with a thin radium layer and maintained at a fixed temperature (12° C.). The mean radon concentration in the carrier gas is 615±17 $Bq\ m^{-3}$ (3.8±0.1·$10^{-1}$ $mol\ kg^{-1}$). The gas is introduced into a buffer tank in which the radon concentration (C), the temperature, and the pressure are controlled. Thereafter, the carrier gas, with a well-defined amount of radon, is introduced into the column trap, which may be located in a freezer for low temperature experiments. In order to define the equilibrium capture in the radon trap, the output gas is measured with a commercial RAD7 detector calibrated for a continuous nitrogen flow. Once equilibrium is reached, the trap is disconnected from the gas circuit and the $^{222}Rn$ activity of the FT-RCC3 sample is measured by gamma spectrometry in a germanium detector from the main gamma lines of radon progeny (352 keV from $^{214}Pb$ and 609 keV from $^{214}Bi$).

Though further analytical work remains to be conducted with respect to radon adsorption experiments, the inventors were surprised by their initial findings which suggest that FT-RCC3 adsorbs $^{222}Rn$ from the gas phase by a volumetric factor of at least 5,000 at 20° C. At the same temperature, initial findings suggest that the "K factor" of FT-RCC3 with respect to Rn is approximately 5-7 $kg/m^3$, that the concentration of radon within the FT-RCC3 material is approximately 2.3-3.3×$10^{-15}$ mol/kg, and that the activity of FT- RCC3 is approximately 3-4×10³ Bq/kg. This represents excellent selectivity for Rn over $N_2$ at 20° C.

It is therefore reasonable to conclude that the sorption compositions, and stabilised porous materials, of the invention may serve as a useful tool for removing harmful radioactive radon from air or even water (where it is found dissolved therein). Furthermore, the sorption complexes of the invention produced through radon adsorption may themselves serve as analytical tools for environmental analysis.

Figure 19:
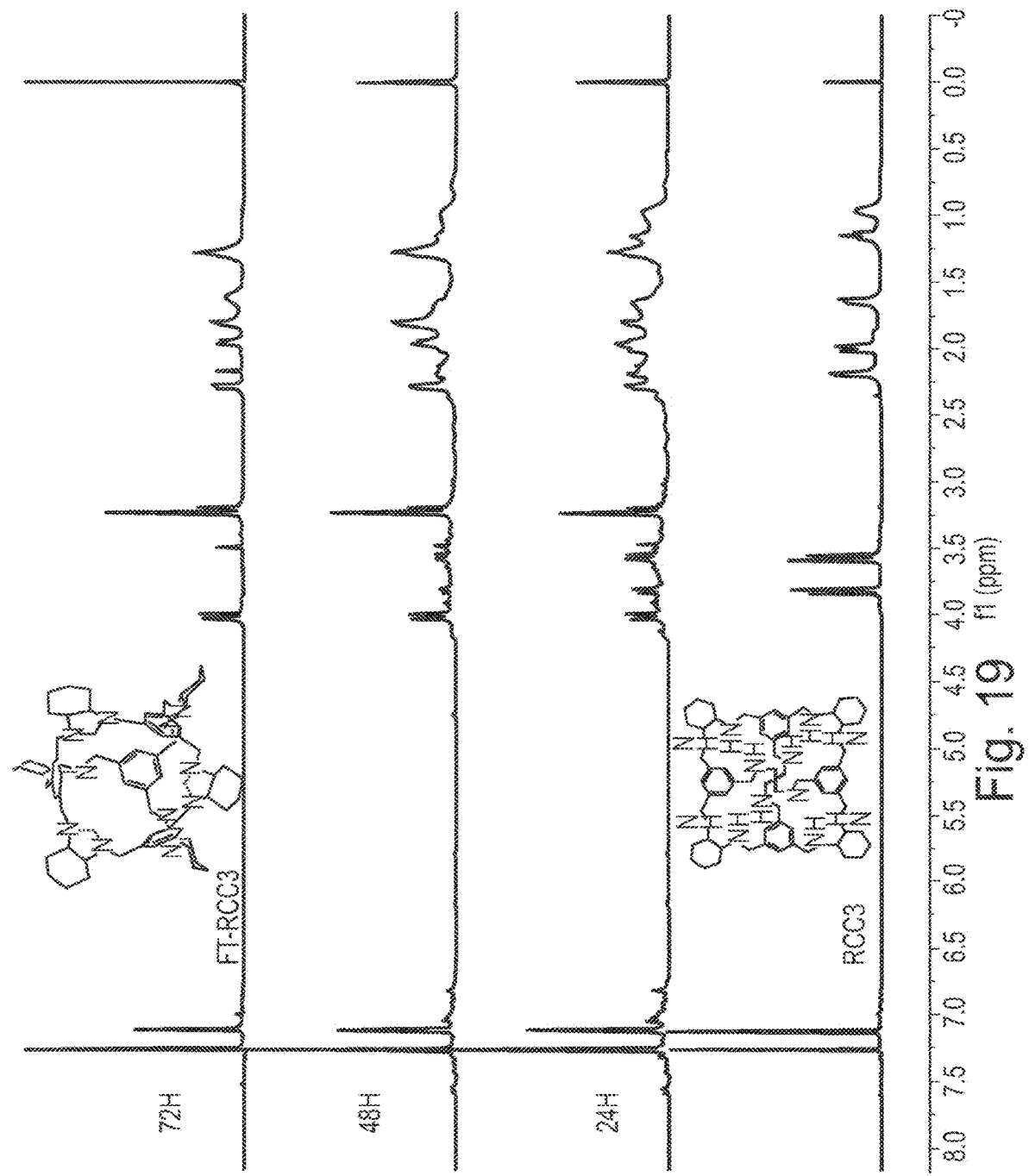
FIG. 19 is an $^1$H NMR spectrum showing that, after being exposed to gaseous formaldehyde, RCC3 gradually transformed to FT-RCC3 by chemically absorbing 6 formaldehyde molecules.

Example 6—Further Examples of Chemisorption, Physisorption and Selective Sorptions of Formaldehyde by RCC3 and Radon by FT-RCC3 Complexes RCC3 Chemically Absorbs Gaseous Formaldehyde Further experiments performed by the inventors confirmed that solid RCC3 could chemically absorb gaseous formaldehyde to generate FT-RCC3. As shown by FIG. 19, when exposed to gaseous formaldehyde, the ¹HNMR signals of RCC3 were decreasing and peaks related to FT-RCC3 increased. There are also new peaks appear which related to the non-fully-converted intermediates. These peaks will disappear when all RCC3 and intermediates transformed to FT-RCC3 after about 72 h.

Figure 20:
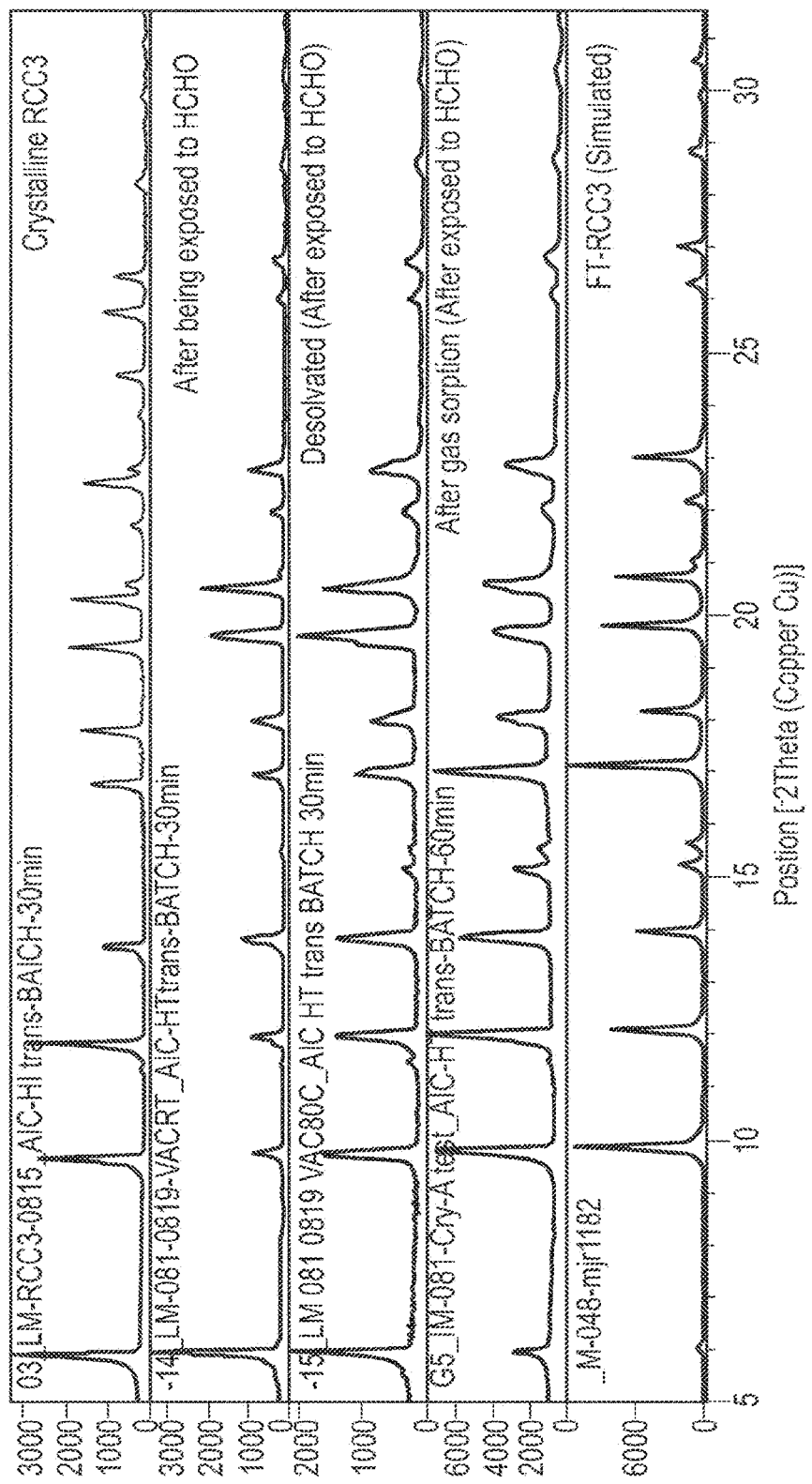
FIG. 20 shows powder X-ray diffraction patterns confirming RCC3 transformed to FT-RCC3 after being exposed to gaseous formaldehyde.

Powder X-ray diffraction experiments also confirmed that RCC3 converted to FT-RCC3 after being exposing to gaseous formaldehydes by "capture" 6 formaldehyde molecules (FIG. 20).

FIG. 19 is an ¹H NMR spectrum showing that, after being exposed to gaseous formaldehyde, RCC3 gradually transformed to FT-RCC3 by chemically absorbing 6 formaldehyde molecules.

FIG. 20 shows powder X-ray diffraction patterns confirming RCC3 transformed to FT-RCC3 after being exposed to gaseous formaldehyde.

The Formed "Tied Cage" can Further Physically Absorb Gaseous Formaldehyde

After chemically absorbing 6 formaldehyde molecules, the result materials FT-RCC3 is fairly porous as proven by the $N_2$ isotherm (FIG. 21a). TGA experiment further proved that FT-RCC3 could further absorb formaldehyde by physical adsorption (FIG. 21b).

Figure 21:
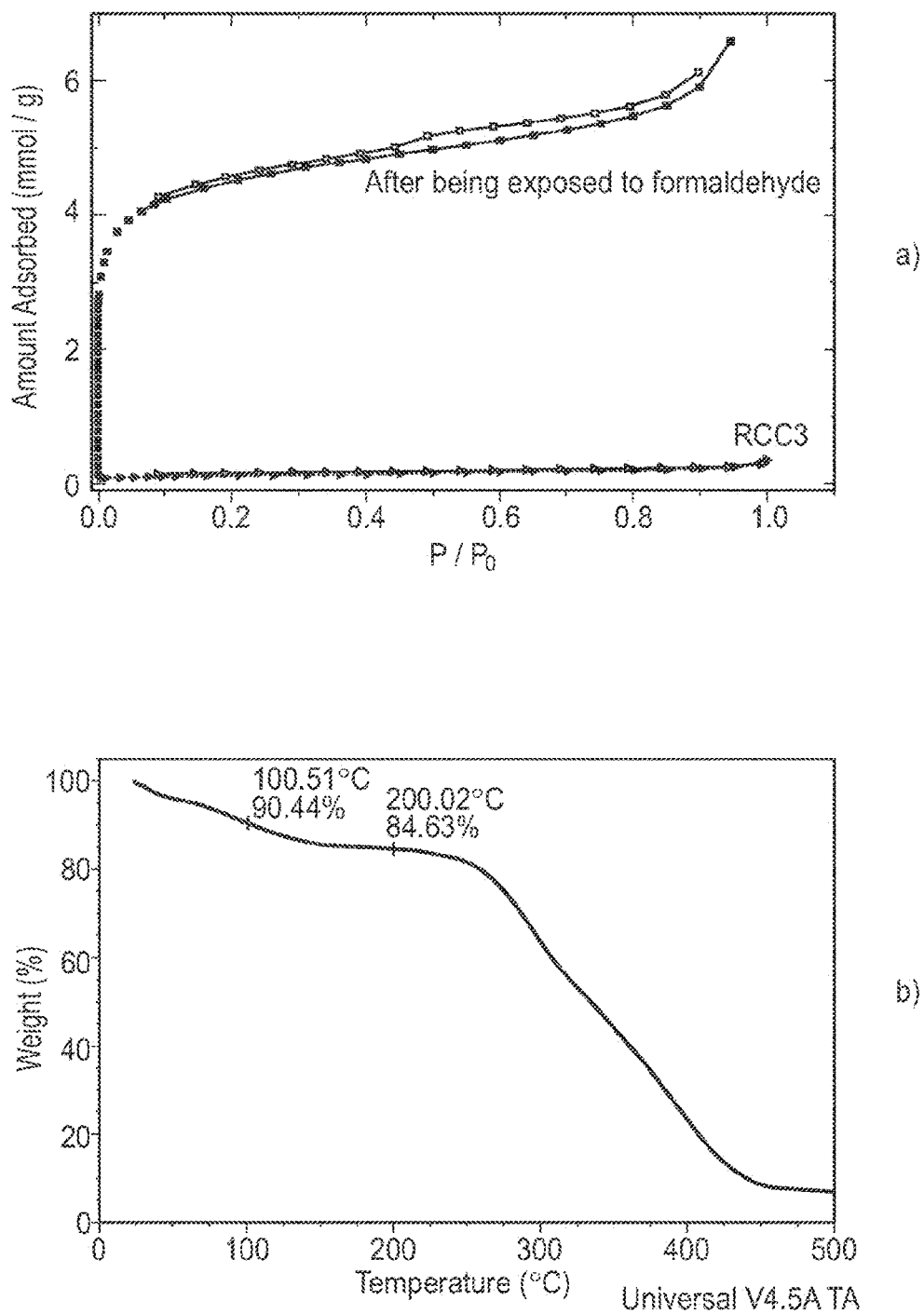
FIG. 21 shows a) an $N_2$ isotherm of product after chemically absorbing formaldehyde (FT-RCC3) at 77 K. b) TGA data of FT-RCC3 after being exposed to gaseous formaldehyde for 2 h.

FIG. 21 shows a) an $N_2$ isotherm of product after chemically absorbing formaldehyde (FT-RCC3) at 77 K. b) TGA data of FT-RCC3 after being exposed to gaseous formaldehyde for 2 h.

We used Grand-canonical Monte Carlo simulations to predict the physical adsorption of formaldehyde. For crystalline FT-RCC3 at ambient conditions, it was predicted that one unit cell could take up 24.7 formaldehyde molecules, which gives ~3 $CH_2O$ per cage. There is clear evidence of hydrogen bonding between an oxygen atom of $CH_2O$ and the hydrogen atom bonded to a carbon atom that is bonded to an amine nitrogen atom (i.e., the carbon atom can be either from a formaldehyde tie unit or bonded to a phenyl ring). It is interesting to note that the hydrogen atoms bonded to both types of carbon point toward the cage window, hence hydrogen bonding is mostly observed for the $CH_2O$ at a window cavity. Inside the cage, hydrogen bonding appears to be difficult to form (potentially because the C—H—O angle is not favourable). Nevertheless, there is strong electrostatic interaction between the hydrogen atoms of the tie unit (these H atoms are strongly positively charged due to the electron deficiency of the tie-unit carbon) and $O(CH_2O)$. In a word, both the inside and the "outer-sphere" of a cage are suggested to have strong affinity toward $CH_2O$.

The calculated heat of adsorption is high: ~40 kJ/mol for the loading of 24 $CH_2O$ per unit cell; it can be decomposed to host-guest and guest-guest contributions of ~24 and ~16 kJ/mol, respectively.

Figure 22:
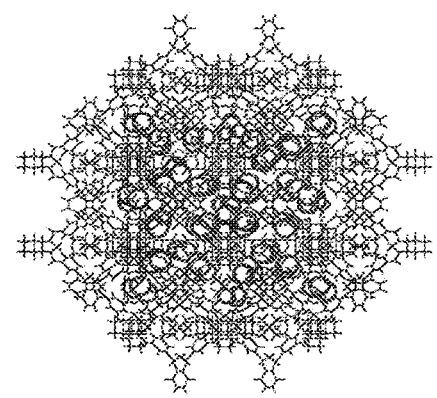
FIG. 22 illustrates a simulation of formaldehyde-adsorption of crystalline FT-RCC3.

FIG. 22 illustrates a simulation of formaldehyde-adsorption of crystalline FT-RCC3.

Figure 23:
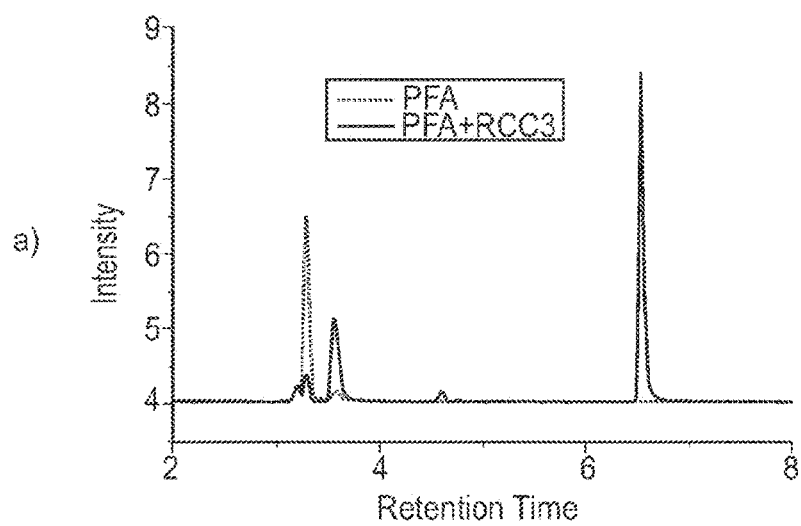
FIG. 23 shows GC traces from GC headspace experiments showing that: a) the peak related to formaldehyde disappeared when RCC3 was added; b) while when a porous imine cage CC3 was used, only a slight decrease of formaldehyde peak intensity was observed.
Figure 23:
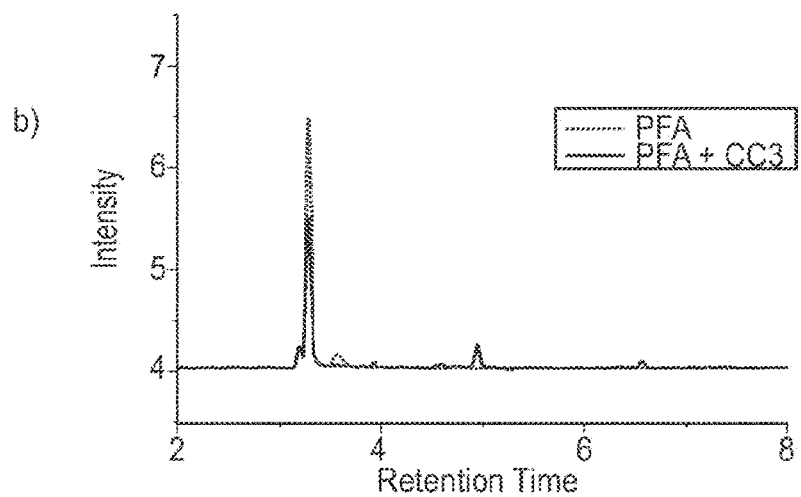

GC headspace experiments were performed in order to further prove RCC3 can efficiently capture low-concentration gaseous formaldehyde. As shown in FIG. 23, when a certain amount of RCC3 was added, the signal of formaldehyde in the GC trace almost disappeared. While when a similar cage molecule, CC3 (with a BET surface area about 400 m²/g) was added at the same amount, the formaldehyde signal only slightly decreased.[B1]

FIG. 23. shows GC traces from GC headspace experiments showing that: a) the peak related to formaldehyde disappeared when RCC3 was added; b) while when a porous imine cage CC3 was used, only a slight decrease of formaldehyde peak intensity was observed.

RCC3 can Selectively Absorb Formaldehyde Over $H_2O$

One of the biggest problems of the traditional formaldehyde adsorbents, such as activated carbon, is the formaldehyde adsorption capability decreased dramatically under humid conditions because of the poor formaldehyde/$H_2O$ selectivity of this material. Whereas, RCC3 will preferentially absorbing formaldehydes via reaction with pre-organized diamine groups. The presence of water will even benefit the chemical absorbtion because of the reversibility of the aminal formation. It can even absorb formaldehyde from an aqueous solution as showed in FIG. 24. When solid RCC3 was immersed in formaldehyde aqueous solution, it can be observed that the solid RCC3 will gradually turn into FT-RCC3 in 72 h as suggested by its proton NMR. It is clearly shown that RCC3 have an overwhelmingly selective of formaldehyde over $H_2O$.

Figure 24:
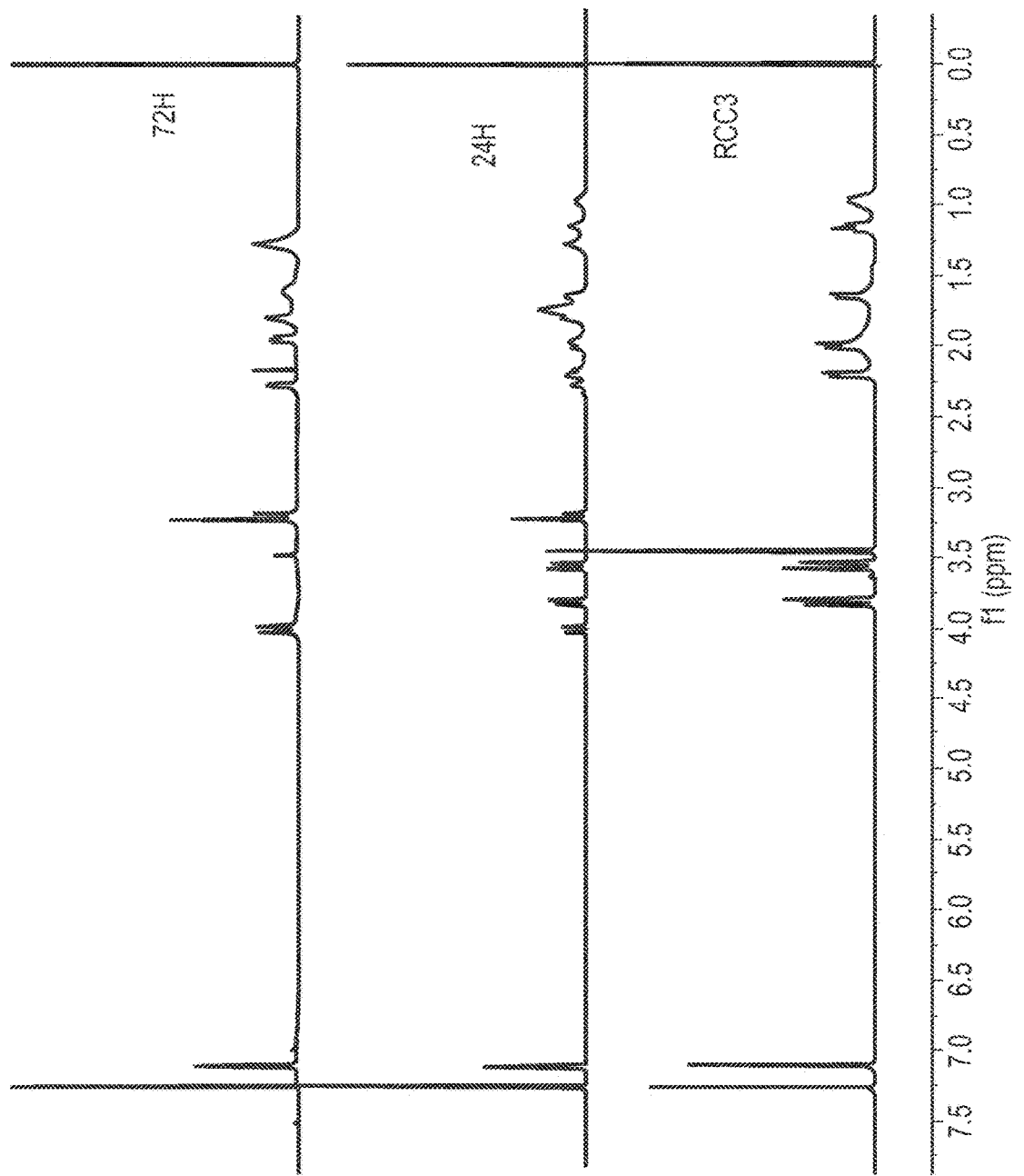
FIG. 24 is an $^1$H NMR spectrum showing that, after being immersed into aqueous formaldehyde, RCC3 gradually transformed to FT-RCC3.

FIG. 24 is an ¹H NMR spectrum showing that, after being immersed into aqueous formaldehyde, RCC3 gradually transformed to FT-RCC3.

After Chemically Absorbed Formaldehyde, the Formed FT-RCC3 can Absorb Low Concentration Radon Radon gas, which occurs naturally in a radioactive form (²²²Rn), can accumulate in buildings, and is a leading cause of lung cancer, accounting for around 21,000 deaths per year in the USA alone. Thus, radon is considered a significant contaminant that affects indoor air quality worldwide. At present, charcoal is used as an adsorbent for short-term radon testing in domestic homes, but its relatively poor selectivity against water vapour can lead to variation in test results with fluctuating humidity.

The parental imine cage of RCC3, CC3, has been proven to be an excellent adsorbent for radon gas.[B2] Experiments with radioisotopes are restricted to specialized laboratories, but radioisotope adsorption is readily studied in silico. Grand-canonical Monte Carlo simulations were used to predict the adsorption isotherm of radon and its removal, at low concentrations, from gas mixtures. We have predicted that CC3 could capture ²²²Rn from heliumat radon concentrations as low as 0.01 ppmv with extremely high selectivity (Rn/He=2.5×10⁸, FIG. 25a), as relevant in astroparticle physics experiments searching for rare, low-energy events. Whereas for FT-RCC3, in same condition, the selectivity (Rn/He) is 2.6×10⁸ (FIG. 25b), which is about 100 times higher than CC3.

Figure 25:
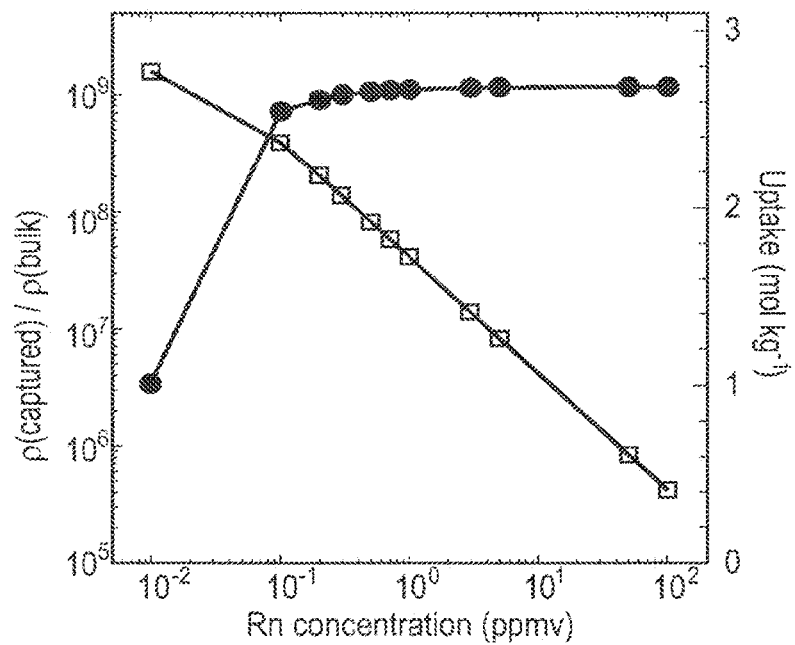
FIG. 25 illustrates simulated removal of low concentrations of Rn from binary (Rn—He) mixtures by (a) CC3 and (b) 6FT-RCC3, at a total pressure 1 bar at 193 K.
Figure 25:
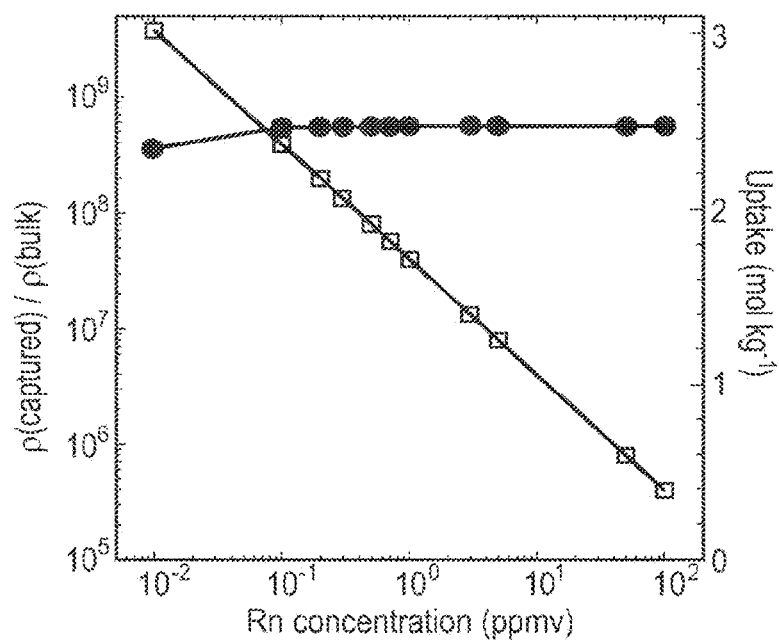

FIG. 25 illustrates simulated removal of low concentrations of Rn from binary (Rn—He) mixtures by (a) CC3 and (b) FT-RCC3, at a total pressure 1 bar at 193 K.

In each case, the volumetric density ratio of the rare gas in the porous adsorbent divided by its volumetric density in the bulk gas phase [ρ(captured)/ρ(bulk)] is plotted against its concentration in the gas mixture (left Y axis), together with the corresponding rare gas uptake by the adsorbent (right Y axis). FT-RCC3 is predicted to have a similarly outstanding performance in capturing low-concentration Rn, compared to CC3 which was demonstrated in *Nature Materials* 13, 954-960 (2014)|doi: 10.1038/nmat4035.

SUMMARY

Figure 26:
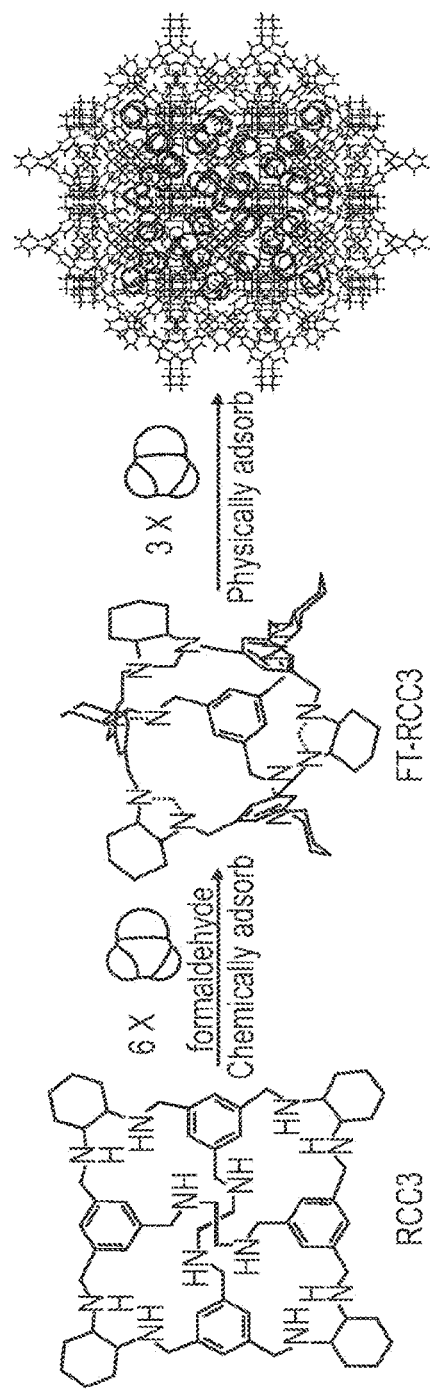
FIG. 26 is a scheme showing amine cage (RCC3) chemically absorbing gaseous formaldehyde; and the result product FT-RCC3 further physically absorbing formaldehyde—i.e. acting as a dual sorbent.

The data further illustrates the efficient capture of gaseous formaldehyde by the amine organic cage molecules described herein. The amine cage (RCC3) can act as a "dual sorbent" for gaseous formaldehyde, through both chemically absorbing formaldehyde by aminal formation reactions followed by physical absorbtion of formaldehyde within the pores stabilised in the post-chemically-absorbed cage (FT-RCC3) (FIG. 26). The overall uptake of formaldehyde is approximately 200 $cm^3/g$, which is about 20 times high than the best-performance formaldehyde adsorbent reported.

FIG. 26 is a scheme showing amine cage (RCC3) chemically absorbing gaseous formaldehyde; and the result product FT-RCC3 further physically absorbing formaldehyde— i.e. acting as a dual sorbent.

Furthermore, the materials of the invention exhibit advantageous selectivity and stability compared to comparative existing materials such as activated carbon materials. Firstly, the formaldehyde adsorption capability of activated carbon decreases dramatically under humid conditions because of the poor formaldehyde/$H_2O$ selectivity of this material. In contrast, RCC3 preferentially absorbs formaldehydes via reaction with pre-organized diamine group. The presence of water can even provide a benefit for the chemical absorbtion because of the reversibility of the aminal formation. Another big drawback of activated carbon as formaldehyde absorbent is the release of absorbed pollutant at high temperature or/and high humidity, which is a typical behaviour of physic adsorption. In contrast, chemically absorbed formaldehydes are robustly held (FT-RCC3). Decomposition and formaldehyde release appears not to occur until 300° C. as suggested by TGA experiment.

Finally. FT-RCC3, the post-chemical-absorbed cage can capture low concentrations of radon from air.

REFERENCES (1) Belowich, M. E.; Stoddart, J. F. *Chem. Soc. Rev.* 2012, 41, 2003.
(2) Fernando J, U.-R.; Hunt, J. R.; Furukawa, H.; Klöck, C.; O'Keeffe, M.; Yaghi, O. M. *J. Am. Chem. Soc.* 2009, 131, 4570.
(3) (a) Tozawa, T.; Jones, J. T.; Swamy, S. I.; Jiang, S.; Adams, D. J.; Shakespeare, S.; Clowes, R.; Bradshaw, D.; Hasell, T.; Chong, S. Y.; Tang, C.; Thompson, S.; Parker, J.; Trewin, A.; Bacsa, J.; Slawin, A. M.; Steiner, A.; Cooper, A. I. *Nat. Mater.* 2009, 8, 973. (b) Mastalerz, M. *Angew. Chem., Int. Ed.* 2010, 49, 5042. (c) Jin, Y.; Zhu, Y.; Zhang, W. *Crystengcomm* 2013, 15, 1484.
(4) Jones, J. T.; Hasell, T.; Wu, X.; Bacsa, J.; Jelfs, K. E.; Schmidtmann, M.; Chong, S. Y.; Adams, D. J.; Trewin, A.; Schiffman, F.; Cora, F.; Slater, B.; Steiner, A.; Day, G. M.; Cooper, A. I. *Nature* 2011, 474, 367. (b) Mastalerz, M. *Chem.-Eur. J.* 2012, 18, 10082. (c) Mastalerz, M.; Schneider, M. W.; Oppel, I. M.; Presly, O. *Angew. Chem., Int.* Ed. 2010, 50, 1046.
(5) Zhang, G.; Presly, O.; White, F.; Oppel, I. M.; Mastalerz, M. *Angew. Chem., Int.* Ed. 2014, 53, 1516.
(6) Farha, O. K.; Eryazici, I.; Jeong, N. C.; Hauser, B. G.; Wilmer, C. E.; Sarjeant, A. A.; Snurr, R. Q.; Nguyen, S. T.; Yazaydin, A. O.: Hupp, J. T. *J. Am. Chem. Soc.* 2012, 134, 15016.
(7) Hasell, T.; Schmidtmann, M.; Cooper, A. *J. Am. Chem. Soc.* 2011, 133, 14920.
(8) Bushell, A. F.; Budd, P. M.; Attfield, M. P.; Jones, J. T.; Hasell, T.; Cooper, A. I.; Bernardo, P.; Bazzarelli, F.; Clarizia, G.; Jansen, J. C. *Angew. Chem., Int. Ed.* 2013, 52, 1253.
(9) Mitra, T.; Jelfs, K. E.: Schmidtmann, M.; Ahmed, A.: Chong, S. Y.: Adams, D. J.: Cooper, A. I. *Nat. Chem.* 2013, 5, 276.
(10) Brutschy, M.; Schneider, M. W.; Mastalerz, M.; Waldvogel, S. R. *Adv. Mater.* 2012, 24, 6049.
(11) Hasell, T.; Schmidtmann, M.; Stone, C. A.; Smith, M. W.; Cooper, A. I. *Chem. Commun.* 2012, 48, 4689.
(12) Schneider, M. W.; Oppel, I. M.; Griffin, A.; Mastalerz, M. *Angew. Chem., Int. Ed.* 2013, 52, 3611.
(13) Planas, N.; Dzubak, A. L.; Poloni, R.; Lin, L.-C.; McManus, A.; McDonald, T. M.; Neaton, J. B.; Long, J. R.; Smit, B.; Gagliardi, L. *J. Am. Chem. Soc.* 2013, 130, 7402.
(14) (a) Swamy, S. I.; Bacsa, J.; Jones, J. T. A.; Stylianou, K. C.; Steiner, A.; Ritchie, L. K.; Hasell, T.; Gould, J. A.; Layboum, A.; Khimyak, Y. Z.; Adams, D. J.; Rosseinsky, M. J.; Cooper, A. I. *J. Am. Chem. Soc.* 2010, 132, 12773. (b) Culshaw, J. L.; Cheng, G.; Schmidtmann, M.; Hasell, T.; Liu, M.; Adams, D. J.; Cooper, A. I. *J. Am. Chem. Soc.* 2013, 135, 10007.
(15) (a) Jin, Y.; Voss, B. A.; Jin, A.; Long, H.; Noble, R. D.; Zhang, W. *J. Am. Chem. Soc.* 2011, 133, 6650. (b) Jin, Y.; Voss, B. A.; Noble, R. D.; Zhang, W. *Angew. Chem., nt. Ed.* 2010, 49, 6348.
(16) Mastalerz, M.; Schneider, M. W.; Oppel, I. M.; Presly, O. *Angew. Chem., Int. Ed.* 2011, 50, 1046.
(17) Hasell, T.; Chong, S. Y.; Jelfs, K. E.; Adams, D. J.; Cooper, A. I. *J. Am. Chem. Soc.* 2012, 134, 588.
(18) Jeffs, K. E.; Eden, E. G.; Culshaw, J. L.; Shakespeare, S.; Pyzer-Knapp, E. O.; Thompson, H. P.; Bacsa, J.; Day, G. M.; Adams, D. J.; Cooper, A. I. *J. Am. Chem. Soc.* 2013, 135, 9307.
(19) (a) Jones, M. D.; Mahon, M. F. *J. Organomet. Chem.* 2008, 693, 2377. (b) Jurčik, V.; Wilhelm, R. *Tetrahedron: Asymmetry* 2006, 17, 801. (c) Godin, G.; Levrand, B.; Trachsel, A.; Lehn, J. M.; Herrmann, A. *Chem. Commun.* 2010, 46, 3125. (d) Buchs née Levrand, B.; Godin, G.; Trachsel, A.; de Saint Laumer, J.-Y.; Lehn, J.-M.; Herrmann, A. *Eur. J. Org. Chem.* 2011, 2011, 681.
(20) Willems, T. F.; Rycroft, C. H.; Kazi, M.; Meza, J. C.; Haranczyk, M. *Micropor. Mesopor. Mater.* 2012, 149, 134.
(21) Robeson, L. M. *J. Membr. Sci.* 1991, 62, 165.
(22) Vaidhyanathan, R.; Iremonger, S. S.; Shimizu, G. K.; Boyd, P. G.; Alavi, S.; Woo, T. K. *Science* 2010, 330, 650.
(23) D. Holden, K. E. Jelfs, A. I. Cooper, A. Trewin, and D. J. Willock. *J. Phys. Chem. C,* 2012, 116, 16639.
(24) Jorgensen. W. L.; Maxwell, D.; Tirado-Rives, J. *J. Am. Chem. Soc.* 1996, 118, 11225.
(25) (a) McKeown, N. B.; Budd, P. M. Macromolecules 2010, 43, 5163. (b) Ben, T.; Ren, H.; Ma, S. Q.; Cao, D. P.; Lan, J. H.: Jing, X. F.; Wang, W. C.: Xu, J.; Deng. F.: Simmons, J. M.; Qiu, S. L.; Zhu, G. S. *Angew. Chem., Int. Ed.* 2009, 48, 9457.

(A1) Jones, J. T.; Hasell, T.; Wu, X.: Bacsa, J.: Jelfs, K. E.; Schmidtmann, M.; Chong, S. Y.; Adams, D. J.; Trewin, A.; Schiffman, F.; Cora, F.; Slater, B.; Steiner, A.; Day, G. M.; Cooper, A. I. *Nature* 2011, 474, 367.
(A2) Nowell, H.; Barnett, S. A.; Christensen, K. E.; Teat, S. J.; Allan, D. R. *J. Synchrotron Radiat.* 2012, 19, 435.
(A3) Sheldrick, G. M. (University of Göttingen, Germany) 2008.
(A4) Sheldrick, G. M. *Acta Crystallogr., Sect. A: Found. Crystallogr.* 2008, 64, 112.
(A5) Dolomanov, O. V.; Bourhis, L. J.; Gildea, R. J.; Howard, J. A. K.; Puschmann, H. *J. Appl. Cryst.* 2009, 42, 339.
(B1) Tozawa, T.; Jones, J. T.; Swamy, S. I.: Jiang, S.; Adams, D. J.; Shakespeare, S.; Clowes, R.; Bradshaw, D.; Hasell, T.; Chong, S. Y.; Tang, C.; Thompson, S.; Parker, J.; Trewin, A.; Bacsa, J.; Slawin, A. M.; Steiner, A.; Cooper, A. I. *Nat Mater* 2009, 8, 973.
(B2) Chen, L.; Reiss, P. S.; Chong, S. Y.; Holden, D.; Jelfs, K. E.; Hasell, T.; Little, M. A.; Kewley, A.; Briggs, M. E.; Stephenson, A.; Thomas, K. M.; Armstrong, J. A.; Bell, J.; Busto, J.; Noel, R.; Liu, J.; Strachan, D. M.; Thallapally, P. K.; Cooper, A. I. *Nat Mater* 2014, 13, 954.

Further Embodiments

The present invention may suitably be defined in accordance with any one or more of the ensuing numbered paragraphs:
1. A method of preparing a stabilised porous material from a collapsible substrate which, in a collapsed state, has a pore volume (and/or BET surface area) per gram (and/or per mole) that is lower than that of the corresponding stabilised porous material, the method comprising:
reacting the collapsible substrate with a molecular tie compound to cause at least one set (or pair) of distinct reactive moieties within the collapsible substrate to become mutually interlinked via a molecular tie linker derived from the molecular tie compound.
2. The method of paragraph 1, wherein the method first comprises forming the collapsible substrate, wherein forming the collapsible substrate comprises:
subjecting a hydrolytically-unstable porous precursor to a chemical stabilisation treatment to provide a chemically-stabilised collapsible substrate which is more hydrolytically stable than the porous precursor;
wherein both the collapsible substrate and the stabilised porous material are more hydrolytically stable than the hydrolytically-unstable porous precursor.
3. The method of paragraph 1, wherein:
the collapsible substrate is or comprises a polyamine compound, wherein the polyamine compound is a polyamine cage, a polyamine macrocycle, and/or a polyamine framework, and the distinct reactive moieties are reactive amine moieties; and
the stabilised porous material is a corresponding polyamine compound wherein at least two reactive amine moieties are interlinked via a molecular tie linker which forms a molecular bridge between the at least two reactive amine moieties.
4. The method of paragraph 3, wherein the stabilised porous material is formed by a reaction between a collapsible compound and molecular tie compound, wherein the reaction comprises:
reacting the collapsible compound (or a synthetic equivalent thereof), comprising one or more reactive units, with a molecular tie compound (or a synthetic equivalent thereof), comprising one or more reactable units, to form a stabilised compound (or precursor thereto—e.g. if subsequent deprotection or other transformation steps are required to furnish a final product) comprising one or more tied units;
wherein:
the one or more reactive units of the collapsible compound comprise one or more distinct reactive moieties (e.g. amine);
the one or more reactable units of the molecular tie compound comprise one or more reactable moieties (e.g. carbonyl, protected carbonyl, dihalo); and
the one or more tied units of the stabilised compound comprise one or more moieties characterised by the product of a reaction between the reactive unit(s) of the collapsible substrate and the molecular tie compound.
5. The method of paragraph 4, wherein the reaction comprises reacting a collapsible compound (or a synthetic equivalent thereof) comprising one or more reactive units defined by Formula A:

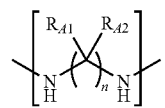

Formula A with a molecular tie compound (or a synthetic equivalent thereof) defined by Formula B:

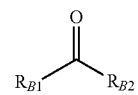

Formula B wherein:
n is an integer between 1 and 4;
each $R_{A1}$ and $R_{A2}$ group is independently hydrogen or an optionally substituted substituent group, wherein any pair of $R_{A1}$ and $R_{A2}$ groups are optionally joined together to form a carbocyclic, heterocyclic, aryl, or heteroaryl ring;
each $R_{B1}$ and $R_{B2}$ group is independently hydrogen or an optionally substituted substituent group, wherein any pair of $R_{B1}$ and $R_{B2}$ groups are optionally joined together to form a carbocyclic, heterocyclic, aryl, or heteroaryl ring;
to produce a stabilised porous material comprising one or more tied units defined by Formula C:

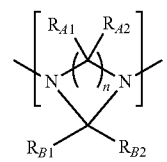

Formula C

6. The method of paragraph 5, wherein the collapsible compound comprises a plurality of reactive units of Formula $A_1$, each reactive unit being indirectly linked (through their connectable bonds denoted by square brackets) to a neighbouring distinct reactive unit via an intervening linker unit of Formula $A_L$ (through connectable bonds thereof denoted again by square brackets):

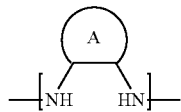

Formula $A_1$ wherein Ring A is a carbocyclic, aryl, heterocyclic, or heteroaryl ring;

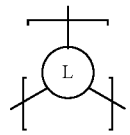

Formula $A_{1L}$ wherein Ring L is a polyvalent hydrocarbon (straight chain or branched), a polyvalent carbocycle, a polyvalent heterocycle, a polyvalent arene, a polyvalent heteroarene, a polyvalent mono-/poly-hydrocarbyl-carbocycle, a polyvalent mono-/poly-hydrocarbyl-heterocycle, a polyvalent mono-/poly-hydrocarbyl-arene, or a polyvalent mono-/poly-hydrocarbyl-heteroarene;

to produce a stabilised porous material comprising one or more tied units of Formula $C_1$:

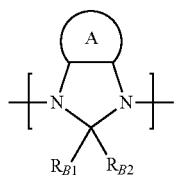

Formula $C_1$ wherein each tied unit of Formula $C_1$ is indirectly linked (through their connectable bonds denoted by square brackets) to a neighbouring distinct tied unit via the intervening linker unit of Formula $A_{1L}$;

wherein any of the groups of Formulae $A_1$, $A_{1L}$, or $C_1$ are optionally substituted.

7. The method of paragraph 6, wherein the reactive units of Formula $A_1$ are further defined by Formula $A_2$, the intervening linker unit of Formula $A_{1L}$ is further defined by formula $A_{2L}$, and the tied units of Formula $C_1$ are further defined by Formula $C_2$:

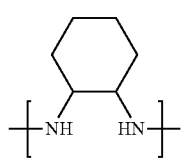

Formula $A_2$

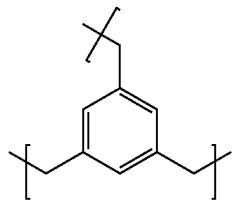

Formula $A_{2L}$

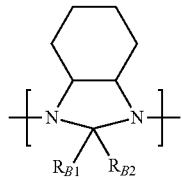

Formula $C_2$ wherein any of the groups of Formulae $A_1$, $A_{1L}$, or $C_1$ are optionally substituted.

8. The method of paragraph 7, wherein the collapsible compound is defined by Formula A3:

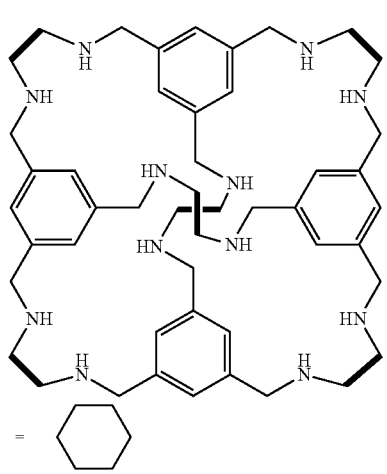

Formula A3

9. The method of paragraph 8, wherein all six reactive units (ethylenediamine units, or amine pairs) of the collapsible compound of Formula A3 are converted to corresponding tied units characterised by a molecular tie at each ethylenediamine unit.

10. The method of paragraph 5, wherein the molecular tie compound of Formula B is formaldehyde and/or acetone.

11. The method of paragraph 10, wherein the molecular tie compound is formaldehyde.

12. The method of paragraph 11, wherein the molecular tie compound is gaseous formaldehyde which is reacted in gaseous form with the collapsible substrate.

13. A stabilised porous material obtained by the method of paragraph 1.

14. A sorption composition comprising a stabilised porous material as paragraphed in paragraph 13 and/or a collapsible substrate as defined in paragraph 1, and optionally one or more additional porous and/or non-porous materials.

15. A method of sorbing one or more sorbable substrates, the method comprising:

contacting the one or more sorbable substrates with a sorption composition of paragraph 14;

wherein optionally, prior to contacting, the method comprises the step of preparing a sorption composition of paragraph 14 by:

providing a stabilised porous material through preparing a stabilised porous material, in accordance with the method of paragraph 1, by reacting a collapsible substrate with gaseous formaldehyde as a molecular tie compound.

16. The method of paragraph 15, wherein the one or more sorbable substrates comprise gaseous formaldehyde; and prior to contacting, the method comprises the step of preparing a sorption composition as defined in paragraph 15, such that gaseous formaldehyde is both a sorbable substrate and a molecular tie compound.

17. The method of paragraph 15, wherein the one or more sorbable substrates comprise radon.

18. The method of paragraph 15, wherein the one or more sorbable substrates comprise carbon dioxide.

19. A method of sorbing one or more molecular tie compounds, the method comprising contacting (or reacting) the one or more molecular tie compounds with a collapsible substrate as defined in paragraph 1 or a sorption composition thereof as defined in paragraph 14.

20. The method of paragraph 19, wherein the collapsible substrate or sorption composition thereof sorbs the one or more molecular tie compounds via both chemisorption and physisorption.

21. The method of paragraph 20, wherein the one or more molecular tie compounds comprise gaseous formaldehyde.

22. The method of paragraph 21, wherein the gaseous formaldehyde is present at a concentration of at or below 150 ppm.

23. A sorption complex, obtained by the method of sorbing as paragraphed in paragraph 15 or 19.

24. A stabilised porous material comprising a stabilised compound comprising at least one set (or pair) of distinct reactive moieties interlinked via a molecular tie linker.

25. The stabilised porous material of paragraph 24, wherein the stabilised porous material has a molar Brunauer-Emmett-Teller (BET) surface area of at least 100 m²//mmol.

26. The stabilised porous material of paragraph 24, wherein the stabilised compound comprises a plurality of tied units of Formula C:

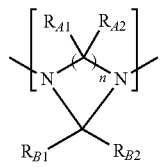

Formula C wherein each tied unit is optionally indirectly linked to one or more neighbouring tied units via an intervening linker unit.

27. The stabilised porous material of paragraph 26, wherein the or each intervening linker unit is defined by the Formula $A_{1L}$:

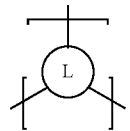

Formula $A_{1L}$ wherein Ring L is a polyvalent hydrocarbon (straight chain or branched), a polyvalent carbocycle, a polyvalent heterocycle, a polyvalent arene, a polyvalent heteroarene, a polyvalent mono-/poly-hydrocarbyl-carbocycle, a polyvalent mono-/poly-hydrocarbyl-heterocycle, a polyvalent mono-/poly-hydrocarbyl-arene, or a polyvalent mono-/poly-hydrocarbyl-heteroarene.

28. The stabilised porous material of paragraph 27, wherein the stabilised compound is defined by Formula C3:

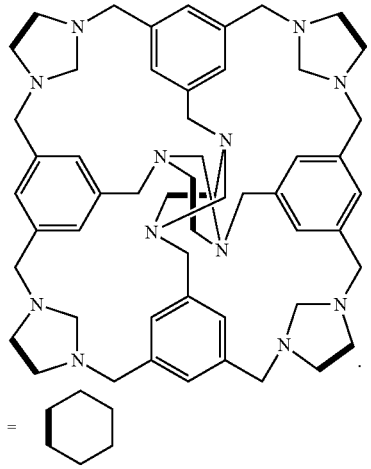

Formula C3

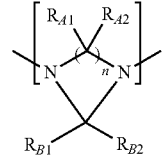

The invention claimed is:

1. A sorption composition, the sorption composition comprising:
   a stabilized porous material comprising a stabilized compound;
   wherein the stabilized compound comprises one or more tied units defined by Formula C:

$$\left[\begin{array}{c} R_{A1} \quad R_{A2} \\ \diagup \\ N \overset{n}{\frown} N \\ \diagdown \\ R_{B1} \quad R_{B2} \end{array}\right]$$

Formula C wherein:
   n is an integer between 1 and 4;
   each $R_{A1}$ and $R_{A2}$ group is independently hydrogen or an optionally substituted substituent group, wherein any pair of $R_{A1}$ and $R_{A2}$ groups are optionally joined together to form a carbocyclic, heterocyclic, aryl, or heteroaryl ring; and
   each $R_{B1}$ and $R_{B2}$ group is independently hydrogen or an optionally substituted substituent group, wherein any pair of $R_{B1}$ and $R_{B2}$ groups are optionally joined together to form a carbocyclic, heterocyclic, aryl, or heteroaryl ring.

2. A sorption device, the sorption device comprising the sorption composition as claimed in claim 1.

3. The sorption device of claim 2, wherein the sorption device is a formaldehyde scrubbing or filtration device.

4. The sorption device of claim 2, wherein the sorption device is a formaldehyde sensing device.

5. A method of sorbing carbon dioxide, the method comprising contacting carbon dioxide with the sorption composition as claimed in claim 1.

6. The sorption composition as claimed in claim 1, wherein the stabilized compound comprises a plurality of the tied units defined by the Formula C.

7. The sorption composition as claimed in claim 6, wherein the Formula C is further defined by the Formula $C_1$:

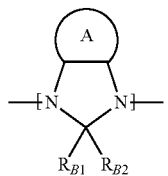

Formula C1 wherein Ring A is a carbocyclic, aryl, heterocyclic, or heteroaryl ring.

8. The sorption composition as claimed in claim 7, wherein the Formula $C_1$ is further defined by the Formula $C_2$:

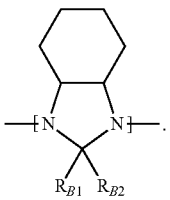

Formula C2

9. The sorption composition as claimed in claim 1, 6, 7, or 8, wherein each tied unit is indirectly linked to one or more neighbouring tied units via an intervening linker of Formula $L_1$.

10. The sorption composition as claimed in claim 9, wherein $L_1$ is selected from the group consisting of a polyvalent hydrocarbon (straight chain or branched), a polyvalent carbocycle, a polyvalent heterocycle, a polyvalent arene, a polyvalent heteroarene, a polyvalent mono-/poly-hydrocarbyl-carbocycle, a polyvalent mono-/poly-hydrocarbyl-heterocycle, a polyvalent mono-/poly-hydrocarbyl-arene, and a polyvalent mono-/poly-hydrocarbyl-heteroarene (where mono-/poly- indicates that the relevant ring system respectively comprises one or a plurality of hydrocarbyl substituents).

11. The sorption composition as claimed in claim 1, 6, 7, or 8, wherein each tied unit is indirectly linked to one or more neighbouring tied units via an intervening linker unit, and the or each intervening linker unit is defined by the Formula $A_{1L}$:

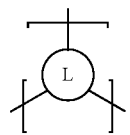

Formula $A_{1L}$ wherein Ring L is a straight chain or branched polyvalent hydrocarbon, a polyvalent carbocycle, a polyvalent heterocycle, a polyvalent arene, a polyvalent heteroarene, a polyvalent mono- or poly-hydrocarbyl-carbocycle, a polyvalent mono- or poly-hydrocarbyl-heterocycle, a polyvalent mono- or poly-hydrocarbyl-arene, or a polyvalent mono- or poly-hydrocarbyl-heteroarene.

12. The sorption composition as claimed in claim 1, 6, 7 or 8, wherein $R_{B1}$ and $R_{B2}$ are each independently selected from the group consisting of hydrogen and (1-3C)alkyl.

13. The sorption composition as claimed in claim 12, wherein $R_{B1}$ and $R_{B2}$ are each independently selected from the group consisting of hydrogen and methyl.

14. The sorption composition as claimed in claim 13, wherein $R_{B1}$ and $R_{B2}$ are both either hydrogen or methyl.

15. The sorption composition as claimed in claim 1, wherein the stabilized compound is the product of a reaction between a compound defined Formula A3 and a molecular tie compound (or a synthetic equivalent thereof) defined by Formula B:

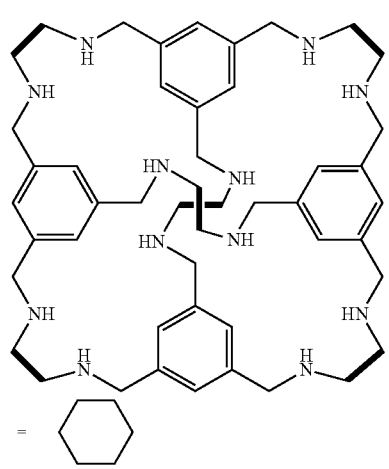

Formula A3

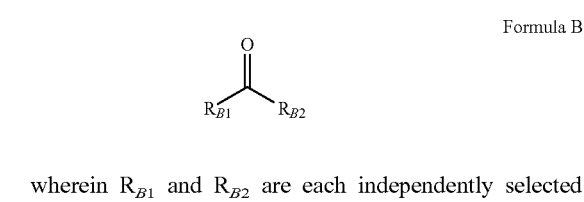

Formula B wherein $R_{B1}$ and $R_{B2}$ are each independently selected from the group consisting of hydrogen and (1-3C)alkyl.

16. The sorption composition as claimed in claim 1, wherein the stabilized compound is defined by Formula C3:

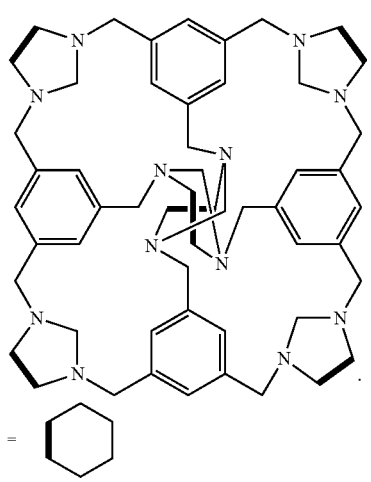

Formula C3

* * * * *